United States Patent [19]
Donahoe et al.

[11] Patent Number: 5,912,224
[45] Date of Patent: Jun. 15, 1999

[54] METHODS AND COMPOSITIONS FOR ENHANCING CELLULAR RESPONSE TO TGF-β LIGANDS

[75] Inventors: Patricia K. Donahoe, Weston; Tongwen Wang, Arlington, both of Mass.

[73] Assignee: The General Hospital Corporation, Boston, Mass.

[21] Appl. No.: 08/803,899

[22] Filed: Feb. 21, 1997

Related U.S. Application Data

[60] Provisional application No. 60/012,054, Feb. 22, 1996.

[51] Int. Cl.$^6$ ........................... A61K 31/33; A61K 38/18
[52] U.S. Cl. ............................... 514/2; 514/12; 514/291; 424/85.1; 424/198.1; 530/399
[58] Field of Search ................................ 424/122, 198.1, 424/350, 559, 85.1; 530/399; 514/2, 291, 886, 925, 12

[56] References Cited

U.S. PATENT DOCUMENTS

| | | |
|---|---|---|
| 4,885,171 | 12/1989 | Surendra . |
| 5,008,240 | 4/1991 | Bentz . |
| 5,011,687 | 4/1991 | Donahoe . |
| 5,286,730 | 2/1994 | Caufield . |
| 5,310,880 | 5/1994 | Donahoe . |
| 5,387,589 | 2/1995 | Kulkarni . |
| 5,411,940 | 5/1995 | Nixon . |
| 5,436,228 | 7/1995 | Postlethwaite et al. . |

FOREIGN PATENT DOCUMENTS

| | | |
|---|---|---|
| WO 94/21634 | 9/1994 | WIPO . |
| WO 95/01801 | 1/1995 | WIPO . |
| WO 95/06649 | 3/1995 | WIPO . |

OTHER PUBLICATIONS

Andres, D.A., et al., "Mutational Analysis of α–Subunit of Protein Farnesyltransferase. Evidence for a Catalytic Role," *J. Biol. Chem.* 268(2):1383–1390 (1993).

Andres, D.A., et al., "cDNA Cloning of the Two Subunits of Human CAAX Farnesyltransferase and Chromosomal Mapping of FNTA and FNTB Loci and Related Sequences," *Genomics* 18(1):105–112 (1993).

Bassing, C.H., et al., "A Transforming Growth Factor β Type I Receptor That Signals to Activate Gene Expression," *Science* 263:87–89 (1994).

Becker, J.W., et al., "FK–506–binding Protein: Three–dimensional Structure of the Complex with the Antagonist L–685,818," *J. Biol. Chem.* 268(15):11335–11339 (1993).

Brown, E.J., et al., "Control of p70 S6 kinase activity of FRAP in vivo," *Nature* 377:441–446 (Oct. 1995).

Cameron, A.M., et al., "Immunophilin FK506 bindig protein associated with inositol 1,4,5–trisphosphate receptor modulates calcium flux," *Proc. Natl. Acad. Sci. USA* 92:1784–1788 (Feb. 1995).

Cameron, A.M., et al., "Calcineurin Associated with the Inositol 1,4,5–Trisphosphate Receptor–FKBP12 Complex Modulates Ca$^{2+}$ Flux," *Cell* 83:463–472 (Nov. 1995).

Cate, R.L., et al., "Isolation of the Bovine and Human Genes for Mëllerian Inhibiting Substance and Expression of the Human Gene in Animal Cells," *Cell* 45:685–698 (1986).

Derynck, R., et al., "A new type of transforming growth factor–β, TGF–β3," *EMBO J.* 7(12):3737–3743 (1988).

Donahoe, P.K., et al., "A Graded Organ Culture Assay for the Detection of Mullerian Inhibiting Substance," *J. Surg. Res.* 23:141–148 (1977).

Ebner, R., et al., "Cloning of a Type I TGF–β Receptor and Its Effect on TGF–β Binding to the Type II Receptor," *Science* 260:1344–1348 (1993).

Forage, R.G., et al., "Cloning and sequence analysis of cDNA species coding for the two subunits of inhibin from bovine follicular fluid," *Proc. Natl. Acad. Sci. USA* 83:3091–3095 (1986).

Franzén, P., et al., "Cloning of a TGFβ Type I Receptor That Forms a Heteromeric Complex with the TGFβ Type II Receptor," *Cell* 75:681–692 (1993).

Galat, A., et al., "A Rapamycin–Selective 25–kDa Immunophilin," *Biochemistry* 31:2427–2434 (1992).

Gyuris, J., et al., "Cdi1, a Human G1 and S Phase Protein Phosphatase That Associated with Cdk2," *Cell* 75:791–803 (1993).

He, W.W., et al., "Developmental Expression of Four Novel Serine/Threonine Kinase Receptors Homologous to the Activin/Transforming Growth Factor–β Type II Receptor Family," *Dev. Dyn.* 196:133–142 (1993).

Laiho, M., et al., "Concomitant Loss of Transforming Growth Factor (TGF)–β Receptor Types I and II in TGF–β–resistant Cell Mutants Implicates Both Receptor Types in Signal Transduction," *J. Biol. Chem.* 265(30):18518–18524 (1990).

Lin, H.Y., et al., "Expression Cloning of the TGF–β Type II Receptor, a Functional Transmembrane Serine/Threonine Kinase," *Cell* 68:775–785 (1992).

Liu, J., et al., "Inhibition of T Cell Signaling by Immunophilin–Ligand Complexes Correlates with Loss of Calcineurin Phosphatase Activity," *Biochemistry* 31:3896–3901 (1992).

Lyons, K., et al., "Vgr–1, a mammalian gene related to Xenopus Vg–1, is a member of the transforming growth factor β gene superfamily," *Proc. Natl. Acad. Sci. USA* 86:4554–4558 (1989).

(List continued on next page.)

*Primary Examiner*—Toni R. Scheiner
*Assistant Examiner*—Nancy A. Johnson
*Attorney, Agent, or Firm*—Sterne, Kessler, Goldstein & Fox P.L.L.C.

[57] ABSTRACT

The present invention concerns the TGF-β receptor-mediated signaling pathway. The invention is based on the unexpected finding that TGF-β receptor-mediated signaling is inhibited by the cytoplasmic interactor FKBP12. The invention further concerns methods and pharmaceutical compositions for enhancing cellular response to TGF-β ligands. A screening assay is also provided for identifying macrolide potentiators capable of binding FKBP12 and thereby blocking FKBP12-inhibition of TGF-β receptor-mediated signaling.

31 Claims, 28 Drawing Sheets

OTHER PUBLICATIONS

McAlpine, J.B., et al., "Revised NMR Assignments for Rapamycin," *J. Antibiotics* 44(6):688–690 (1991).

MacLaughlin, D.T., et al., "Mullerian Duct Regression and Antiproliferative Bioactivities of Mullerian Inhibiting Substance Reside in its Carboxy–Terminal Domain," *Endocrinology* 131(1):1–6 (1992).

Mulder, K.M., and Morris, S.L., "Activation of $p21^{ras}$ by Transforming Growth Factor β in Epithelial Cells," *J. Biol. Chem.* 267(8):5029–5031 (1992).

Padgett, R.W., et al., "A transcript from a Drosphila pattern gene predicts a protein homologous to the transforming growth factor–β family," *Nature* 325:81–84 (1987).

Rotonda, J., et al., "Improved Calcineurin Inhibition by Yeast FKBP12–Drug Complexes," *J. Biol. Chem.* 268(11):7607–7609 (1993).

Sabatini, D.M., et al., "RAFT1: A Mammalian Protein That Binds to FKBP12 in a Rapamycin–Dependent Fashion and Is Homologous to Yeast TORs," *Cell* 78:35–43 (1994).

Schreiber, S.L., "Chemistry and Biology of the Immunophilins and Their Immunosuppressive Ligands," *Science* 251:283–287 (1991).

Siekierka, J.J., et al., "A cytosolic binding protein for the immunosuppressant FK506 has peptidyl–prolyl isomerase activity but is distinct from cyclophilin," *Nature* 341:755–757 (1989).

Standaert, R.F., et al., "Molecular cloning and overexpression of the human FK506–binding protein FKBP," *Nature* 346:671–674 (1990).

Tanaka, H., et al., "Structure of FK506: A Novel Immunosuppressant Isolated from *Streptomyces,*" *J. Am. Chem. Soc.* 109:5031–5033 (1987).

Trelstad, R.L., et al., "The Epithelial–Mesenchymal Interface of the Male Rat Mullerian Duct: Loss of Basement Membrane Integrity and Ductal Regression," *Devl. Biol.* 92:27–40 (1982).

Wang, T., et al., "Specific Interaction of Type I Receptors of the TGF–β Family with the Immunophilin FKBP–12," *Science* 265:674–676 (1994).

Wang, T., et al., "The Immunophilin FKBP12 Functions as a Common Inhibitor of the TGFβ Family Type I Receptors," *Cell* 86:435–444 (Aug. 1996).

Wang, T., et al., "The $p21^{ras}$ Farnesyltransferase α Subunit in TGF–β and Activin Signaling," *Science* 271:1120–1122 (Feb. 23, 1996).

Wieser, R., et al., "GS domain mutations that constitutively activate TβR–I, the downstream signaling component in the TGF–β receptor complex," *EMBO J.* 14(10):2199–2208 (May 1995).

Wozney, J.M., et al., "Novel Regulators of Bone Formation: Molecular Clones and Activities," *Science* 242:1528–1534 (1988).

Wrana, J.L., et al., "TGFβ Signals through a Heteromeric Protein Kinase Receptor Complex," *Cell* 71(6):1003–1014 (1992).

Wrana, J.L., et al., "Mechanism of activation of the TGF–β receptor," *Nature* 370:341–347 (1994).

Xie, T., et al., "The *Drosphila saxophone* Gene: A Serine–Threonine Kinase Receptor of the TGF–β Superfamily," *Science* 263:1756–1759 (1994).

Brummel, T.J. et al., "Characterization and Relationship of Dpp Receptors encoded by the saxophone and thick veins Genes in Drosophila," *Cell* 78:251–261 (1994).

ten Dijke, P. et al., "Activin receptor–like kinases: a novel subclass of cell–surface receptors with predicted serine/threonine kinase activity," *Oncogene* 8:2879–2887 (1993).

ten Dijke, P. et al., "Characterization of Type I Receptors for Transforming Growth Factor–β and Activin," *Science* 264:101–104 (1994).

Thomson, A.W. et al., "Mode of Action of Tacrolimus (FK506): Molecular and Cellular Mechanisms," *Ther. Drug Monit.* 17(6):584–591 (Dec. 1995).

Charng, M.J. et al., "FKBP–12 Recognition Is Dispensable For Signal Generation by Type I Transforming Growth Factor–β Receptors," *J. Biol. Chem.* 271(38):22941–22944 (Sep. 1996).

Okadome, T. et al., "Characterization of the Interaction of FKBP12 with the Transforming Growth Factor–β Type I Receptor in Vivo," *J. Biol. Chem.* 271(360):21687–21690 (Sep. 1996).

Rao, P. et al., "Effect of FK 506 on FK–Binding Protein and Transforming Growth Factor Beta Gene Expression," *Trans. Proc.* 23(6):2873–2874 (1991).

Palladino, Annals NY Acad. Sci. 593:181, 1990.

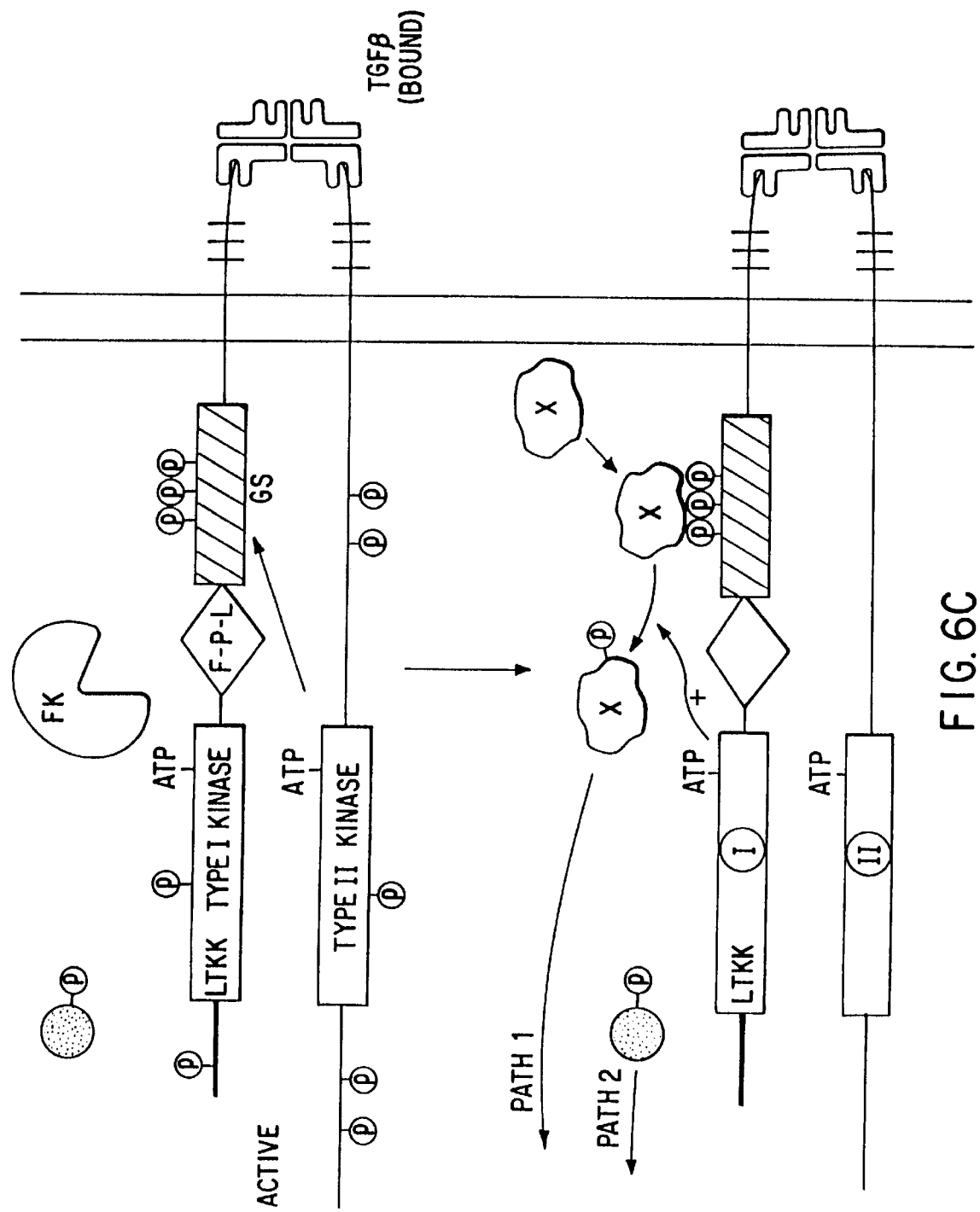

```
ATGGGAGTAC AAGTAGTTCC AATTGCTCCT GGTGATGGCA GCACCTATCC CAAGAATGGC   60
 M  G  V    Q  V  V    P  I  A    P  G  D    G  S  T    Y  P  K  N  G

CAAAAGGTCA CGGTCCACTA CACCGGCACC CTGGACGATG GCACCAAGTT CGATTCGTCG  120
 Q  K  V    T  V  H    Y  T  G    T  L  D    D  G  T    K  F  D  S  S

CGCGACCGCA ACAAGCCATT CAAGTTCACC ATCGGCAAGG GCGAGGTCAT CCGTGGCTGG  180
 R  D  R    N  K  P    F  K  F    T  I  G    K  G  E    V  I  R  G  W

GATGAGGGAG TTGCCCAGTT GAGCGTCGGC CAGAGCGCCA AGCTGATTTG CTCGCCGGAC  240
 D  E  G    V  A  Q    L  S  V    G  Q  S    A  K  L    I  C  S  P  D

TATGCCTACG GTAGCCGTGG CCACCCCGGC GTCATTCCGC CAACTCCAC CCTCACCTTC  300
 Y  A  Y    G  S  R    G  H  P    G  V  I    P  P  N    S  T  L  T  F

GACGTCGAGC TGCTCAAGGT CGAATAGgcg cacaggatgc caatgtgta taccccaaac  360
 D  V  E    L  L  K    V  E  * caaatcgcag ggggttgcgg accggcgcac cggcgacgag ccgaagaaca tcataatcgg  420
aaccagaaca atccagcagc atttgccaac ccaaaataat aatgataact tcatacacag  480
ctctaaacta gaactaattt aaccgcaaag ggaacgcatc ttctaccaat acaaataaac  540
atttattcaa gtcaaaaaaa aaaaaaaaa a
```

FIG.7A

```
Hfk12   . . . . . . . . . . . . . . . . . . . . . . . . . . . . . . . . . . . . . . . . . . MGVQVETISP  GDGRTF  . . . . . . . . . .  . . . . . . . . . .  18
Rfk12   . . . . . . . . . . . . . . . . . . . . . . . . . . . . . . . . . . . . . . . . . . MGVQVETISS  GDGRTF  . . . . . . . . . .  . . . . . . . . . .  18
Drfk12  . . . . . . . . . . . . . . . . . . . . . . . . . . . . . . . . . . . . . . . . . . MGVQVVPIAP  GDGSIY  . . . . . . . . . .  . . . . . . . . . .  18
Hfk13   . . . . . . . . . . . . . . . . . . . . . RLSWFRVLTV  LSICLSAWAS  TGTEGK           PK  . . . . . . . . . .  . . . . . . . . . .  39
Hfk25   M TAYNHLFETK  RFKGTESISK  VSEQKNVKL  NEDKPKETKS  EETLDEGPPK  LQIGVKKRVD  YTKSVLKKGD  120

Hfk12   . . . . . . . . . . . RGQ  RAK  TCVVHYTGML  EDGKKFDSS.  RDRN  KPFKFM  GKQ  EVIRGWEEGV  64
Rfk12   . . . . . . . . . . . RGQ  RAK  TCVVHYTGML  EDGKKFDSS.  RDRN  KPFKFT  LGKG  EVIRGWEEGV  64
Drfk12  . . . . . . . . . . . NGQ  SAK  KVTVHYTGTL  DDGTKFDSS.  RDRN  KPFKFT  IGKG  EVIRGWDEGV  64
Hfk13   . . HCPIKSRKGD  KRK  VLHMYTGKL  EDGTFDSS..  . . .  QPFMFS  LGTG  QVIKGWDQGL  92
Hfk25   KTNF.PKKGD  EAR  VVHCWYTGTL  QDGIVEDTNI  QTSAKKKKNA  KPLSFKVGVG  KVIRGWDEAL  179

Hfk12   AQMSVGQRAK  IT  ISPDYAYG  ATGHP.GIIP  PHATLVFDVE  LLKLE  . . . . . . . . . .  108
Rfk12   AQMSVGQRAK  II  ISPDYAYG  ATGHP.GIIP  PHATLVFDVE  LLKLE  . . . . . . . . . .  108
Drfk12  AQISVGQSAK  IC  SPDYAYG  SRGHP.GVIP  PNSTLTFDVE  LLKVE  . . . . . . . . . .  108
Hfk13   LGMYEGEKRK  LV  IPSELGYG  ERGAP.PKIP  GGATLVFEVE  LLKIERRTEL  141
Hfk25   LTMSKGEKAR  LE  IEEWAYG  KKGQPDAKIP  PNARLTEEVE  LVDID . . . .  224
```

FIG. 7C

FNTA (L)

1087
AGA TCC CTT CAA AGC AAA CAC AGC ACA GAA AAT GAC TCA CCA
Arg Ser Leu Gln Ser Lys His Ser Thr Glu Asn Asp Ser Pro

ACA AAT GTA CAG CAA TAA
Thr Asn Val Gln Gln caccatccagaa......gtatctaaaaaaaaaaaaaaaaaaaaaaaaaaa 1670

FNTA (S)

1087
AGA TCC CTT CAA AGC AAA CAC AAC ACA TAA
Arg Ser Leu Gln Ser Lys His Asn Thr aaaaaaaaaaaaaaaa 1132

● FKBP12  
↓ MYRISTYLATED MUTANT FKBP12

● MYRISTYLATED FKBP12  
▨ CYTOPLASMIC INHIBITOR

```
                              SEQUENCE LISTING ( 1 ) GENERAL INFORMATION:

( iii ) NUMBER OF SEQUENCES: 26

( 2 ) INFORMATION FOR SEQ ID NO:1:

( i ) SEQUENCE CHARACTERISTICS:
            ( A ) LENGTH: 571 base pairs
            ( B ) TYPE: nucleic acid
            ( C ) STRANDEDNESS: double
            ( D ) TOPOLOGY: linear ( ii ) MOLECULE TYPE: DNA (genomic)

( ix ) FEATURE:
            ( A ) NAME/KEY: CDS
            ( B ) LOCATION: 1..324

( xi ) SEQUENCE DESCRIPTION: SEQ ID NO:1:

ATG GGA GTA CAA GTA GTT CCA ATT GCT CCT GGT GAT GGC AGC ACC TAT          48
Met Gly Val Gln Val Val Pro Ile Ala Pro Gly Asp Gly Ser Thr Tyr
 1               5                  10                  15

CCC AAG AAT GGC CAA AAG GTC ACG GTC CAC TAC ACC GGC ACC CTG GAC          96
Pro Lys Asn Gly Gln Lys Val Thr Val His Tyr Thr Gly Thr Leu Asp
             20                  25                  30

GAT GGC ACC AAG TTC GAT TCG TCG CGC GAC CGC AAC AAG CCA TTC AAG         144
Asp Gly Thr Lys Phe Asp Ser Ser Arg Asp Arg Asn Lys Pro Phe Lys
         35                  40                  45

TTC ACC ATC GGC AAG GGC GAG GTC ATC CGT GGC TGG GAT GAG GGA GTT         192
Phe Thr Ile Gly Lys Gly Glu Val Ile Arg Gly Trp Asp Glu Gly Val
     50                  55                  60

GCC CAG TTG AGC GTC GGC CAG AGC GCC AAG CTG ATT TGC TCG CCG GAC         240
Ala Gln Leu Ser Val Gly Gln Ser Ala Lys Leu Ile Cys Ser Pro Asp
 65                  70                  75                  80

TAT GCC TAC GGT AGC CGT GGC CAC CCC GGC GTC ATT CCG CCC AAC TCC         288
Tyr Ala Tyr Gly Ser Arg Gly His Pro Gly Val Ile Pro Pro Asn Ser
                 85                  90                  95

ACC CTC ACC TTC GAC GTC GAG CTG CTC AAG GTC GAA TAGGCGCACA              334
Thr Leu Thr Phe Asp Val Glu Leu Leu Lys Val Glu
            100                 105

GGATGCCCAA TGTGTATACC CCAAACCAAA TCGCAGGGGG TTGCGGACCG GCGCACCGGC       394

GACGAGCCGA AGAACATCAT AATCGGAACC AGAACAATCC AGCAGCATTT GCCAACCCAA       454

AATAATAATG ATAACTTCAT ACACAGCTCT AAACTAGAAC TAATTTAACC GCAAAGGGAA       514

CGCATCTTCT ACCAATACAA ATAAACATTT ATTCAAGTCA AAAAAAAAAA AAAAAAA          571

( 2 ) INFORMATION FOR SEQ ID NO:2:

( i ) SEQUENCE CHARACTERISTICS:
            ( A ) LENGTH: 108 amino acids
            ( B ) TYPE: amino acid
            ( D ) TOPOLOGY: linear
```

(ii) MOLECULE TYPE: protein (xi) SEQUENCE DESCRIPTION: SEQ ID NO:2:

```
Met Gly Val Gln Val Val Pro Ile Ala Pro Gly Asp Gly Ser Thr Tyr
 1               5                  10                  15

Pro Lys Asn Gly Gln Lys Val Thr Val His Tyr Thr Gly Thr Leu Asp
                20                  25                  30

Asp Gly Thr Lys Phe Asp Ser Ser Arg Asp Arg Asn Lys Pro Phe Lys
            35                  40                  45

Phe Thr Ile Gly Lys Gly Glu Val Ile Arg Gly Trp Asp Glu Gly Val
        50                  55                  60

Ala Gln Leu Ser Val Gly Gln Ser Ala Lys Leu Ile Cys Ser Pro Asp
65                  70                  75                  80

Tyr Ala Tyr Gly Ser Arg Gly His Pro Gly Val Ile Pro Pro Asn Ser
                85                  90                  95

Thr Leu Thr Phe Asp Val Glu Leu Leu Lys Val Glu
                100                 105
```

(2) INFORMATION FOR SEQ ID NO:3:

(i) SEQUENCE CHARACTERISTICS:
        (A) LENGTH: 108 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Met Gly Val Gln Val Glu Thr Ile Ser Pro Gly Asp Gly Arg Thr Phe
 1               5                  10                  15

Pro Lys Arg Gly Gln Thr Cys Val Val His Tyr Thr Gly Met Leu Glu
                20                  25                  30

Asp Gly Lys Lys Phe Asp Ser Ser Arg Asp Arg Asn Lys Pro Phe Lys
            35                  40                  45

Phe Met Leu Gly Lys Gln Glu Val Ile Arg Gly Trp Glu Glu Gly Val
        50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
                100                 105
```

(2) INFORMATION FOR SEQ ID NO:4:

(i) SEQUENCE CHARACTERISTICS:
        (A) LENGTH: 108 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

```
Met Gly Val Gln Val Glu Thr Ile Ser Ser Gly Asp Gly Arg Thr Phe
 1               5                  10                  15

Pro Lys Arg Gly Gln Thr Cys Val Val His Tyr Thr Gly Met Leu Glu
                20                  25                  30

Asp Gly Lys Lys Phe Asp Ser Ser Arg Asp Arg Asn Lys Pro Phe Lys
```

```
                35                  40                  45
Phe Thr Leu Gly Lys Gln Glu Val Ile Arg Gly Trp Glu Glu Gly Val
    50                  55                  60
Ala Gln Met Ser Val Gly Gln Arg Ala Lys Leu Ile Ile Ser Pro Asp
65                  70                  75                  80
Tyr Ala Tyr Gly Ala Thr Gly His Pro Gly Ile Ile Pro Pro His Ala
                85                  90                  95
Thr Leu Val Phe Asp Val Glu Leu Leu Lys Leu Glu
            100                 105
```

(2) INFORMATION FOR SEQ ID NO:5:

(i) SEQUENCE CHARACTERISTICS:
        (A) LENGTH: 108 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Met Gly Val Gln Val Val Pro Ile Ala Pro Gly Asp Gly Ser Thr Tyr
1               5                   10                  15
Pro Lys Asn Gly Gln Lys Val Thr Val His Tyr Thr Gly Thr Leu Asp
                20                  25                  30
Asp Gly Thr Lys Phe Asp Ser Ser Arg Asp Arg Asn Lys Pro Phe Lys
            35                  40                  45
Phe Thr Ile Gly Lys Gly Glu Val Ile Arg Gly Trp Asp Glu Gly Val
    50                  55                  60
Ala Gln Leu Ser Val Gly Gln Ser Ala Lys Leu Ile Cys Ser Pro Asp
65                  70                  75                  80
Tyr Ala Tyr Gly Ser Arg Gly His Pro Gly Val Ile Pro Pro Asn Ser
                85                  90                  95
Thr Leu Thr Phe Asp Val Glu Leu Leu Lys Val Glu
            100                 105
```

(2) INFORMATION FOR SEQ ID NO:6:

(i) SEQUENCE CHARACTERISTICS:
        (A) LENGTH: 141 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Met Arg Leu Ser Trp Phe Arg Val Leu Thr Val Leu Ser Ile Cys Leu
1               5                   10                  15
Ser Ala Val Ala Ser Thr Gly Thr Glu Gly Lys Arg Lys Leu Gln Ile
                20                  25                  30
Gly Val Lys Lys Arg Val Asp His Cys Pro Ile Lys Ser Arg Lys Gly
            35                  40                  45
Asp Val Leu His Met His Tyr Thr Gly Lys Leu Glu Asp Gly Thr Glu
    50                  55                  60
Phe Asp Ser Ser Leu Pro Gln Asn Gln Pro Phe Val Phe Ser Leu Gly
65                  70                  75                  80
Thr Gly Gln Val Ile Lys Gly Trp Asp Gln Gly Leu Leu Gly Met Tyr
                85                  90                  95
Glu Gly Glu Lys Arg Lys Leu Val Ile Pro Ser Glu Leu Gly Tyr Gly
```

```
                      100                 105                 110
Glu  Arg  Gly  Ala  Pro  Pro  Lys  Ile  Pro  Gly  Gly  Ala  Thr  Leu  Val  Phe
              115                 120                 125

Glu  Val  Glu  Leu  Leu  Lys  Ile  Glu  Arg  Arg  Thr  Glu  Leu
     130                 135                 140
```

(2) INFORMATION FOR SEQ ID NO:7:

(i) SEQUENCE CHARACTERISTICS:
        (A) LENGTH: 164 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

```
Thr  Ala  Tyr  Asn  His  Leu  Phe  Glu  Thr  Lys  Arg  Phe  Lys  Gly  Thr  Glu
1                   5                   10                  15

Ser  Ile  Ser  Lys  Val  Ser  Glu  Gln  Val  Lys  Asn  Val  Lys  Leu  Asn  Glu
               20                  25                  30

Asp  Lys  Pro  Lys  Glu  Thr  Lys  Ser  Glu  Glu  Thr  Leu  Asp  Glu  Gly  Pro
          35                  40                  45

Pro  Lys  Tyr  Thr  Lys  Ser  Val  Leu  Lys  Lys  Gly  Asp  Lys  Thr  Asn  Phe
     50                  55                  60

Pro  Lys  Lys  Gly  Asp  Val  Val  His  Cys  Trp  Tyr  Thr  Gly  Thr  Leu  Gln
65                  70                  75                  80

Asp  Gly  Thr  Val  Phe  Asp  Thr  Asn  Ile  Gln  Thr  Ser  Ala  Lys  Lys  Lys
                85                  90                  95

Lys  Asn  Ala  Lys  Pro  Leu  Ser  Phe  Lys  Val  Gly  Val  Gly  Lys  Val  Ile
               100                 105                 110

Arg  Gly  Trp  Asp  Glu  Ala  Leu  Leu  Thr  Met  Ser  Lys  Gly  Glu  Lys  Ala
          115                 120                 125

Arg  Leu  Glu  Ile  Glu  Pro  Glu  Trp  Ala  Tyr  Gly  Lys  Lys  Gly  Gln  Pro
     130                 135                 140

Asp  Ala  Lys  Ile  Pro  Pro  Asn  Ala  Lys  Leu  Thr  Phe  Glu  Val  Glu  Leu
145                 150                 155                 160

Val  Asp  Ile  Asp
```

(2) INFORMATION FOR SEQ ID NO:8:

(i) SEQUENCE CHARACTERISTICS:
        (A) LENGTH: 104 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO:8:

```
AGA TCC CTT CAA AGC AAA CAC AGC ACA GAA AAT GAC TCA CCA ACA AAT        48
Arg Ser Leu Gln Ser Lys His Ser Thr Glu Asn Asp Ser Pro Thr Asn
1               5                   10                  15

GTA CAG CAA TAACACCATC CAGAAGTATC TAAAAAAAAA AAAAAAAAA AAAAAA         104
Val Gln Gln
```

(2) INFORMATION FOR SEQ ID NO:9:

(i) SEQUENCE CHARACTERISTICS:
            (A) LENGTH: 19 amino acids
            (B) TYPE: amino acid
            (D) TOPOLOGY: linear (ii) MOLECULE TYPE: protein (xi) SEQUENCE DESCRIPTION: SEQ ID NO:9:

Arg Ser Leu Gln Ser Lys His Ser Thr Glu Asn Asp Ser Pro Thr Asn
 1               5                  10                  15

Val Gln Gln (2) INFORMATION FOR SEQ ID NO:10:

(i) SEQUENCE CHARACTERISTICS:
            (A) LENGTH: 46 base pairs
            (B) TYPE: nucleic acid
            (C) STRANDEDNESS: double
            (D) TOPOLOGY: linear (ii) MOLECULE TYPE: cDNA (ix) FEATURE:
            (A) NAME/KEY: CDS
            (B) LOCATION: 1..27

(xi) SEQUENCE DESCRIPTION: SEQ ID NO:10:

AGA TCC CTT CAA AGC AAA CAC AAC ACA TAAAAAAAAA AAAAAAAA                46
Arg Ser Leu Gln Ser Lys His Asn Thr
 20                  25

(2) INFORMATION FOR SEQ ID NO:11:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO:11:

Arg Ser Leu Gln Ser Lys His Asn Thr
 1               5

(2) INFORMATION FOR SEQ ID NO:12:

(i) SEQUENCE CHARACTERISTICS:
            (A) LENGTH: 13 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:12:

Thr Thr Ser Gly Ser Gly Ser Gly Leu Pro Leu Thr Thr
 1               5                  10

(2) INFORMATION FOR SEQ ID NO:13:

(i) SEQUENCE CHARACTERISTICS:
            (A) LENGTH: 13 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:13:

Thr Thr Ala Gly Ala Gly Ala Gly Leu Pro Leu Thr Thr

```
1               5                   10
```

(2) INFORMATION FOR SEQ ID NO:14:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

```
Thr Thr Ala Gly Ser Gly Ser Gly Leu Pro Leu Thr Thr
1               5                   10
```

(2) INFORMATION FOR SEQ ID NO:15:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

```
Thr Thr Ser Gly Ala Gly Ser Gly Leu Pro Leu Thr Thr
1               5                   10
```

(2) INFORMATION FOR SEQ ID NO:16:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

```
Thr Thr Ser Gly Ser Gly Ala Gly Leu Pro Leu Thr Thr
1               5                   10
```

(2) INFORMATION FOR SEQ ID NO:17:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

```
Thr Thr Ser Gly Ser Gly Ser Gly Leu Gly Leu Thr Thr
1               5                   10
```

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

```
Thr Thr Ser Gly Ser Gly Ser Gly
```

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

```
Ser Cys Thr Ser Gly Ser Gly Ser Gly Leu Pro Phe
1               5                   10
```

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

```
Thr Thr Ser Gly Ser Gly Ser Gly Leu Pro Leu
1               5                   10
```

(2) INFORMATION FOR SEQ ID NO:21:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

```
Ser Gly Ser Gly Ser Gly
1               5
```

(2) INFORMATION FOR SEQ ID NO:22:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

```
Leu Pro Leu Phe
1
```

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

```
Leu Arg Ile Val Lys Lys Thr Leu
```

```
(2) INFORMATION FOR SEQ ID NO:24:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Leu Pro Phe Leu
1

(2) INFORMATION FOR SEQ ID NO:25:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

Lys Lys Thr Leu
1

(2) INFORMATION FOR SEQ ID NO:26:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

Ser Gly Ser Gly Ser Gly Leu Pro Leu Phe
1               5                   10
```

METHODS AND COMPOSITIONS FOR ENHANCING CELLULAR RESPONSE TO TGF-β LIGANDS

CROSS-REFERENCE TO RELATED APPLICATION

The present application claims benefit of the filing date of U.S. Provisional Appl. No. 60/012,054, filed Feb. 22, 1996, which disclosure is herein incorporated by reference.

Part of the work performed during development of this invention utilized U.S. Government funds. The U.S. Government has certain rights in this invention.

FIELD OF THE INVENTION

The present invention relates to the TGF-β receptor-mediated signaling pathway.

BACKGROUND OF THE INVENTION

The Transforming Growth Factor-beta (TGF-β) family consists of many structurally related small peptides, which regulate a wide range of crucial cell growth and differentiation events, including early embryonic patterning and morphogenesis, sexual organ and bone/cartilage formation, wound healing and immunosuppression. Disregulation of these events has been implicated in a variety of diseases including tumorigenesis (Massagué, J. et al., *Trends in Cell Biology* 4:172–178 (1994); Kingsley, D. M., *Genes Dev.* 8:133–146 (1994); Roberts, A. B. and Sporn, M. B., *Growth Factors* 8:1–9 (1993); Attisano, L. et al., *Biochim. Biophys. Acta.* 1222:71–80 (1994); Moses, H. L. et al., *Cell* 63:245–247 (1990); Border, W. A. and Ruoslahti, E. J., *J Clin. Invest.* 90:1–7 (1992)). However, the molecular mechanisms involved in these processes are not fully defined.

Recent progress in the cloning and characterization of the cell surface receptors for each member of the family yielded two new groups of receptors, the type I and type II, which consist of homologous single transmembrane serine/threonine kinases (for reviews, see Massague, J. et al., *Trends in Cell Biology* 4:172–178 (1994); Derynck, R., TIBS:548–553 (1994); Mathews, L. S., *Endocr. Rev.* 15:310–324 (1994); Heldin, C.-H., *Cell* 80:213–223 (1995)). Unlike most of the growth stimulatory factors, which mediate their cellular effects through homodimeric complexes of tyrosine kinase receptors (for reviews, see Schlessinger, J. and Ulrich, A., *Neuron* 9:383–391 (1992); Heldin, C.-H., *Cell* 80:213–223 (1995)), TGF-β family members require heteromeric complexes of both type I and type II serine/threonine kinase receptors for signaling (reviewed by Massagué, J. et al., *Trends in Cell Biology* 4:172–178 (1994); Heldin, C.-H., *Cell* 80:213–223 (1995)). Molecular characterization of the type I and the type II receptors of the prototypical TGF-β revealed that the two types of receptors play different roles in mediating downstream signaling. Type II is a constitutively active serine/threonine kinase receptor which can bind TGF-β independently, but cannot signal without the type I receptor (Laiho, M. et al., *Cell* 62:175–185 (1990); Wrana, J. L. et al., *Cell* 71:1003–1014 (1992)); while the type I receptor cannot bind to TGF-β in the absence of the type II receptor, is inactive as a kinase on its own, but is likely activated by the type II receptor upon ligand binding (Wrana, J. L. et al., *Nature* 370:341–47 (1994); Ebner, R. et al., *Science* 260:1344–1348 (1993)). The recent discovery of a mutant type I receptor with a constitutively active kinase, able to signal in the absence of the type II receptor and TGF-β, suggests that the type I receptor is responsible for initiating the downstream signaling pathway subsequent to its activation by the type II receptor (Wieser, R. et al., *EMBO J.* 14:2199–2208 (1995)).

Little is known about how the type II receptor activates the type I receptor. Upon TGF-β binding, the type II receptor forms heteromeric complexes with the type I receptor and phosphorylates the type I receptor (Wrana, J. L. et al., *Nature* 370:341–47 (1994)). Although all phosphorylation sites on the type I receptor have not yet been mapped, a serine/threonine rich domain located immediately amino-terminus to the kinase domain of the type I receptor (the GS box) was found to be phosphorylated (Wrana, J. L. et al., *Nature* 370:341–47 (1994); Wrana, J. L. et al., *Mol. Cell. Biol.* 14:944–950 (1994)). Type II receptor-mediated type I receptor phosphorylation can activate the type I receptor through two possible mechanisms: 1) by creating binding sites for activators or abolishing binding sites for inhibitors or, 2) by simply inducing a conformational change of the type I receptor, which could either directly activate the kinase activity or indirectly activate the kinase activity by releasing an inhibitor. To fully understand the molecular details involved in the activation of the type I receptor, it is therefore essential to identify and characterize the cytoplasmic interactors of the type I receptors before and after ligand binding.

The immunophilin FKBP12 has been reported as a specific cytoplasmic interactor of one member of the TGF-β receptor family (Wang, T. W. et al., *Science* 265:674–676 (1994)). FKBP12 is known to mediate the immunosuppressive activities of two macrolides, FK506 and rapamycin, by binding to the macrolides and then recruiting and thereby inactivating the serine/threonine phosphatase calcineurin and the serine kinase FRAP (or RAFT1) respectively, resulting in the blockage of the signaling pathways mediated by calcineurin or FRAP (Siekierka, J. J. et al., *Nature* 341:755–777 (1989); Harding, M. W. et al., *Nature* 341:758–760 (1989); Bierer, B. E. et al., *Proc. Natl. Acad. Sci.* 87:9231–9235 (1990); Liu, J. et al., *Cell* 66:807–815 (1991); Liu, J. et al., *Biochemistry* 31:3896–3901 (1992); Clipstone, N. A. and Crabtree, G. R., *Nature* 357:695–697 (1992); O'Keefe, S. J. et al., *Nature* 357:692–694 (1992); Jain, J. et al., *Nature* 365:352–355 (1993); McCaffrey, P. G. et al., *Chem.* 268:3747–3752 (1993); Brown, E. J. et al., *Nature* 369:756–758 (1994); Sabatini, D. M. et al., *Cell* 78;35–43 (1994); Zheng, X.-F. et al., *Cell* 82:121–130 (1995); Brown, E. J. et al., *Nature* 377:441–446 (1995)). In the absence of the macrolides, however, FKBP12 cannot interact with either enzyme. Since high levels of FKBP12 are found in virtually all mammalian cell types and it is also highly conserved from plants to mammals, its physiological role is likely to be very important. Clearly, there is a need for further elucidation of the role FKBP12 plays in the TGF-β receptor-mediated signaling pathway.

SUMMARY OF THE INVENTION

FKBP12 is an evolutionary conserved, abundant cytoplasmic protein which is known to mediate the immunosuppressive effects of the macrolides FK506 and rapamycin. The present inventors have discovered that FKBP12 is a common cytoplasmic interactor of the Transforming Growth Factor-beta (TGF-β) receptor family and, surprisingly, acts as an inhibitor of the TGF-β receptor-mediated signaling pathway. By the invention, the inventors have further discovered that macrolide potentiators can block FKBP12 binding to the TGF-β type 1 receptors and thereby enhance the cellular effects elicited by the TGF-β ligands.

The TGF-β ligands are known to elicit a number of cellular responses, including inhibition of cell proliferation, stimulation of connective and supporting tissue formation, inhibition and activation of FSH secretion by pituitary cells, induction of ectopic cartilage formation, localization of the vegetal pole of eggs, dorsal-ventral axis formation, and morphogenesis of the imaginal disks. Because of such cellular responses, the TGF-β ligands have several clinical applications including promoting bone and cartilage formation, preventing or retarding the formation of scar tissue caused by ocular trauma, promoting tissue growth for wound healing, treating multiple sclerosis, treating ulcers, removing dead burn tissue, treating psoriasis, and inhibiting growth of gynecological tumors and ocular melanoma.

Thus, by the invention, a method is provided for potentiating a cellular response elicited by a TGF-β ligand. The method involves administering to cells which express a TGF-β receptor an effective amount of a macrolide potentiator to enhance the cellular response to the TGF-β ligand, wherein the macrolide potentiator enhances the cellular response by binding to FKBP12. Preferably, the macrolide potentiator is FK506 or a naturally occurring or synthetic FK506 derivative capable of binding to FKBP12. More preferably, the FK506 derivative is a FK506 antagonist which lacks or has reduced immunosuppressive activity and has little toxicity in mammals. Example macrolide potentiators according to the present invention are 15-O-desmethyl-FK520 and L-685,818.

By the invention, one or more macrolide potentiators can be administered to cells either before, after, or simultaneously with an effective amount of the TGF-β ligand. TGF-β family type I receptors include R1, R2, R3, R4, ALK3, ALK6, Sax, and Tkv. Cells which express such receptors and which have a potent response to a TGF-β ligand include lymphocytes, fibroblasts, macrophages, synovial cells, and epithelial cells (both normal and malignant). The TGF-β ligand family members include, (1) the closely related members: TGF-β1, TGF-β2, TGF-β3, TGF-β4, and TGF-β5; and (2) those members that are more distantly related to TGF-β1: Müllerian Inhibiting Substance (MIS), the α, βA, and βB chains of the inhibins and activins, the bone morphogenetic proteins 2a, 2b, and 3, the Vgr-1 gene product, the decapentaplegic (DPP) gene product, and growth differentiation factors-1–9 (GDFs1–9).

The present invention further provides a pharmaceutical composition comprising a macrolide potentiator, a TGF-β ligand, and a pharmaceutically acceptable carrier or excipient.

Also provided is a screening method for determining whether a macrolide is a potentiator of TGF-β ligand activity. The method involves contacting cells which express a TGF-β receptor with a macrolide and a TGF-β ligand, assaying a cellular response, comparing the cellular response to a standard cellular response, the standard being assayed when contact is made with the TGF-β ligand in the absence of the macrolide, whereby an enhanced cellular response over the standard indicates that the macrolide is a potentiator of TGF-β ligand activity. By the invention, an enhanced cellular response occurs if there is an increase or decrease in cell number over the standard. The cellular response can be measured using any known in vitro or in vivo system, including the MIS organ culture assay and the mink lung epithelial cell transcriptional response or antiproliferative assays.

BRIEF DESCRIPTION OF THE FIGURES

FIG. 1. Specific interaction between TGF-β family type I receptors and FKBP12, and mapping the FKBP12 binding domains of a type I receptor (R1).

FIG. 1B. A yeast selective plate (Ura$^-$ His$^-$ Trp$^-$ galactose plate with X-Gal) containing yeast colonies expressing two fusion proteins: B42 fusion protein of FKBP12 and LexA fusion proteins of R1C mutants as labeled. FIG. 1C A schematic diagram of the deletions and mutations on the cytoplasmic domain of R1, with their FKBP12 binding activities indicated. The entire cytoplasmic domain of R1 (R1C) consists of the juxtamembrane region (JM, a.a. 147–209), the kinase region (K, a.a. 210–499) and the tail region (T, a.a. 500–509). The JM region contains the GS box (a.a. 179–209), as indicated. The filled box represents the core sequence of the GS box. The proline (bold letter) in the GS box is marked with a star. The interaction activities of each receptor mutant were rated according to the intensity of the blue color of their transformants in FIG. 1A. RICK$^-$, the full length R1C with a point mutation within the ATP binding site of the kinase domain (V222R); JMΔK, R1C with deletion of the tail and the last 17 amino acids of the kinase domain; (+GS)KT, R1C with deletion of the JM region amino-terminus to the GS core; (–GS+p)KT, R1C with deletion of the JM region including the GS core sequence amino-terminus to leucine; (–GS–p)KT, R1C with further deletion of leucine and proline; j, k, l are same as g, h, i, respectively, except with an extra deletion of the tail; m, n are same as g, d respectively, except with serine (187) and threonine (189) mutated into alanines; o, a FKBP12 mutant (D37G) defective in binding to FK506 and rapamycin was fused with B42 and tested for interaction with LexA fusion of R1C.

FIG. 2. Interaction between FKBP12 and ligand-free TGF-β type I receptor (R4) in COS cells.

Figure 3A:
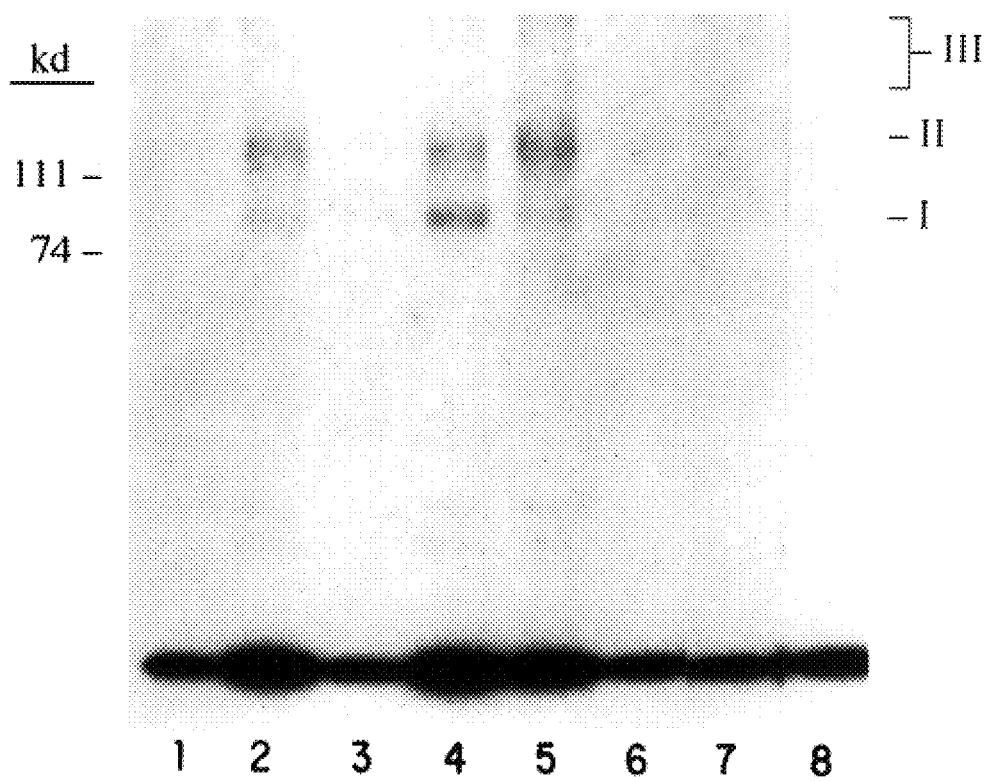
FIG. 3. FKBP12 is released from the ligand-bound TGF-β type I receptor. COS1 cells transiently transfected with the indicated cDNAs in pCMV6 or pCMV6 vector alone (EV)
Figure 3B:
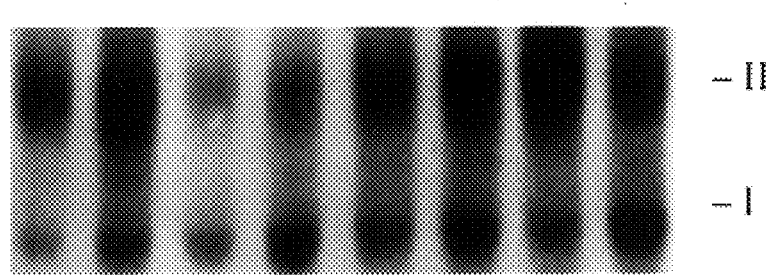

were affinity labeled two days after transfection by incubation with [$^{125}$I]-TGF-β followed by disuccinimidyl suberate. Cells were lysed in 500 μl of lysis buffer. The cell lysates (200 μl) were used for immunoprecipitation using anti-T7 monoclonal antibody in the absence (lanes 1–7) or presence (lane 8) of 3 μg of T7 peptide. The immunoprecipitates were then separated on 10% SDS-PAGE, which was then subjected to autoradiography for 6 days (FIG. 3A). Cell lysates (50 μl) were also directly subjected to 10% SDS-PAGE and autoradiography for 48 hours (FIG. 3B).

FIG. 4. Non-functional derivatives of FK506 can compete with the TGF-β type I receptor in binding to FKBP12 and thus enhance TGF-β effects on Mv1Lu cells.

Figure 4A:
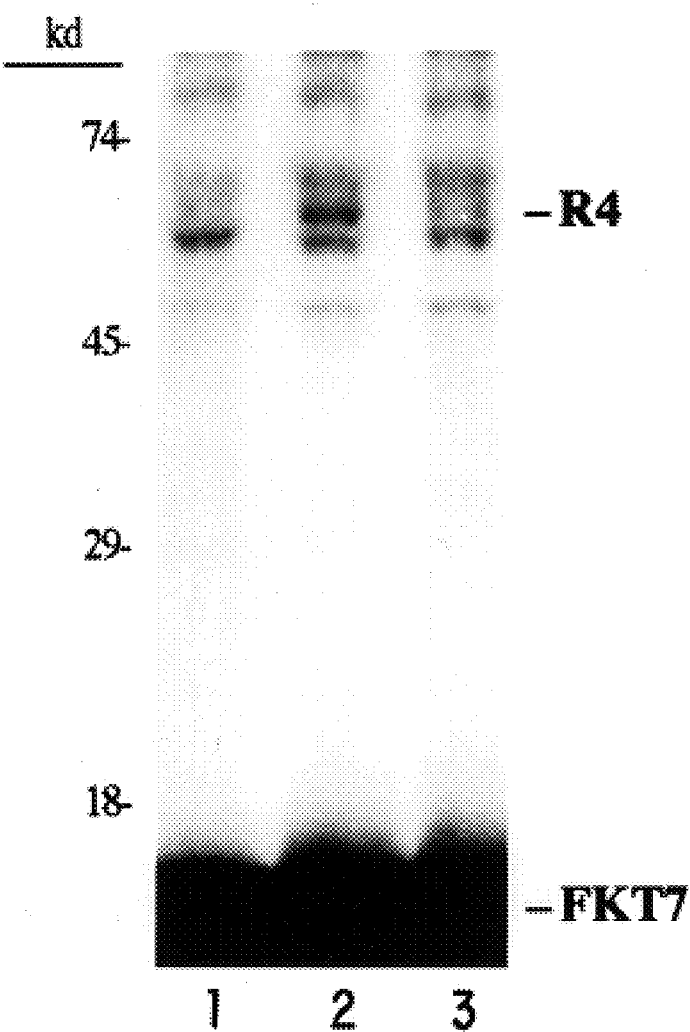

FIG. 4A. Competition of L685,818 with R4 in binding to FKBP12 in COS cells. COS1 cells transfected with the indicated cDNAs in either pCMV8 (FKT7) or pCMV6 (R4) or pCMV6 vector alone (EV) were treated with or without L685,818 and metabolically labeled with [$^{35}$S]-methionine. Cells were then lysed, and cell lysates were subjected to immunoprecipitation using anti-T7 monoclonal antibody. The immunoprecipitates were separated on 15% SDS-PAGE, which was then subjected to autoradiography.

Figure 4B:
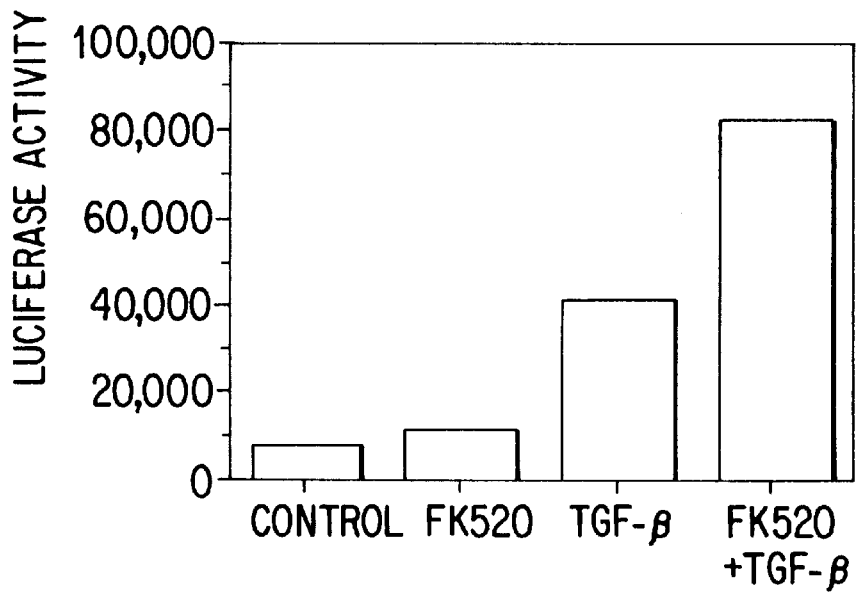
Figure 4C:
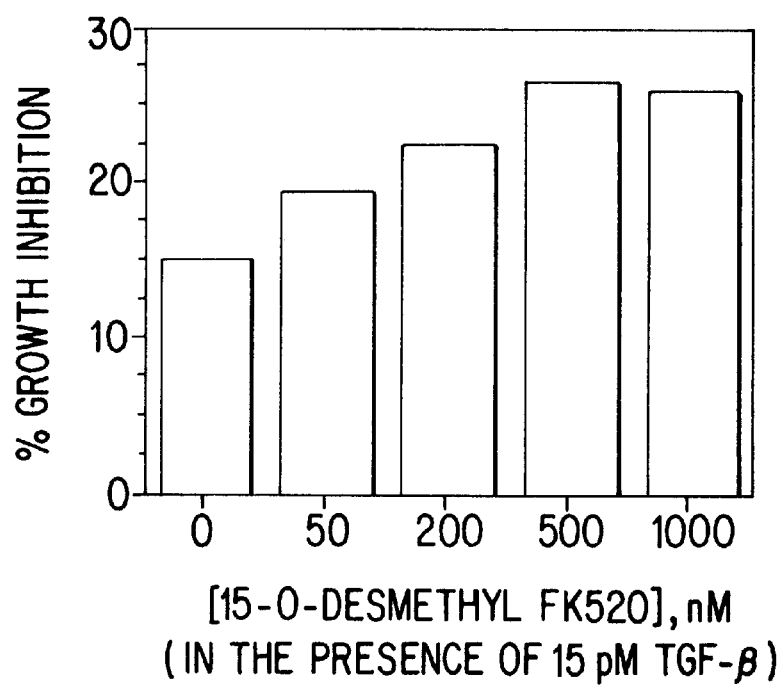

FIGS. 4A and 4B. Enhancement of the TGF-β induced gene response (FIG. 4B) or growth inhibition (FIG. 4C) in Mv1Lu cells by 15-O-desmethyl-FK520. FIG. 4B Mv1Lu cells transfected with p3TP-Lux reporter construct (control) were incubated with 200 nM 15-O-desmethyl-FK520 alone (FK520), or 200 pM TGF-β alone, or 200 nM 15-O-desmethyl-FK520 together with 200 pM TGF-β (FK520+ TGF-β). Luciferase activity was measured in cell lysates; FIG. 4C Mv1Lu cells were incubated with increasing concentrations of 15-O-desmethyl-FK520, as indicated for two hours and then treated with or without 15 pM TGF-β for 40 hours in the presence of 15-O-desmethyl-FK520. Cell numbers were determined in Coulter counter. The data shows the percent of decrease in cell numbers upon TGF-β treatment.

FIG. 5. MIS mediated Müllerian duct regression enhanced by 15-O-desmethyl-FK520.

Figure 5A:
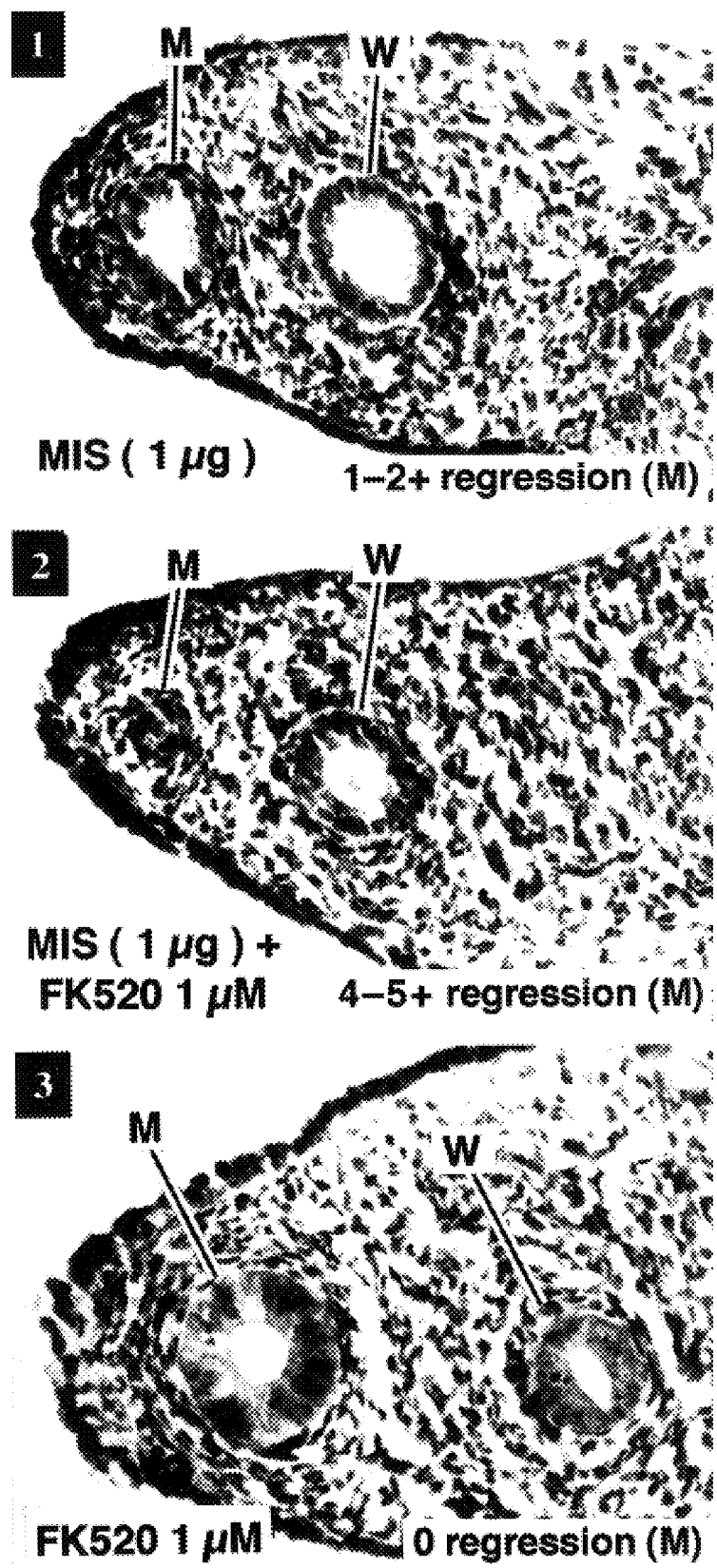

FIG. 5A Hematoxylin and eosin stained paraffin sections of urogenital ridges from the organ culture. The dissected 14½ day female rat urogenital ridges containing the Wolffian duct (W) and the Müllerian duct (M) were subjected to the organ culture assay in the presence of either 1 μg MIS (top panel), or 1 μM 15-O-desmethyl-FK520 (bottom panel), or 1 μg MIS and 1 μM 15-O-desmethyl-FK520 (middle panel). Regression of the Müllerian duct was graded as described (Donahoe, P. K. et al., *J. Surg. Res.* 23:141–148 (1977)). Three groups of urogenital ridges were tested and yielded similar results.

Figure 5B:
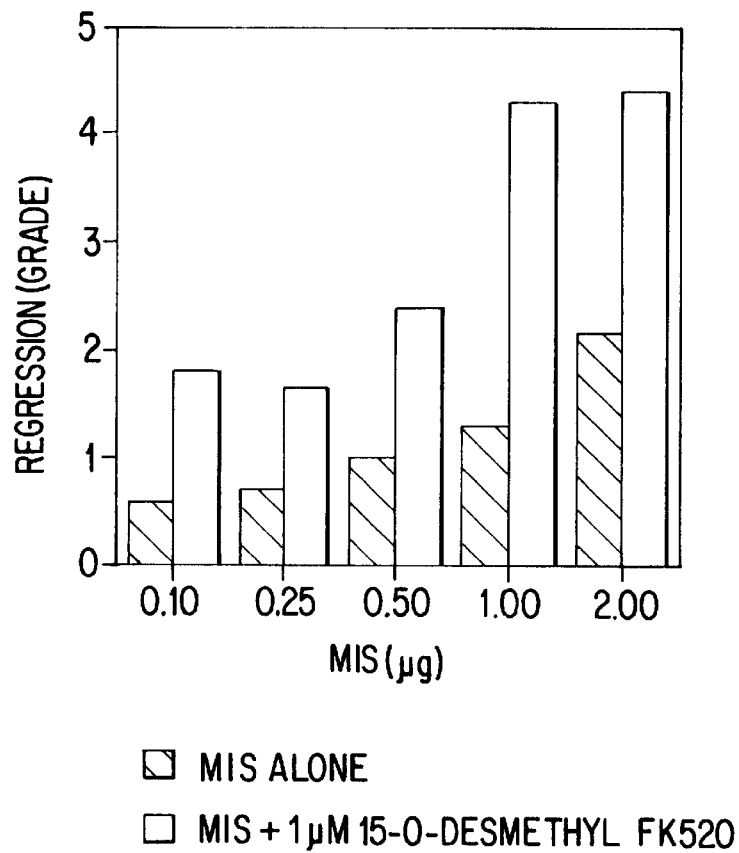

FIG. 5B Regression activities of different doses of MIS in the presence or absence of 1 μM 15-O-desmethyl-FK520. Each number of the regression grades shown are averages of grades of three tested urogenital ridges.

Figure 5C:
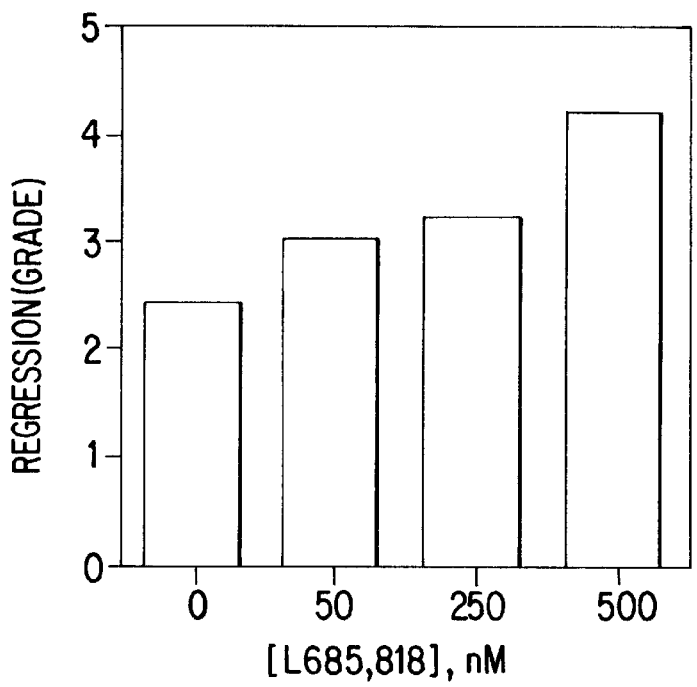

FIG. 5C Regression activities of 2 μg MIS in the presence of different doses of L685,818.

FIG. 6. A model for FKBP12 binding to the inactive TGF-β type I receptor and the activation of the TGF-β type I receptor upon the release of FKBP12.

Figure 6A:
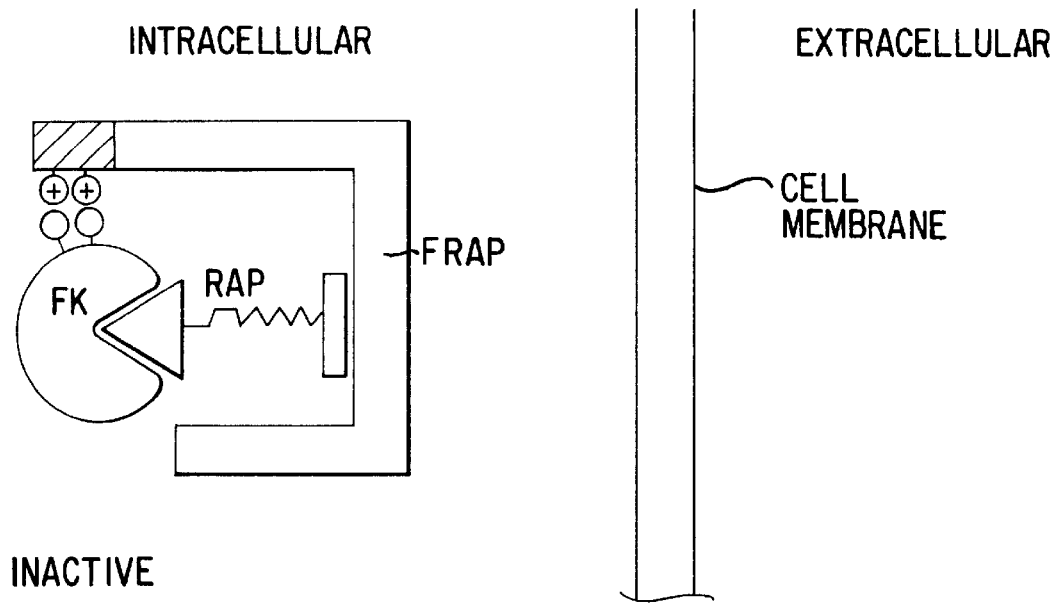

FIG. 6A A schematic of the FKBP12/rapamycin/FRAP ternary complex based upon the X-ray crystallography of the complex. Two domains of rapamycin, one interacts with FKBP12, the other interacts with FRAP. There is almost no direct interaction between FKBP12 and FRAP, except two positively charged amino acids on both proteins facing each other.

Figure 6B:
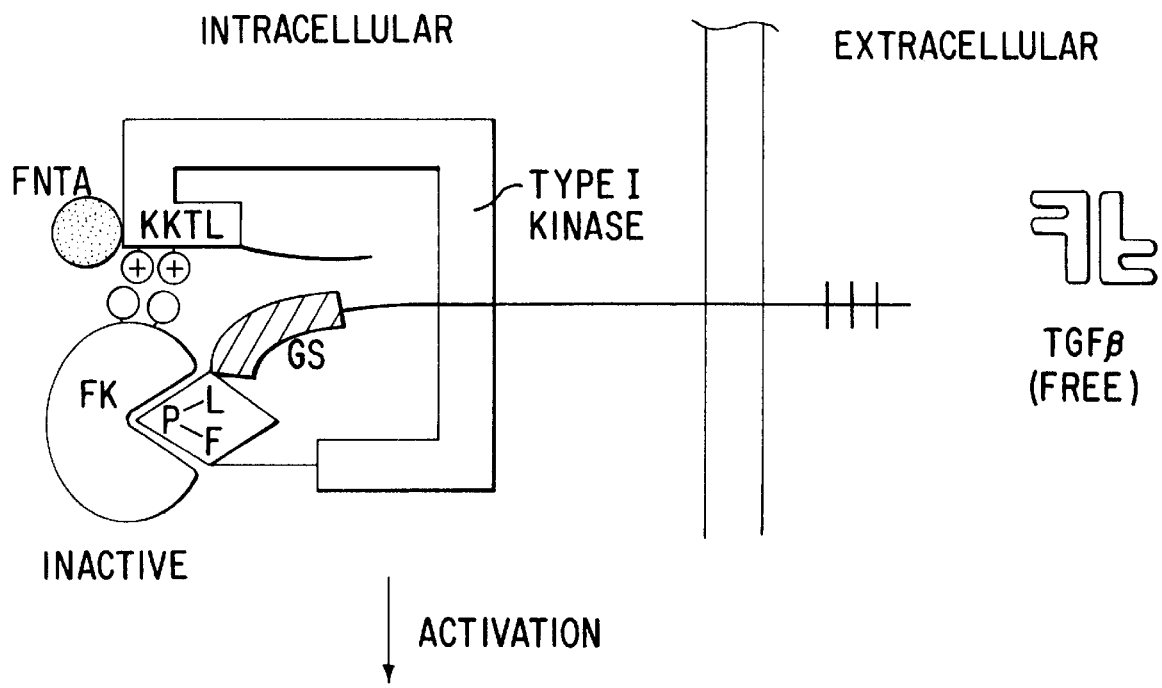

FIG. 6B A schematic of the FKBP12/type I receptor complex based upon the deletion and mutation studies described in the text.

FIG. 6C A model for the activation of the TGF-β type I receptor upon ligand-induced FKBP12 release. Type II receptor complexes with and phosphorylates the type I receptor upon ligand binding, and thus releases FKBP12 and FNTA, the latter of which is phosphorylated. A third cytoplasmic interactor specific for the phosphorylated GS domain is proposed here. This interactor could be subjected to phosphorylation by the activated type I receptor kinase. Its subsequent release after phosphorylation is also proposed.

FIG. 7. FKBP12 interacts with type I receptors through its amino terminus region.

FIG. 7A Protein and nucleotide sequence for the Drosophila FKBP12 (SEQ ID NO:1 and SEQ ID NO:2).

Figure 7B:
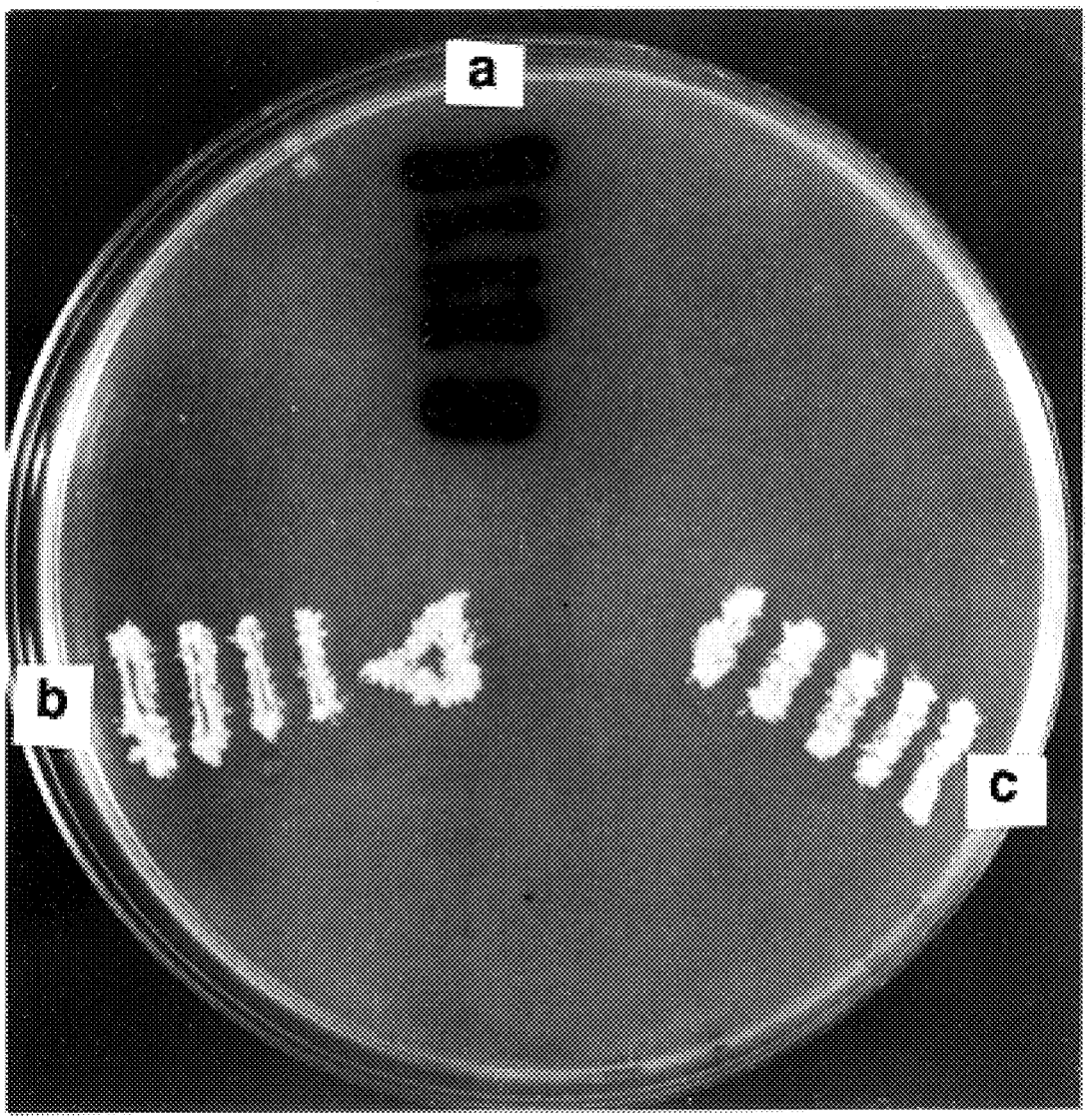

FIG. 7B Mapping FKBP12 domain responsible for receptor binding. The cytoplasmic domain of TGF-β type I receptor (R4C) subcloned in PEG202 (LexA-R4C) was transformed into yeast. The transformed yeast was again transformed with (a) B42-FKBP12, (b) B42-(Δ5)FKBP12, and (c) an unrelated negative control. The transformants were tested for interaction on a galactose plate with X-Gal.

FIG. 7C Protein sequence alignment of different FK506 binding proteins using "Pretty Box" (SEQ ID NOS:3–7).

Figure 8:
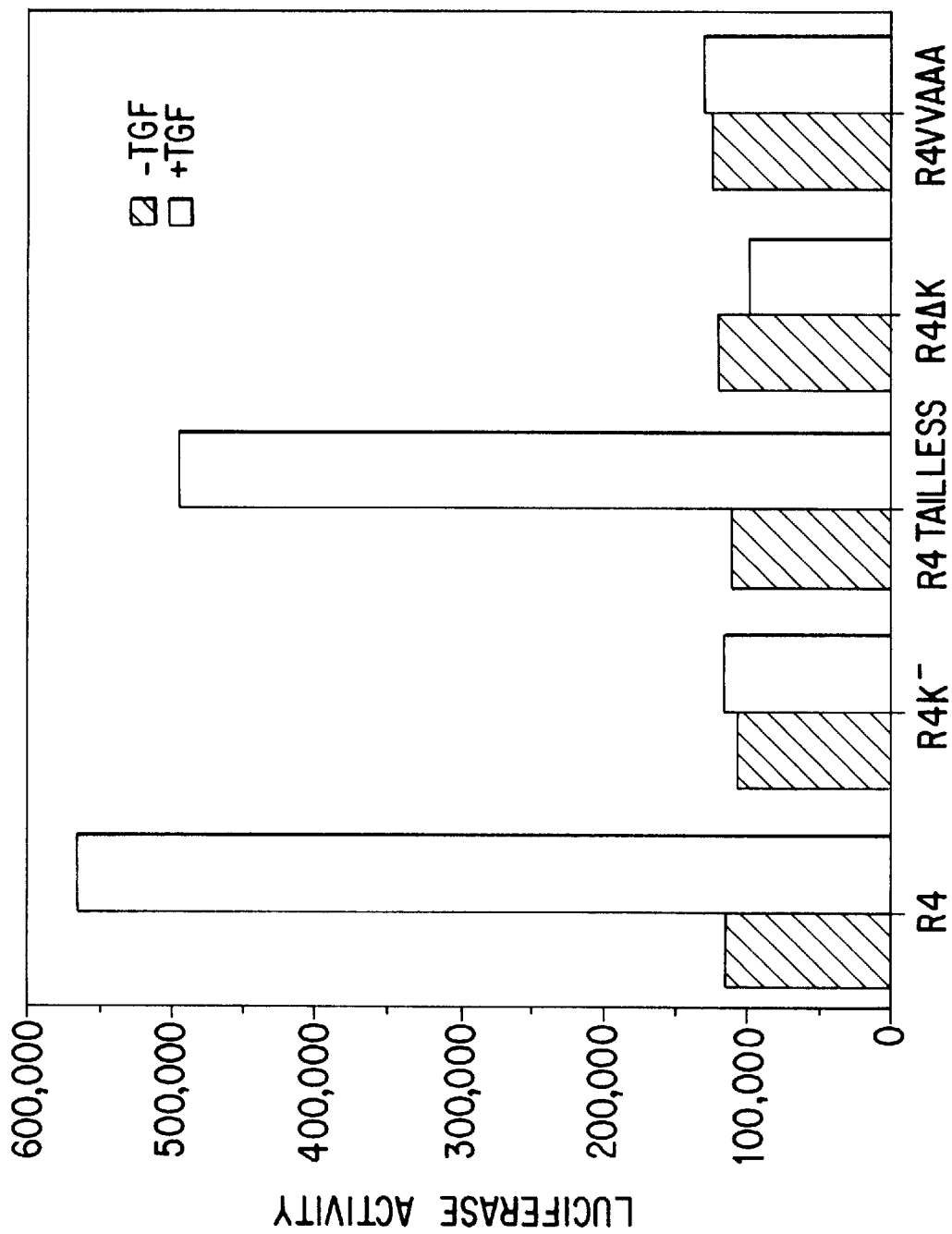

FIG. 8. Signaling activities of R4 and R4 mutants in a mutant Mv1Lu cell line (R1B). R4 or R4 mutants were tested for their ability to restore the TGF-β dependent gene response in R1B cells. R1B cells were transiently transfected with p3TP-lux reporter construct and the indicated wild type R4 or mutant R4 in pCMV6 vector. Cells were then incubated for 20 hr in the presence or absence of 250 pM TGF-β, and luciferase activity was measured in cell lysates. Each assay was carried out twice and each sample in triplicate. R4: R4 in pCMV6; R4K$^-$: R4 kinase deficient mutant (K230R) in pCMV6; R4 tailless: R4 mutant lacking the last six amino acids of the carboxyl-terminus tail in pCMV6; R4ΔK: R4 mutant lacking the last 23 amino acids of the carboxyl-terminus including the tail and a short region of the kinase domain; R4VVAAA: R4 with threonine to valine, serine to alanine mutations within the GS core sequence TTSGSGSG.

Figures 9A, 9B:
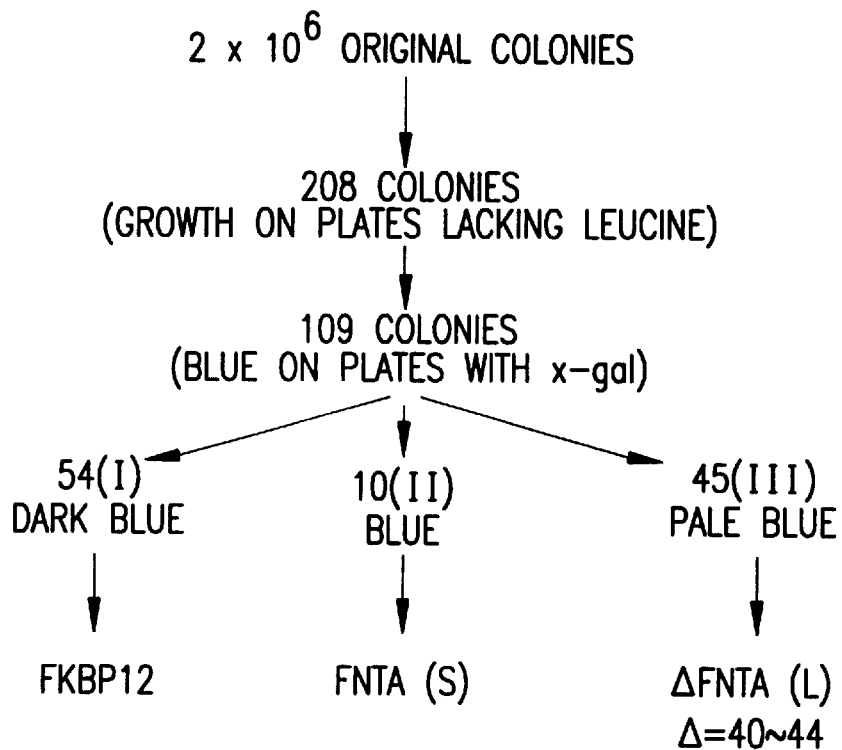
Figure 10A:
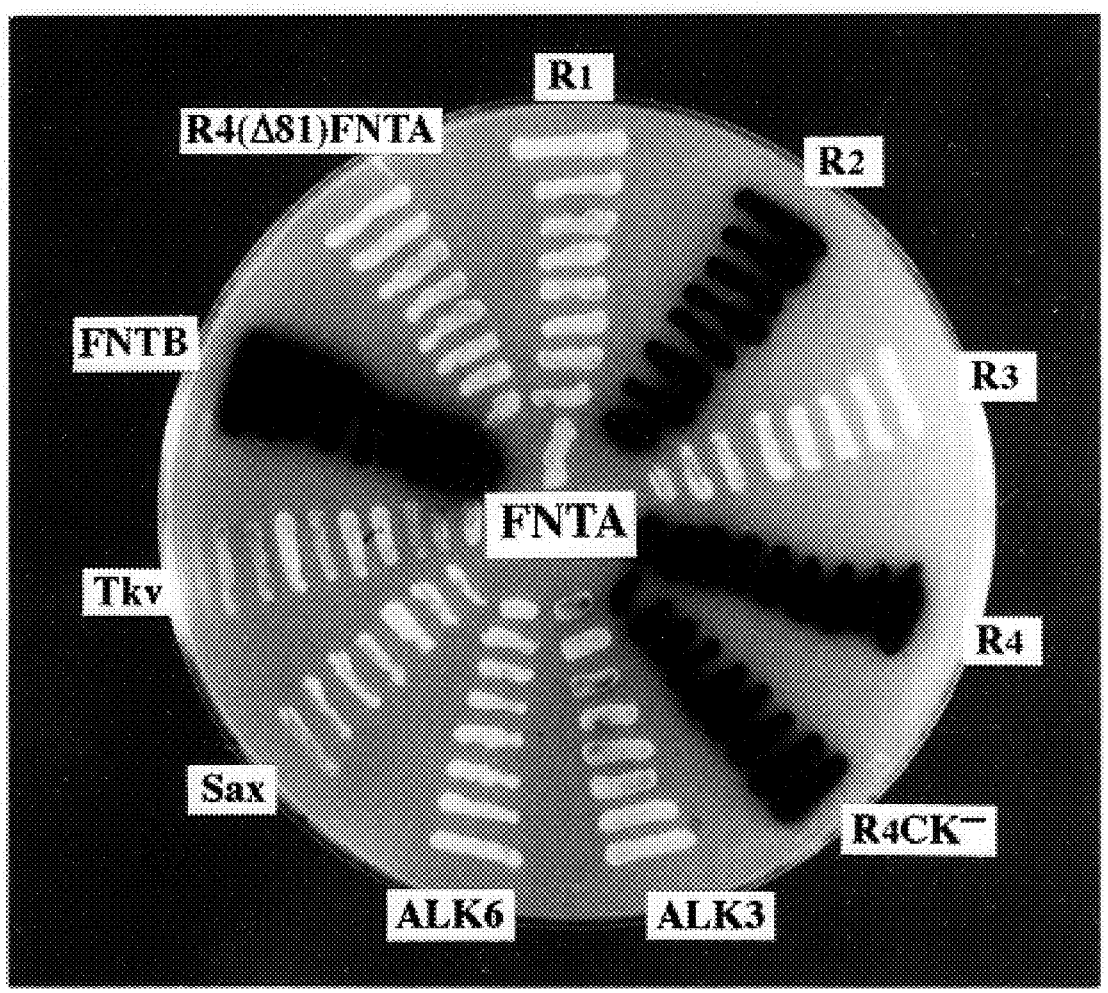
Figure 10B:
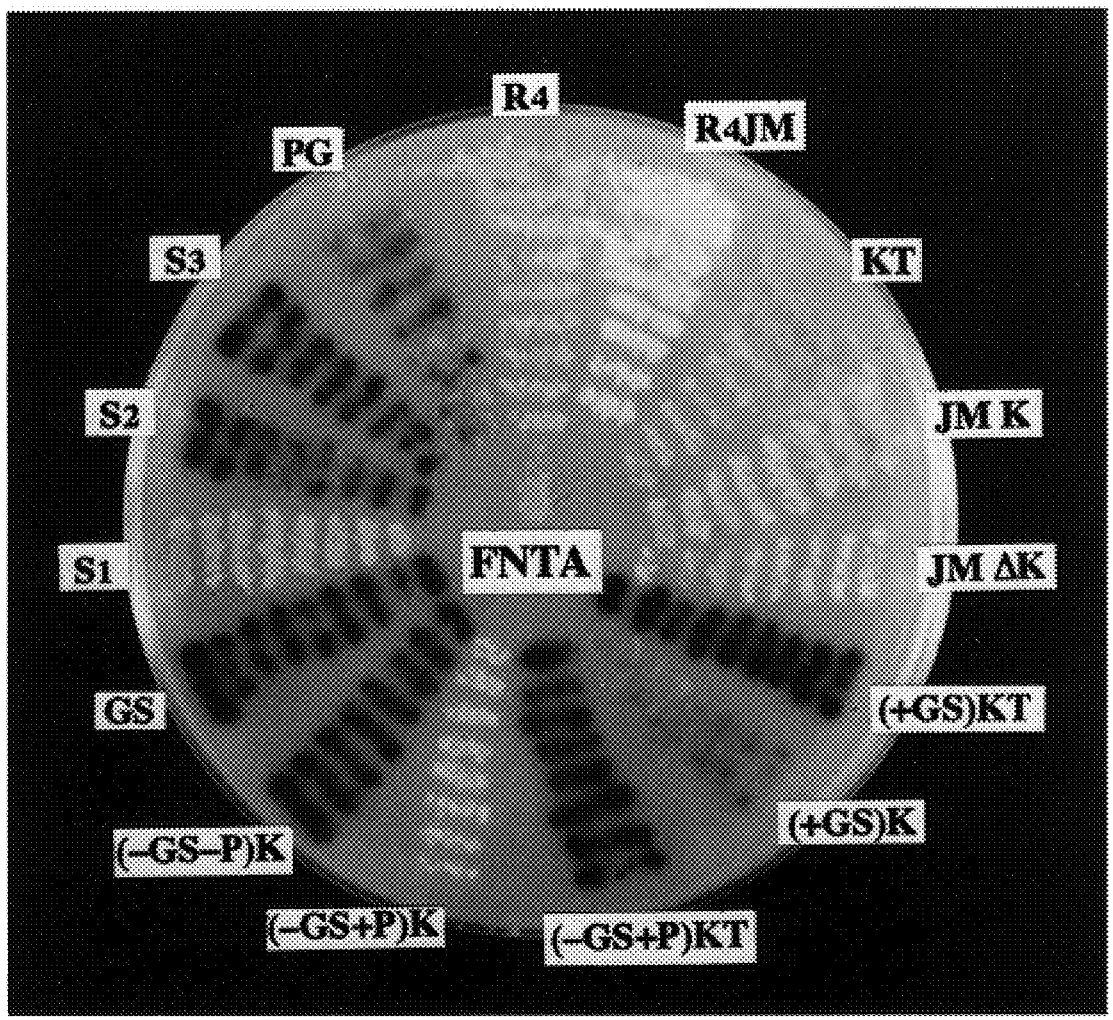
Figure 10C:
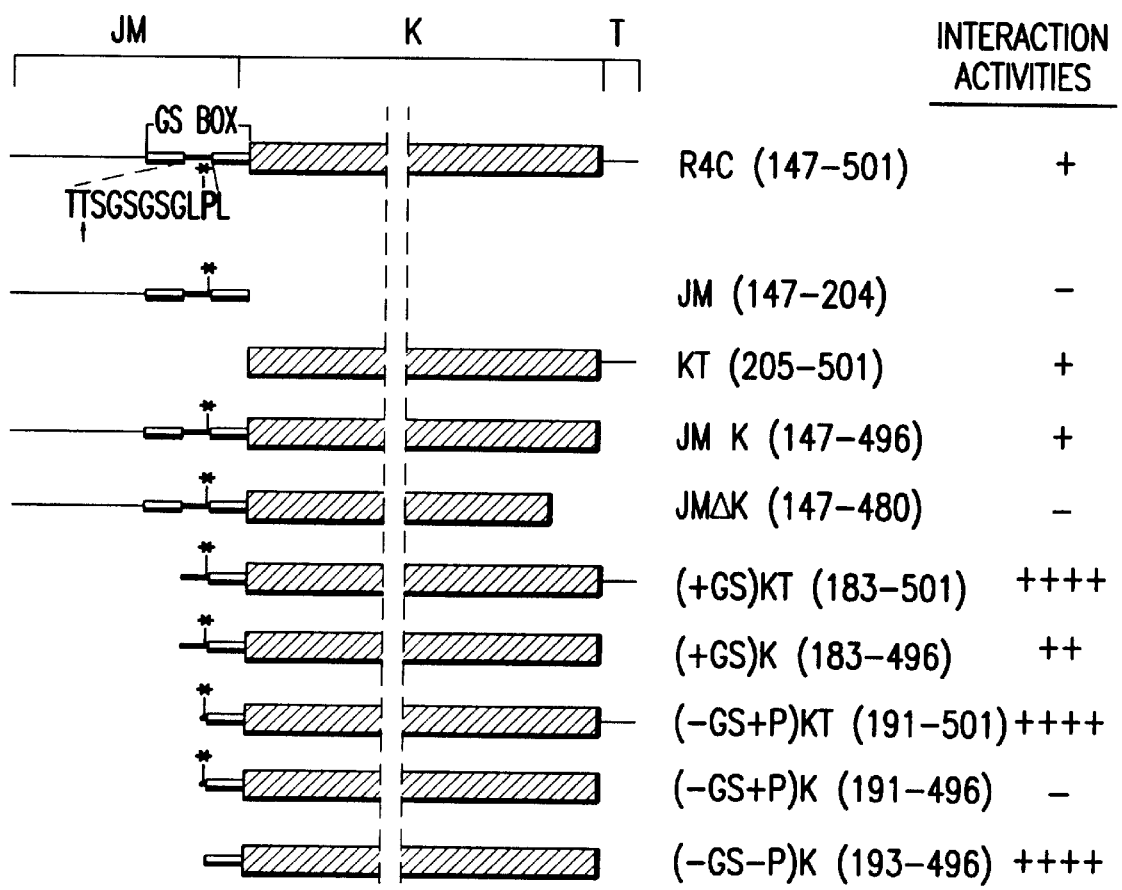
Figure 10D:
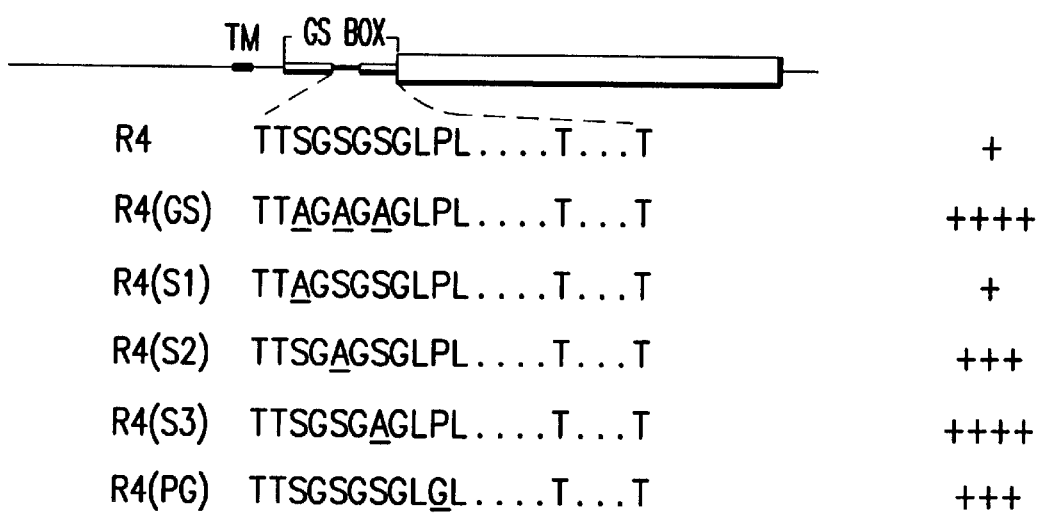

FIG. 9. Identification of cytoplasmic interactors of the TGF-β type I receptor (R4) using a modified yeast two hybrid system (Zervos, A. S. et al., *Cell* 72:223 (1993), Wang, T. W. et al., *Science* 265:674 (1994)). A. Summary of the library screening. The entire cytoplasmic domain of R4 was fused in-frame to the carboxyl-terminus of the DNA binding domain of LexA to serve as the bait (Wang, T. W. et al., *Science* 265:674 (1994)). A human fetal brain cDNA library in the yeast expression vector pJG4-5 was used in the library screening. FIG. 9B. Difference of the nucleotide sequences and their encoded amino acid sequences of the two isolated FNTA cDNAs (SEQ ID NOS:8–11).

FIG. 10. Test of FNTA interaction with multiple known type I receptors and mapping of the interaction domains on R4. FIG. 10A. LexA fusion proteins of the cytoplasmic domains of different type I receptors (Franzen, P. et al., *Cell* 75:681 (1993); Bassing, C. H. et al., *Science* 264:87 (1994); He, W. W. et al., *Dev. Dynam.* 196:133 (1993); ten Dijke, P. et al., *Oncogene* 8:2879 (1993); ten Dijke, P. et al., *Science* 264:101 (1994); Brummel, T. J. et al., *Cell* 78:251 (1994); Xie, T. et al., *Science* 263:1756 (1994)) and FNTB (Andres, D. A. et al., *Genomics* 18:105 (1993)), as indicated at the side of the yeast plate, were tested for interaction with B42-FNTA. LexA-R4C was also tested for interaction with B42-Δ81FNTA (amino-terminus 81 amino acids of FNTA deleted). All fusion constructs were made by PCR and subcloning, as described previously (Wang, T. W. et al., Science 265:674 (1994)). Nine to ten individual colonies of yeast transformants were streaked onto a fresh Ura⁻His⁻Trp⁻glucose plate, replica plated onto both glucose and galactose Ura⁻His⁻Trp⁻ plates with X-gal, and incubated at 37° C. for 72 hours. Only the galactose plates are shown here. FIG. 10B. LexA fusion proteins of R4 deletions and mutations, as indicated at the side of the yeast plate, were tested for interaction with B42-FNTA as described in A. To show the different interaction affinities of R4 mutants the galactose X-gal plates were incubated at 37° C. for 12 hours. FIG. 10C. Schematic drawings of the R4 deletions and summaries of their interaction activities. The core sequence of the GS box (filled box) and the proline residue (asterisk) are indicated. FIG. 10D. Schematic drawings of R4 mutations within the GS box and summaries of their interaction affinities (SEQ ID NOS:12–17).

Figure 11:
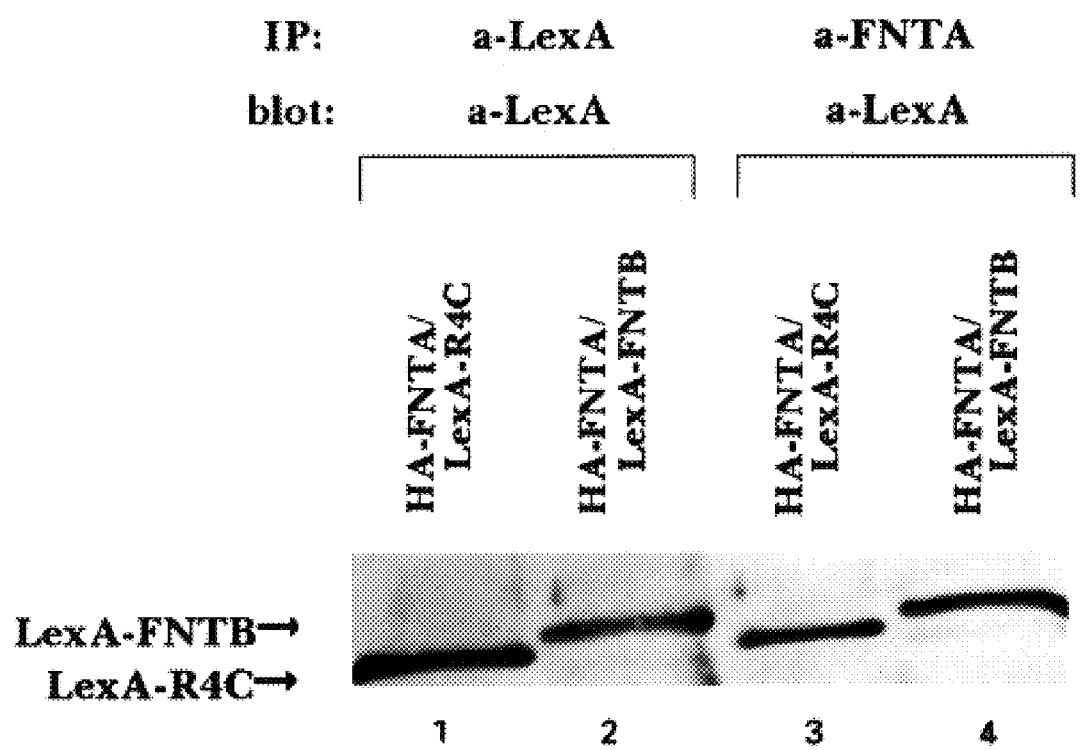

FIG. 11. Co-immunoprecipitation of FNTA (the short variant) and the cytoplasmic domain of R4 from yeast cell lysates. Yeast co-expressing either HA tagged B42-FNTA (HA-FNTA) and LexA-R4C, or HA-FNTA and LexA-FNTB, as indicated, were lysed in lysis buffer (20 mM Tris-HCl at pH 7.4, 150 mM NaCl, 0.5% Triton X-100) with 1 mM PMSF. The obtained cell lysates were immunoprecipitated with either anti-LexA (lane 1, 2) or anti-FNTA antibody (lane 3, 4) and the precipitated proteins were analyzed by Western blot using anti-LexA antibody.

FIG. 12. FNTA/R4 interaction, FNTA phosphorylation and functional significance of the interaction. FIGS. 12A and 12B. FNTA binds to ligand-free R4. The histidine-tag was attached to the amino-terminus of FNTA and FKBP12 by PCR and subcloned into pCMV6 vectors. COS cells transiently transfected with the indicated constructs were lysed followed by absorption of histidine-tagged proteins with $Ni^{2+}$ charged beads as described (Cohen, G. B. et al., Cell 80:237 (1995); Pawson, T., Nature 373:573–580 (1995); Heldin, C.-H., Cell 80:213 (1995)). The co-precipitated R4 or FNTB were analyzed by Western blot, using either purified anti-R4 (FIG. 12A) or anti-FNTB antiserum (FIG. 12B), respectively. Cell lysates before histidine bead absorption and proteins eluted from the $Ni^{2+}$ charged beads are indicated by "L" (lysates) and "B" (beads), respectively; EV, empty pCMV6 vector; FN-his, histidine tagged FNTA; FK-his, histidine tagged FKBP12, which serves as a positive control for FNTA binding to R4, and a negative control for FNTA binding to FNTB. FIG. 12C. Co-precipitation of FNTA with ligand-bound R4 in the presence of kinase deficient, but not wild type II receptor. COS cells transfected with the indicated wild type or mutant type I and type II receptors (R4K⁻=R4K230R; RIIK⁻=RII K277R) together with FNTA in pCMV6 vector (lanes 3–5), or with the empty pCMV6 vector (EV, lane 6), which serves as a negative control, were affinity labeled with $^{125}$I-TGF-β by chemical cross-linking as described (Cheifez, S. et al., J. Biol. Chem. 261:9972 (1986)), lysed and immunoprecipitated with 10 μl of monoclonal anti-FNTA antibody. The co-precipitated type I/type II receptor complexes were eluted from the protein A sepharose beads, separated on a 10% SDS PAGE, which was dried and subjected to autoradiography for 72 hours (lanes 3–6). Total cell lysates from $^{125}$I-TGF-β affinity labeled wild type mink lung epithelial cells and its type I receptor deficient mutant R1B cell line (Laiho, M. et al., J. Biol. Chem. 9:108 (1991)) were also separated on the gel to show the migration patterns of the three types of $^{125}$I-TGF-β labeled receptors (lanes 1 & 2). FIGS. 12D and 12E. Phosphorylation of FNTA in transfected COS cells or in untransfected wild type Mv1Lu cells. COS cells transfected with the indicated constructs, or untransfected Mv1Lu cells were labeled with $^{32}$P-pyrophosphate as described previously (Wrana, J. L. et al., Nature 370:341 (1994); Wieser, J. et al., EMBO 14:2199 (1995)), lysed and immunoprecipitated with anti-FNTA monoclonal antibody, and analyzed by autoradiography (48 hours). TGF-β (100 pM) was added into all transfected COS cells and the Mv1Lu cells in lane 2 (FIG. 12E), but not in lane 1 (E). FIG. 12F. The signaling defect of R4ΔK. Wild type R4 and two R4 mutants, R4tailless and R4ΔK, were transiently-transfected with the TGF-β responsive 3TPlux reporter construct into type I receptor deficient R1B cells. The luciferase activities from the transfected cells treated with or without TGF-β were measured as described previously (Bassing, C. H. et al., Science 264:87 (1994)). Bars represent standard errors (n=3).

FIG. 13. Myristylated Wild-Type FKBP12 But Not a Calcineurin-Binding-Deficient FKBP12 Mutant Specifically Blocks TGFβ Responses.

Figure 13B:
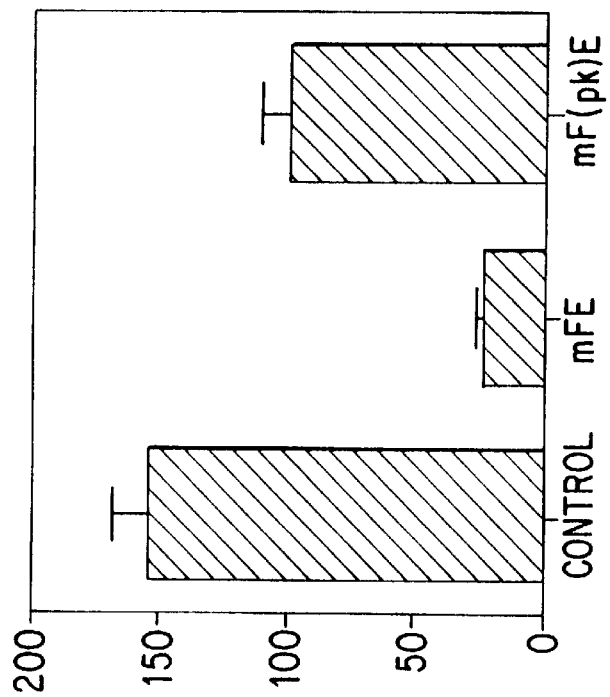
Figure 13A:
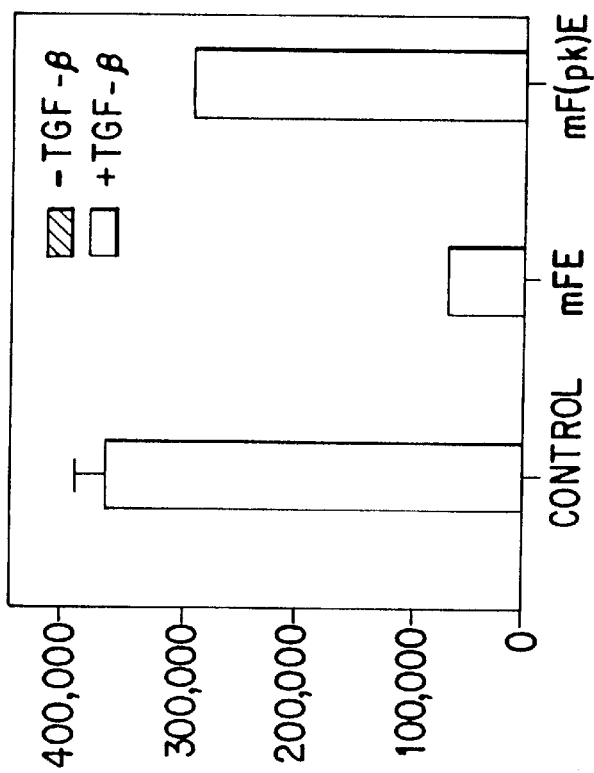

FIG. 13A Mv1Lu cells were transfected with 3TP-Luc alone (control), or with 3TP-Luc and the myristylated FKBP12 in PBJ5 (mFE), or with 3TP-Luc and the myristylated mutant FKBP12 in PBJ5 (mFpkE). Equal amount of myristylated wild-type FKBP12 and the mutant FKBP12 are expressed, as determined by Western blot using anti-FKBP12 antiserum (data not shown). The luciferase activities were measured as described in Experimental Procedures. The arbitrary units, with error bars, are presented. The experiments were performed twice, with each point determined in triplicates.

FIG. 13B The arbitrary units in FIG. 13A from the TGFβ-treated cells were divided by those from the untreated cells to show fold of increase of the luciferase activity upon TGFβ treatment.

Figure 13D:
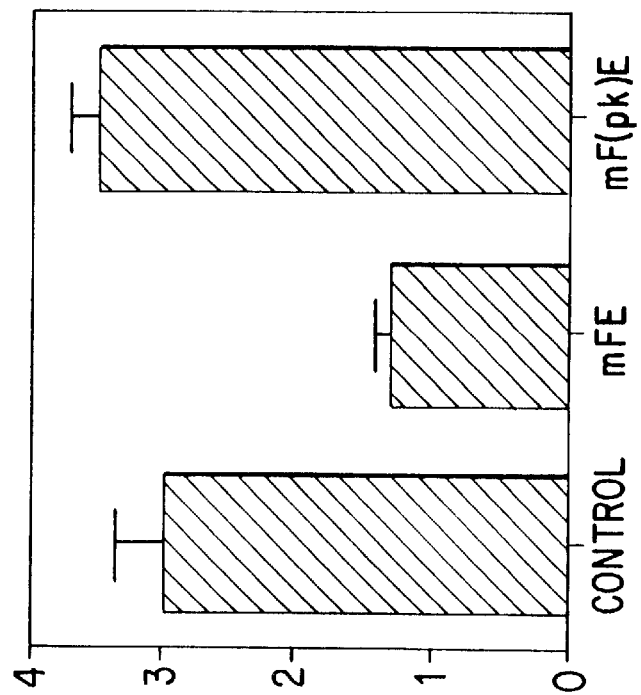
Figure 13C:
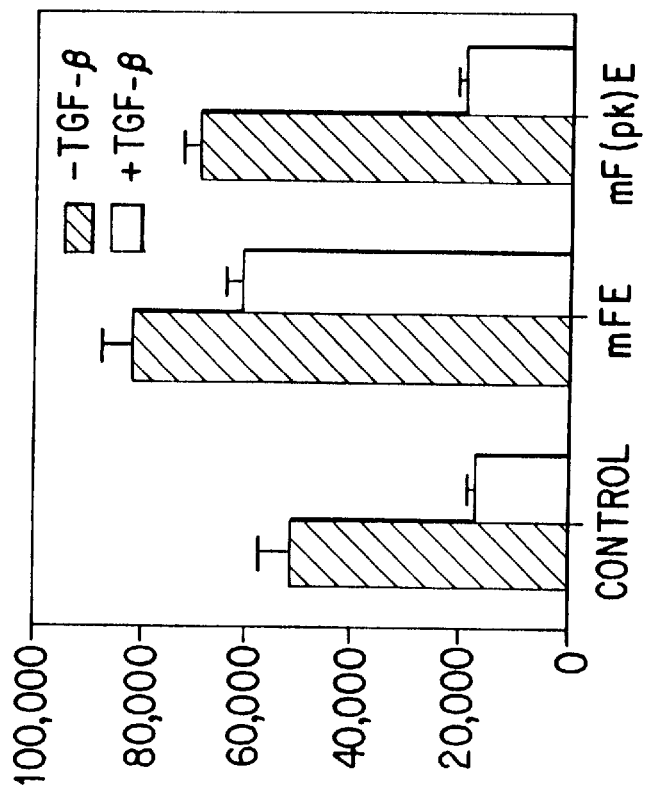

FIG. 13C Same as (A), except the cells were transfected with cyclin A-Luc reporter rather than 3TP-Luc.

FIG. 13D The arbitrary units in FIG. 13C from untreated cells were divided by those from the TGFβ-treated cells to show fold of decrease of the luciferase activity upon TGFβ treatment.

Figure 1A:
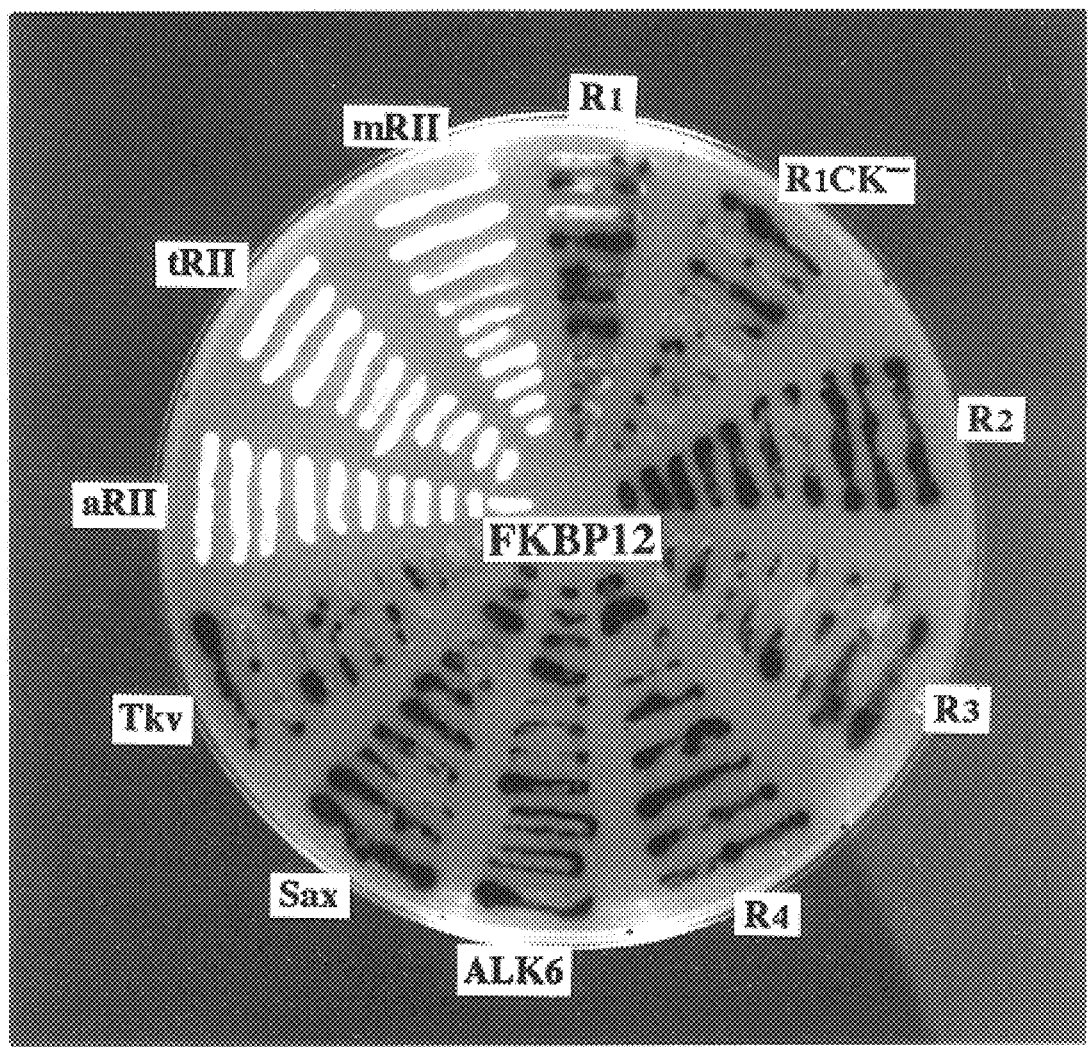
FIG. 1A. A yeast selective plate (Ura$^-$ His$^-$ Trp$^-$ galactose plate with X-Gal) containing yeast colonies expressing two fusion proteins: B42 fusion protein of FKBP12 and LexA fusion proteins of the cytoplasmic domains of different type I and type II receptors. aRII, activin type II receptor; tRII, TGF-β type II; and mRII, a putative MIS type II receptor. All fusion constructs were made by PCR and subcloning. All constructs were sequenced to assure fidelity, and fusion proteins were detected by Western blot to confirm expression (not shown).

FIGS. 1E, 1F and 1G A cartoon to depict a potential mechanistic difference between the endogenous free cytoplasmic FKBP12 (control), the membrane-bound myristoylated FKBP12 (mFE) and the membrane-bound myristylated calcineurin-binding-deficient FKBP12 (mFpkE), during ligand-induced activation of the TGFβ type I receptor. See text for details.

Figure 14:
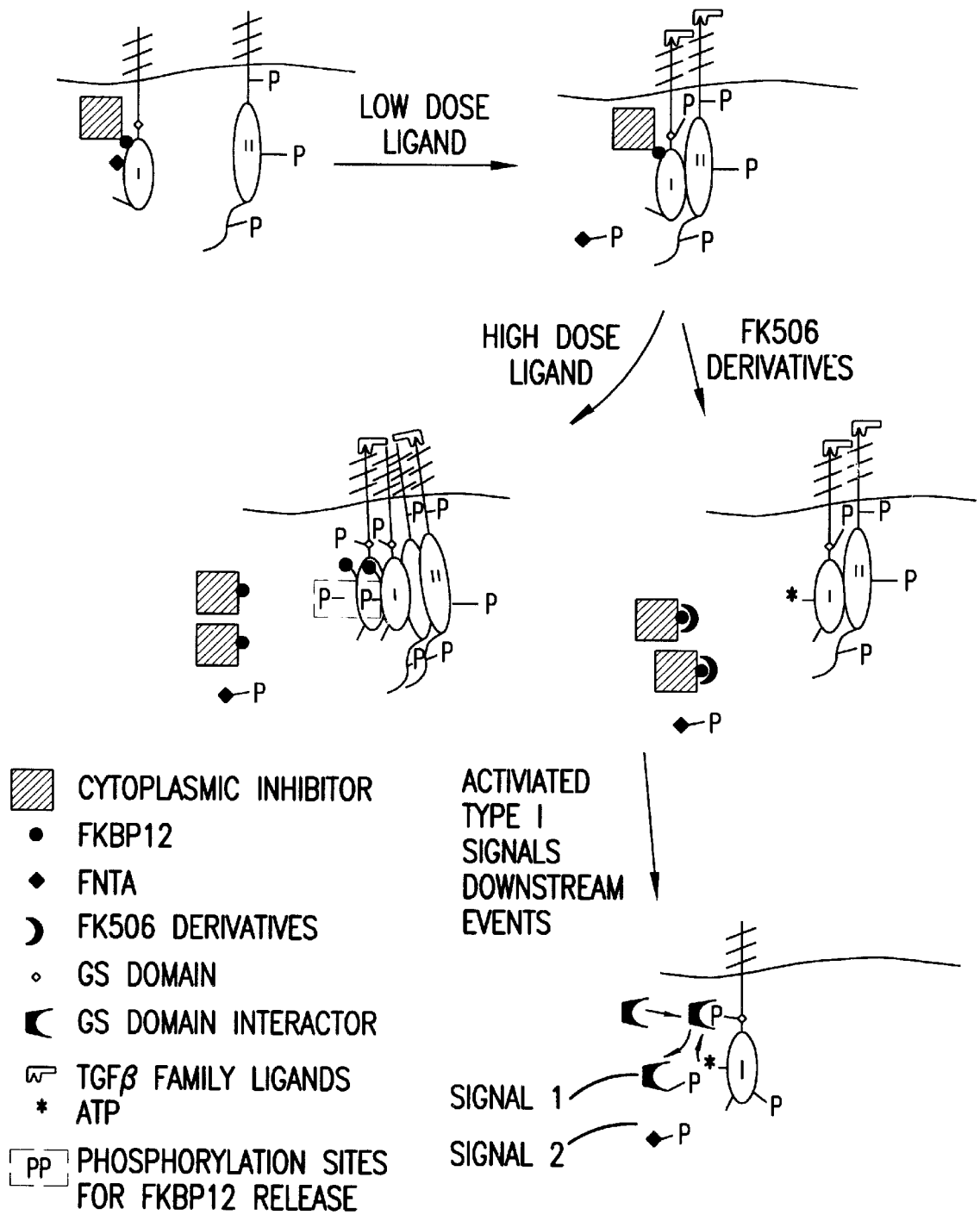

FIG. 14. A Model for the Events Involved in the Activation of the TGFβ Type I Receptor. See text for details.

DETAILED DESCRIPTION OF THE INVENTION

The Transforming Growth Factor-beta (TGF-β) family ligands have many important clinical applications relating to their ability to induce the formation of connective tissue, cartilage, and bone (Sporn, M. B. & A. B. Roberts, JAMA 262:938–941 (1989)). These include surgical wound healing in debilitated patients or those undergoing chemotherapy, treatment of diabetic, decubitus, or vascular ulcers, treatment of burns, repair of cardiac injury, as well as the treatment of fractures of bone and the induction of repair in damaged cartilage.

FKBP12 is known to mediate the immunosupressive activities of two macrolides, FK506 and rapamycin, by binding to the molecules and then recruiting and thereby inactivating the serine/threonine phosphatase calcineurin and the serine kinase FRAP (or RAFT1) respectively, resulting in the blockage of the signaling pathways mediated by calcineurin or FRAP (Siekierka, J. J. et al., *Nature* 341:755–777 (1989); Harding, M. W. et al., *Nature* 341:758–760 (1989); Bierer, B. E. et al., *Proc. Natl. Acad. Sci.* 87:9231–9235 (1990); Liu, J. et al., *Cell* 66:807–815 (1991); Liu, J. et al., *Biochemistry* 31:3896–3901 (1992); Clipstone, N. A. and Crabtree, G. R., *Nature* 357:695–697 (1992); O'Keefe, S. J. et al., *Nature* 357:692–694 (1992); Jain, J. et al., *Nature* 365:352–355 (1993); McCaffrey, P. G. et al., *Chem.* 268:3747–3752 (1993); Brown, E. J. et al., *Nature* 369:756–758 (1994); Sabatini, D. M. et al., *Cell* 78;35–43 (1994); Zheng, X.-F. et al., *Cell* 82:121–130 (1995); Brown, E. J. et al., *Nature* 377:441–446 (1995)). The present inventors have discovered that FKBP12 is a common cytoplasmic interactor of the TGF-β receptor family and, surprisingly, acts as an inhibitor of the TGF-β receptor-mediated signaling pathway. The present inventors have further discovered that macrolide potentiators can block FKBP12 binding to the TGF-β type 1 receptors thereby enhancing the cellular effects elicited by TGF-β ligands.

The different TGF-β type 1 receptors, which are expressed by a variety of cell types, include, but are not limited to, the mammalian type 1 receptors R1, R2, R3, R4, ALK3, and ALK6 (He, W. W. et al., *Dev. Dyn.* 196:133–142 (1994); ten Dijke P., et al., *Oncogene* 8:2879 (1993)), and the Drosophila type I receptors Sax, Tkv (Xie, T. et al., *Science* 263:1756–1759 (1994); Brummel, T. J. et al., *Cell* 78:251–261 (1994)). Cells known to express a TGF-β type 1 receptor and have a potent response to a TGF-β ligand include lymphocytes, fibroblasts, macrophages, synovial cells, and epithelial cells (both normal and malignant). As indicated, such cellular responses are important clinically in the healing or repair of several critical target tissues and organs, such as bone, connective tissue, eye, heart, liver, skin, the vascular system, and the endocrine system. By "a cellular response elicited by a TGF-β ligand" is intended any genotypic, phenotypic, and/or morphologic change to a cell, cell line, tissue, tissue culture, organ or patient that is induced by a TGF-β ligand. Thus, in one aspect, the present invention is directed to a method for potentiating a cellular response to a TGF-β ligand, which involves administering to a cell which expresses a TGF-β type 1 receptor an effective amount of a macrolide potentiator to enhance the cellular response elicited by the TGF-β ligand, wherein the macrolide potentiator enhances the cellular response by binding to FKBP12.

By "macrolide potentiator" is intended naturally occurring and synthetic macrolides capable of binding to FKBP12 and thereby enhancing a cellular response to a TGF-β ligand. Whether any candidate macrolide is capable of acting as a macrolide potentiator according to the present invention can be determined using art-known TGF-β ligand/cellular response assays, including the two in vitro screening assays described below and, in more detail, in Example 1.

Müllerian Inhibiting Substance (MIS) is a unique member of the TGF-β ligand family known to be responsible for regression of the Müllerian duct in fetal males through an active apoptotic process (Jost, A., *Arch. Anat. Micro. Morph. Exp.* 36:271–315 (1947); Price, J. M. et al., *Am. J Anat.* 149:353–376 (1977); Trelstad, R. L. et al., *Devl. Bio.* 92:27–40 (1982)). The activity of MIS in the regression of the Müllerian ducts can be measured directly in an organ culture assay (Donahoe, P. K. et al., *J. Surg. Res.* 23:141–148 (1977)). In this assay, urogenital ridges containing both the Wolffian duct and the Müllerian duct are isolated from fourteen and a half day female fetuses. The isolated urogenital ridges which have had no previous endogenous MIS exposure can then be incubated with different doses of exogenous MIS in an organ culture dish, and the regression of the Müllerian duct can be monitored by histological examination and the degree of the regression can be graded from grade 0 (no regression) to grade 5 (complete regression) as described (Donahoe, P. K. et al., *J. Surg. Res.* 23:141–148 (1977)). For example, when 1 µg MIS was added into the organ culture, grade 1.5 regression was observed. However, when 1 µM 15-O-desmethyl-FK520 was added together with 1 µg of MIS, the duct was replaced with a cord of pycnotic epithelial cells and connective tissue (grade 5, or complete regression). Thus, 15-O-desmethyl-FK520 is a macrolide potentiator according to the present invention.

Candidate macrolides can also be screened using a transcriptional response assay or an antiproliferative assay. TGF-β elicits two cellular responses when added to the mink lung epithelial cell line Mv1Lu: the growth inhibition response, which can be detected by a decrease in cell number, and the gene activation response, which can be measured by an increase in the luciferase activities resulting from the activation of a transfected luciferase reporter gene regulated by a Plasminogen Activator Inhibitor (PAI) promotor (Wrana, J. L. et al., *Cell* 71:1003–1014 (1992)). For example, when excess 15-O-desmethyl-FK520 (up to 1 µM) was added together with a low dose of TGF-β (15 pM) into Mv1Lu cells, both cellular responses elicited by TGF-β were greatly enhanced over that observed when TGF-β was administered alone.

Candidate macrolides for use in the present invention include FK506, FK506 derivatives and rapamycin. FK506 (tacrolimus) is a macrolide antibiotic that is produced by *Streptomyces tsukubaensis* No. 9993. The structure of FK506, which is a potent immunosuppressant, is given in Tanaka et al., *J. Am. Chem. Soc.* 109:5031 (1987). Rapamycin (sirolimus) is a macrolide antibiotic that is produced by *Streptomyces hygrospicus*. The structure of rapamycin, which is also a potent immunosuppressant, is given in McAlpine et al., *J. Antibiotics* 44:688 (1991) and Schreiber et al., *J. Am. Chem. Soc.* 113:7433 (1991). FK506 and rapamycin are believed to have somewhat different mechanisms of inducing immunosuppression; however, both bind strongly to FKBP12.

The toxicity of FK506 and rapamycin in mammals has limited their utility as pharmocological agents and prompted efforts to discover novel analogs of FK-type compounds which are less toxic but retain immunosupressive activity. Such compounds, which are described in detail in Luly, J. R., WO 94/21634, are also candidate macrolides according to the present invention. Preferably, however, the macrolides used according to the present invention are antagonists of FK506, i.e., macrolides that also bind FKBP12 but which, when compared to FK506, are incapable of, or have a reduced capacity for, inducing immunosuppression. Such antagonists of FK506, which are usually less toxic, include the FK506 derivatives disclosed in Fehr, T. and J.-J. Sanglier, WO 95/06649, which are of formula I:

Formula I

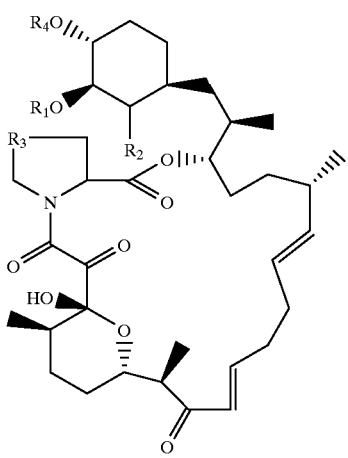

wherein

R₁ is H, alkyl, aryl, or acyl;
R₂ is H, or —OR₅, such that R₅ is H, alkyl, aryl, or acyl;
R₃ is —CH₂— or —CH₂CH₂—; and
R₄ is H, alkyl, acyl, or aryl.

Preferably, "alkyl" refers to $C_{1-6}$ alkyl, e.g., methyl or ethyl; "aryl" refers to an aromatic hydrocarbon radical having one or two aromatic rings, e.g., phenyl or benzyl; and "acyl" refers to alkylcarbonyl or arylcarbonyl (preferably a physiologically hydrolysable and acceptable acyl; that is, a residue which is cleavable under physiological conditions to yield an acid which is itself tolerated at the doses to be administered), e.g., acetyl, benzoyl, or salicyl.

In another embodiment, the macrolides of the invention are those of formula II:

Formula II

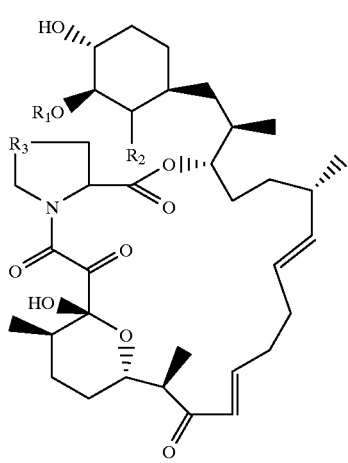

wherein R₁ is H or —CH₃; R₂ is H or —OH; and R₃ is —CH₂— or —CH₂CH₂—.

The macrolides may be produced synthetically, e.g., by total synthesis using a procedure analogous to that described for rapamycin by Nicolaou et al., *J. Am. Chem. Soc.* 115:4419 (1993), or by fermentation as described below, or by a combination of synthetic and biosynthetic means, e.g., by isolating fermentation products and further chemically modifying them. Preferably, the macrolides are produced by fermentation using a microorganism of the genus Micromonospora, preferably the novel species of the genus Micromonospora designated A92-306401; for example, the strain which has been deposited by the applicant under the Budapest Convention on Jul. 30, 1993 with the Deutsche Sammlung von Mikroorganismen und Zellkulturen GmbH (DSM), Mascheroder Weg 1 B, D-38124 Braunschweig, Germany under accession number DSM 8429.

Producing macrolides for use in the present invention can occur by alkylation or arylation of hydroxy groups, to yield macrolides of formula I wherein R₁, R₄, and/or R₅ is/are selected from alkyl or aryl, is performed, e.g., as described for rapamycin in WO 94/09010 or as described for FK506 in WO 92/20688, or for example by reacting such a compound with an organic radical attached to a leaving group (e.g., RX where R is the organic radical, e.g., an alkyl, allyl, or benzyl moiety, which is desired as the O-substituent, and X is the leaving group, e.g., CCl₃C(NH)O or CF₃SO₃) under suitable reaction conditions, e.g., in the presence of an acid like trifluoromethanesulfonic acid, camphorsulfonic acid, p-toluenesulfonic acid or their respective pyridinium or substituted pyridinium salts when X is CCl₃C(NH)O or in the presence of a base like pyridine, a substituted pyridine, diisopropylethylamine or pentamethylpiperidine when X is CF₃SO₃. Acylation to form macrolides of formula I wherein R₁, R₄, and/or R₅ is/are acyl is accomplished by esterification of the hydroxy group using conventional means, e.g., as described in U.S. Pat. No. 4,316,885 for rapamycin, or e.g., reacting compounds with an anhydride, e.g., acetic anhydride, or acid halide, e.g., alkylcarbonyl halide, in the presence of an acid binding agent, e.g. a base, e.g., pyridine, under suitable reaction conditions.

Thus, macrolides of formula I and formula II can be produced by cultivating a microorganism of the genus Micromonospora, e.g., of the species Micromonospora sp.A92-306401, e.g., of the deposited strain DSM 8429 in an appropriate culture medium and isolating the macrolide. An appropriate culture medium is a medium containing suitable sources of nitrogen, carbon, and trace minerals. Preferably the sources of carbon in the culture medium are carbohydrates such as glucose, xylose, galactose, glycerin, starch, and dextrin. Preferred sources of nitrogen are yeast extract, meat extract, peptone, gluten meal, cottonseed meal, soybean meal, casein hydrolysates, soybean hydrolysates, yeast hydrolysates, and the like and inorganic and organic nitrogen-containing compounds such as ammonium salts, urea, amino acids and the like. Conventional fermentation age and trace materials may also be added.

Example macrolide potentiators for use in the present invention include 15-O-desmethyl-FK520 and L-685,818. The structure of 15-O-desmethyl-FK520 is provided in Liu, J., *Biochemistry* 31:3896–3901 (1992). 15-O-desmethyl-FK520, an FK506 antagonist analog, binds with high affinity to FKBP12 but does not act as an immunosuppressive agent. This compound can be prepared from 15,31-bisdesmethyl-FK520 using the enzyme 31-O-desmethylimmunomycin O-methyltransferase (DIMT) supplemented with $Mg^{+2}$ ion, in the presence of the methyl donor, S-adenosyl methionine (SAM).

The structure for L-685,818 is provided in Dumont, F. J., et al., *J. Exp. Med.* 176:751–760 (1992); Rotonda, J., et al., *The Journal of Biological Chemistry* 268(11):7607–7609 (1993); and Becker, J. W. et al., *The Journal of Biological Chemistry* 268 (15):11335–11339 (1993). Like 15-O-desmethyl-FK520, L-685,818 is also a FK506 antagonist analog that binds with high affinity to FKBP12 but does not act as an immunosuppressive agent. L-685,818 is an antagonist of FK506 despite the fact that it differs from the drug by only the addition of a hydroxyl group at C-18 and an ally-to-ethyl change at C-21.

15-O-desmethyl-FK520 and L-685,818 do not induce toxicity in animal models. The functional difference between FK506 and FK506 non-immunosupressive derivatives is not caused by how they interact with FKBP12, but rather by differences in how their complexes interact with calcineurin or other targets (Schrieber, S. L., *Science* 251:283–287 (1991)). For example, for L-685,818, the addition of a hydroxyl group to the C-18 region, which is in close contact with calcineurin in the FKBP12-ligand-enzyme complex, produces either a steric clash or forces a hydrophilic group into an hydrophobic environment (Rotonda, J., et al., *The Journal of Biological Chemistry* 268(11):7607–7609 (1993); and Becker, J. W. et al., *The Journal of Biological Chemistry* 268 (15):11335–11339 (1993)).

By the invention, a macrolide potentiator can be administered in vitro, ex vivo or in vivo to cells which express a TGF-β receptor to enhance the cellular response to an endogenous, or an exogenously added, TGF-β ligand. By administration of an "effective amount" of a macrolide potentiator is intended an amount of the macrolide that is sufficient to enhance a cellular response to a TGF-β ligand. One of ordinary skill will appreciate that effective amounts of a macrolide potentiator can be determined empirically and may be employed in pure form or, where such forms exist, in pharmaceutically acceptable salt, ester or prodrug form. Together with a TGF-β ligand (discussed below), the macrolide potentiator may be administered as pharmaceutical compositions in combination with one or more pharmaceutically acceptable excipients. It will be understood that, when administered to a human patient, the total daily usage of the compounds and compositions of the present invention will be decided by the attending physician within the scope of sound medical judgement. The specific therapeutically effective dose level for any particular patient will depend upon a variety of factors including the type and degree of the cellular response to be achieved; activity of the specific macrolide potentiator employed; the specific composition employed; the age, body weight, general health, sex and diet of the patient; the time of administration, route of administration, and rate of excretion of the macrolide potentiator; the duration of the treatment; drugs used in combination or coincidental with the specific macrolide potentiator; and like factors well known in the medical arts. For example, it is well within the skill of the art to start doses of macrolides at levels lower than required to achieve the desired therapeutic effect and to gradually increase the dosage until the desired effect is achieved.

For example, satisfactory results are obtained by oral administration of a macrolide potentiator at dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging may also be arranged in a patient specific manner to provide a predetermined concentration of a macrolide in the blood, as determined by the RIA technique. Thus patient dosaging may be adjusted to achieve regular ongoing trough blood levels, as measured by RIA, on the order of from 50 to 1000 ng/ml, preferably 150 to 500 ng/ml. A kit for measuring blood levels of macrolides is described in Legay, F. and R. Wenger, WO 95/07468.

As indicated, a macrolide potentiator can be administered to cells which express a TGF-β receptor together with (i.e., before, after, or simultaneously with) a TGF-β ligand. By "a TGF-β ligand" is intended naturally occurring, recombinant, and synthetic ligands that are capable of binding to a member of the TGF-β receptor family and inducing the TGF-β receptor-mediated signaling pathway. Naturally occurring members of the TGF-β ligand family include, but are not limited, (1) the closely related members: TGF-β1, TGF-β2, TGF-β3, TGF-β4, and TGF-β5 (Derynck, R., et al., *EMBO J.* 7:3737–3743 (1988); Jakowlew et al., *Molec. Endocrinol*, 2:1186–1195 (1988)); and (2) those members that are more distantly related to TGF-β1: Müllerian Inhibiting Substance (MIS) (Cate, R. L., et al., *Cell* 45:685–698 (1986)), the α, βA, and βB chains of the inhibins and activins (Mason, A. J., et al., *Nature* 318:659–663 (1985); Forage, R. G., et al., *Proc. Natl. Acad Sci.* 3:3091–3095 (1986)), the bone morphogenetic proteins 2a, 2b, and 3 (Wozney, J. M., et. al., *Science* 242:1528–1534 (1988)), the Vgr-1 gene product (Lyons, K., et al., *Proc. Natl. Acad. Sci. USA* 86:4554–4558 (1989)), the decapentaplegic (DPP) gene product (Padgett, et al., *Nature* 325:81–84 (1987)), and the growth differentiation factors-1–9 (GDFs-1–9) (Lee, S.-J., et al., WO 95/01801)).

Some cellular responses elicited by these TGF-β ligands are as follows: TGF-β1: inhibition of cell proliferation and stimulation of connective and supporting tissue formation; TGF-β2: cellular effect is very similar to that elicited by TGF-β1, but more active in mesoderm induction; TGF-β3–5: similar to TGF-β1 and TGF-β2 in stimulating growth of fibroblasts and inhibiting growth of epithelial cells; MIS: causes Müllerian duct regression in males and has significant antiproliferative activity against gynecological tumors and ocular melanoma; the inhibin α, βA, and βB chains: inhibit FSH secretion by pituitary cells; the activin α, βA, and βB chains: activate FSH secretion by pituitary cells; the BMPs 2a, 2b, and 3: induce ectopic cartilage formation; Vgr-1: localizes the vegetal pole of eggs; DPP: dorsalventral axis formation and morphogenesis of the imaginal disks; and GDFs-1–9: inhibition of cell proliferation and stimulation of connective and supporting tissue formation.

Most TGF-β ligands are synthesized naturally as large latent precursors that require proteolytic processing and subsequent separation of the amino- and carboxyl-terminal segments for activation (Massague, J., *Cell* 49:437–438 (1987)). Thus, by "a TGF-β ligand," is further intended biologically active fragments of the TGF-β ligands described above. For example, it is known in the art that the antiproliferative activity of MIS resides in its 12.5 kD (25 kD in dimer form) C-terminal domain, which can be produced by plasmin cleavage of intact MIS (Pepinsky, R. B., et al., *The Journal of Biological Chemistry*, 263(35):18961–18964 (1988); MacLaughlin, D. T., et al., *Endocrinology* 131(1): 1–6 (1992)). Thus, TGF-β ligands according to the present invention can be generated by enzymatic or physical cleavage of naturally occurring or recombinantly produced TGF-β ligands using known techniques. Alternatively, TGF-β ligands according to the present invention can be produced synthetically.

Particularly suitable synthetic TGF-β ligand peptides are 7–60 amino acids in length, which substantially correspond in sequence to the amino acid sequences of the carboxyterminal portion of the naturally occurring TGF-βs (i.e., TGF-β1, TGF-β2 and TGF-β3). For example, TGF-β ligand peptides can be synthesized which correspond to the following residues of TGF-β1: 280–339; 340–391; 280–293; 296–322; 328–354; 358–382; 366–387; 364–378; 368–374. Preferably, the peptides will include the residues 368–374 of TGF-β1. The amino acid sequences for these peptides are disclosed in Postlethwaite, A. E., U.S. Pat. No. 5,436,228, and can be synthesized using classical Merrifield synthesis techniques. For example, oligopeptides can be synthesized by the solid phase method of Merrifield with the aid of a Beckman automated peptide synthesizer. For longer peptides (up to 60 residues), an Applied Biosystems Peptide Synthesizer which utilizes symmetric anhydride coupling to the free amino group of the growing peptide chains with greater coupling frequency can be used.

As indicated, the TGF-β ligands are known to elicit a wide array of cellular responses, several of which have clinical applications. By "patient," is intended animals, preferably mammals, including humans. By the invention, the dose of the TGF-β ligand can be significantly reduced when co-administered with a macrolide potentiator. By "an effective amount of a TGF-β ligand," is an amount effective to elicit a cellular response in cells which express a TGF-β receptor. Example clinical therapies which involve administering a TGF-β ligand to a patient are discussed in more detail below. Other such therapies are known in the art.

The TGF-β isoforms (i.e., TGF-β1–5) promote proliferation of connective and soft tissue for wound healing applications. In one embodiment, the TGF-β ligand and macrolide potentiator are administered by treating a device with the drugs and implanting the device into the patient at the site of the deficiency. The composition may, optionally, also contain a osteogenic cell source when the site is deficient in such cells. The device may consist of any device suitable for implantation, including a molded implant, plug, prosthetic device, capsule, titanium alloy, sponge, or ceramic block. For bone defects involving gaps, such as a dry socket or non-union fracture, a plug may be used to fill the gap. The plug may be composed of, for example, hydroxyapatite or collagen on which the pharmaceutical composition is absorbed.

For larger bone defects resulting from, e.g., trauma or skeletal reconstruction around an ulcer or hip prosthesis, the device is preferably a made-to-fit ceramic block. More preferably, the ceramic block comprises 0–100% hydroxyapatite and the remaining 100–0% tricalcium phosphate, by weight, most preferably 60% hydroxyapatite and 40% tricalcium phosphate.

In a specific embodiment for a jaw implant, a calcium carbonate moldable material or Interpore™ molding device is molded to fit the jaw using a 3-dimensional X-ray of the jaw before surgery, and the molded material is impregnated with the TGF-β ligand and macrolide potentiator. Then, dispensed bone marrow from another site of the animal (e.g., from the hip) is infiltrated into the mold, and the mold is placed into the jaw for final implantation.

Preferably, the device is treated with the TGF-β/macrolide composition (which can include both a solution and a gel formulation) for a sufficient period of time to allow adsorption, and to allow drying in the case of the gel. The concentration of TGF-β ligand and macrolide potentiator in the solution or gel and the time of exposure depends on a number of factors, including the volume of the defect, the potency of the pharmaceutical composition, and the nature of the site to which it is applied. As the size of the defect increases, or when the site is other than a bone site, the concentration of the TGF-β ligand and macrolide potentiator and the time of presoaking should be increased. The treatment is for preferably at least about 0.5 hour, depending on the factors mentioned above (more preferably at least about 1 hour, and most preferably 1–2 hours), before implantation. Also, depending on the above considerations, the concentration of TGF-β ligand in the pharmaceutical composition is preferably at least about 1 ng/ml (more preferably at least about 1–10 up to 100 ng/ml). Suitable macrolide potentiator concentrations are discussed above. The treatment may consist of any mode by which the composition is applied to the device to deliver effectively the TGF-β ligand, the macrolide potentiator, and the osteogenic cell source. Such treatment includes, for example, adsorption, covalent crosslinking, or impregnation, depending in part on the nature of the indication.

As a general proposition, the TGF-β ligand is formulated and delivered to the target site at a dosage capable of establishing at the site a TGF-β ligand level greater than about 0.1 ng/cc. Typically, the TGF-β ligand concentrations range from about 0.1 ng/cc to 5 mg/cc, preferably from about 1 to 2000 ng/cc. These intra-tissue concentrations are maintained preferably by topical application and/or sustained release.

As noted above, these suggested amounts of TGF-β ligand and the above discussed amounts for the macrolide potentiator are subject to a great deal of therapeutic discretion. The key factor in selecting an appropriate dose and scheduling is the result obtained. Clinical parameters to determine an endpoint include increase in bone formation and mass and in radiographically detectable bone height. Such measurements are well known to those clinicians and pharmacologists skilled in the art.

To be effective, the TGF-β ligand is converted by the body to its activated form or administered as such. The TGF-β ligand is suitably administered in an inactive or delayed release form such as a complex of mature TGF-β ligand with pro-TGF-β ligand not containing mature TGF-β (i.e., the remaining precursor of TGF-β), with a TGF-β binding protein, or with alpha$_2$-macroglobulin. The latent form is then converted to the active form either by naturally occurring mechanisms in the local environment or by formulation with TGF-β activating agents described above. See, e.g., Gentry et al., *Mol. Cell. Biol.* 8:4162–4168 (1988); Miyazono et al., *J. Biol. Chem.* 263:6407–6415 (1988); Wakefield et al., *J. Biol. Chem.* 263:7646–7654 (1988); Keski-Oja et al., *J. Cell Biochem. Suppl.* 11A:60 (1987); Kryceve-Martinerie et al., *Int. J. Cancer.* 35:553–558 (1985); Lawrence et al., *Biochem. Biophys. Res. Commun.* 133:1026–1034 (1985); Lawrence et al., *J. Cell Physiol.* 121:184–188 (1984). Thus, the pH of the pharmaceutical composition may suitably reflect the conditions necessary for activation.

For local application of the TGF-β/macrolide composition, for example, in the case of a bone defect that is a crack, e.g., a union fracture, the carrier may be any vehicle effective for this purpose. For obtaining a gel formulation, the liquid composition is typically mixed with an effective amount of a water-soluble polysaccharide, polyethylene glycol, or synthetic polymer such as polyvinylpyrrolidone to form a gel of the proper viscosity to be applied topically. The polysaccharide is generally present in a gel formulation in the range of 1–90% by weight of the gel, more preferably 1–20%. Examples of other suitable polysaccharides for this purpose, and a determination of the solubility of the polysaccharides, are found in EP 267,015. See, also, U.S. Pat. No. 5,409,896.

In another embodiment, the macrolide potentiator is administered to a patient in a pharmaceutical composition with the chemotactic wound healing TGF-β ligand peptides described above and in U.S. Pat. No. 5,436,228. Such compositions are useful for promoting proliferation of connective and soft tissue for wound healing applications.

In a further embodiment, TGF-β3 and a macrolide potentiator are administered to a patient for preventing or retarding the formation of scar tissue in connection with ocular trauma caused by, for example, glaucoma filtration surgery. The pharmaceutical composition contains TGF-β3 and a macrolide potentiator in an amount sufficient to suppress the formation of, or alter the composition of, extracellular matrix synthesized by fibroblasts at the site of the glaucoma filtration surgery. The amount of macrolide potentiator that may be administered is discussed above. The amount of TGF-β3 that may be included for this purpose will generally be from about 0.01 ng/ml to about 100 µg/ml. The preferred range is from about 1 to about 500 ng/ml. Modes for administering the pharmaceutical composition optically are discussed below. See, also, U.S. Pat. No. 5,449,671.

In further aspects, a TGF-β ligand and a macrolide potentiator can be administered to a patient for tissue growth promotion in chronic wounds, for multiple sclerosis treatment, for dermal wound healing, for removing dead bum and ulcer wound tissue, for treating chronic ulcers, for treating osteoporosis, and for treating psoriasis. Acceptable dosages and modes of administration are discussed above and below and will be apparent to the skilled artisan.

In a still further aspect, where the TGF-β ligand is MIS, the pharmaceutical composition comprising MIS and a macrolide potentiator can be administered to a patient for treating gynecological tumors and ocular melanoma. For example, it is known that MIS inhibits growth of vulvar carcinoma, endometrial adenocarcinoma, cervical carcinoma, ovarian carcinoma, and ocular melanoma both in vitro and in vivo (Chin, T., et al., *Cancer Research* 51:2101–2106 (1991); Parry, R. L., et al., *Cancer Research* 52:1182–1186 (1992); Boveri, J. F., et al., *Gynecol Oncol* 49(1):116 (1993); Kurian, M. S., et al., *Clinical Cancer Research* 1(3):343–349 (1995)). MIS is effective in treating such tumors when proteolytically cleaved to form protein fragments of about 57 kD and 12.5 kD (Pepinsky, R. B., et al., *The Journal of Biological Chemistry*, 263(35):18961–18964 (1988); MacLaughlin, D. T., et al., *Endocrinology* 131(1): 1–6 (1992)). It has been discovered that the antiproliferative activity of MIS resides in its 12.5 kD C-terminus (MacLaughlin, D. T., et al., *Endocrinology* 131 (1): 1–6 (1992)). Thus, MIS can be administered to a patient in intact form and native proteolytic enzymes relied on for activation, or the active 12.5 kD C-terminal fragment can be administered either alone or together with the 57 kD N-terminus. By the invention, the antiproliferative effects of MIS can be enhanced by co-administration with a macrolide potentiator described herein.

From above, pharmaceutical compositions are provided comprising a macrolide potentiator, a TGF-β ligand, and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray. Importantly, by co-administering a macrolide potentiator and TGF-β ligand, clinical side effects can be reduced by using lower doses of both the TGF-β ligand and the macrolide potentiator. As indicated, it will be understood that the macrolide potentiator can be "co-administered" either before, after, or simultaneously with the TGF-β ligand, depending on the exigencies of a particular therapeutic application. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), carboxymethylceuulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drugs, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcerulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and I) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isoptopyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredient in finely divided form may be used in admixture with a larger-sized pharmaceutically acceptable inert carrier comprising particles having a size, for example, of up to 100 μm in diameter. Suitable inert carriers include sugars such as lactose. Desirably, at least 95% by weight of the particles of the active ingredient have an effective particle size in the range of 0.01 to 10 μm.

Alternatively, the composition may be pressurized and contain a compressed gas, such as nitrogen or a liquefied gas propellant. The liquefied propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye to, for example, reduce the formation of scar tissue as a result of a trama to the cornea. The macrolide potentiatior and/or TGF-β ligand is/are delivered in a pharmaceutically acceptable ophthalmic vehicle, such that the compound(s) is/are maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the macrolide potentiator and/or TGF-β ligand with suitable non-irritating excipients or carriers such as cocoa butter, polyethylene glycol or a suppository wax which are solid at room temperature but liquid at body temperature and therefore melt in the rectum or vaginal cavity and release the drugs.

The macrolide potentiator and/or TGF-β ligand can also be administered in the form of liposomes. As is known in the art, liposomes are generally derived from phospholipids or other lipid substances. Liposomes are formed by mono- or multi-lameflar hydrated liquid crystals that are dispersed in an aqueous medium. Any non-toxic, physiologically acceptable and metabolizable lipid capable of forming liposomes can be used. The present compositions in liposome form can contain, in addition to the macrolide and/or ligand, stabilizers, preservatives, excipients, and the like. The preferred lipids are the phospholipids and the phosphatidyl choaes (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

The present invention further provides a screening method for determining whether a particular macrolide is capable of enhancing a cellular response to a TGF-β ligand. The method involves contacting cells which express a TGF-β receptor with a macrolide and a TGF-β ligand, assaying a cellular response, and comparing the cellular response to a standard cellular response, the standard response being assayed when contact is made with the TGF-β ligand in absence of the macrolide, whereby an increased cellular response over the standard indicates that the macrolide is a potentiator of TGF-β ligand activity.

By "assaying a cellular response" is intended qualitatively or quantitatively measuring a cellular response to a macrolide and/or a TGF-β ligand (e.g., determining or estimating an increase or decrease in gene expression or cell number or $^3$H-thymidine labeling). By the invention, the macrolide is a potentiator of TGF-β ligand activity if the cellular response is enhanced over that observed due to the TGF-β ligand in absence of the macrolide. As indicated, any of the art-known in vitro and in vivo cellular response assays to TGF-β ligands can be used to implement the screening method of the present invention. These include the organ culture and transcriptional response assays described above and in Example 1. Other in vitro and in vivo cellular response assays to TGF-β ligands are described in the numerous articles compiled in "Transforming Growth Factors-βs Chemistry, Biology, and Therapeutics," Annals of New York Academy of Sciences 593 (Piez and Sporn, eds. 1990).

Having generally described the invention, the same will be more readily understood through reference to the follow-

EXPERIMENTAL

EXAMPLE 1

The Immunophilin FKBP12 Functions as a Common Inhibitor of the TGF-β Family Type I Receptors Introduction Here we report that FKBP12 in the absence of macrolides can specifically bind to the cytoplasmic domains of all seven tested members of the TGF-β type I receptor family. Detailed domain mappings of two type I receptors and FKBP12 in the yeast two-hybrid system revealed the molecular basis for the specific direct protein-protein interaction and suggests similarity between FKBP12/receptor interaction and FKBP12/macrolide interaction. The FKBP12/receptor interaction was further confirmed in mammalian cells and shown to be competed by an excess amount of FK506 non-functional derivatives, which bind to FKBP12 at the same site and with similar affinity in comparison to FK506, or rapamycin, but are inactive in mediating immunosuppression presumably due to their defects in recruiting either calcineurin or FRAP. Using these FK506 derivatives, we directly tested the functional role of FKBP12 in the signaling events of two TGF-β family members, TGF-β and the Müllenan Inhibiting Substance (MIS), a gonadal glycoprotein responsible for the regression of the Müllerian duct in the male fetus (Jost, A., *Arch. Anat. Micro. Morph. Exp.* 36:271–315 (1947); Trelstad, R. L. et al., *Devl. Bio.* 92:27–40 (1982)). By blocking FKBP12 binding to the type I receptors, the FK506 derivatives did not inhibit, but instead greatly enhanced the cellular effects of both TGF-β and MIS, indicating that FKBP12 functions as an inhibitor of the TGF-β family mediated signaling. Further, FKBP12 was found to be absent from the ligand-bound, activated type I and type II receptor complex, but is present in the complex if the type II receptor kinase is defective, suggesting a serine/threonine phosphorylation-dependent release of FKBP12 is involved in the activation of the type I receptor-mediated signaling.

Experimental Procedures

Strains and cell lines

The yeast strain EGY48 MAT a trp1 ura3 his3 LEU2::pLexA op6-LEU2 was used as a host for all interaction experiments and was described previously (Gyuris, J. et al., *Cell* 75:791–803 (1993)). In the library screening and for testing protein-protein interactions, it contained the plasmid pSH 18-34 (Gyuris, J. et al., *Cell* 75:791–803 (1993)), which contains four LexA operator sites. *E. coli* K-12 strain KC8 pyrF::Tn5, hsdR, leuB600, trpC9830, lacD74, stra, galK, hisB436 was used for the rescue of plasmids from yeast exhibiting positive interaction with the bait (Gyuris, J. et al., *Cell* 75:791–803 (1993)).

Plasmids and plasmid construction

The yeast expression vectors pEG202 and pJG4-5, which allow the expression of LexA and B42 fusion proteins are as previously described (Gyuris, J. et al., *Cell* 75:791–803 (1993); Zervos, A. S. et al., *Cell* 72:223–232 (1993)). The multiple LexA and B42 fusion constructs were made by PCR amplification of the designed cDNA sequences with two restriction sites attached at 5' (EcoR1) and 3' (Xho1) ends for subcloning into the respective sites within the multiple cloning sites of either pEG202 and pJG4-5. DNA sequencing was carried out to assure the fidelity of the cDNA sequences. Mammalian expression constructs of TGF-β type I and type II receptors and their kinase deficient mutants were described previously (Bassing, C. et al., *Science* 263:87–89 (1994)).

R4VVAAA was made by mutating two threonines and three serines within the GS core sequence TTSGSGSG (SEQ ID NO:18) to valine and alanine respectively. R4 tailless was made by introducing two stop codons at the fifth and sixth amino acids from the carboxyl-terminus end of R4. R4ΔK was made by replacing the twenty-third amino acid (arginine) from the carboxyl-terminus end of R4 with a stop codon. Mutagenesis was performed using the U.S.E. mutagenesis kit from Pharmacia Biotech. The T7 tagged FKBP12 was made by subcloning full length FKBP12 cDNA into EcoR1/Xho1 sites within the multiple cloning sites of plasmid PET 28a (Novogen) which was then fused inframe with the amino-terminus T7 tag. The fused cDNA for T7 tagged FKBP12 was then subcloned into the pCMV8 vector.

Yeast two-hybrid screen

We used a modified version of the yeast two-hybrid system developed by Roger Brent and his colleagues (Gyuris, J. et al., *Cell* 75:791–803 (1993); Zervos, A. S. et al., *Cell* 72:223–232 (1993)). The cytoplasmic domains of the type I receptors were used as the baits. Positives were first selected by their ability to grow on plates lacking leucine, and then further tested for their ability to turn blue on plates with X-gal, as previously described in great detail (Gyuris, J. et al., *Cell* 75:791–803 (1993)). Library plasmids from positives were rescued from yeast by transforming total DNA preparations from each yeast colony into KC8 cells and selected on 1×A minimal plates lacking tryptophan as described previously (Hoffman, C. S. and Winston, F., *Gene* 57:267–272 (1987)), followed by DNA sequencing.

Two-hybrid interaction tests in yeast

The yeast strain EGY 48 was transformed with plasmid PSH 18-34 (Gyuris, J. et al., *Cell* 75:791–803 (1993)), and maintained in yeast minimal media lacking uracil. For testing protein-protein interactions, one protein was fused to the LexA DNA binding domain in the pEG202 plasmid, while the other was fused to the activation domain B42 in pJG4-5 plasmid. Yeast was first transformed with one fusion construct, then selected and re-transformed with the other. Nine to ten individual colonies of transformants containing both constructs were then restreaked onto a new Ura⁻ His⁻ Trp⁻ glucose plate, which were then replica plated onto both glucose and galactose Ura⁻ His⁻ Trp⁻ plates with X-gal. Positive interactions were detected when the yeast turned blue on galactose plates, but remained white on glucose plates. Autoactivation of the LacZ reporter gene by LexA fusion proteins was detected when the transformants turned blue on glucose plates.

COS cell transfection, metabolic labeling, receptor cross-linking, immunoprecipitation and Western blot For testing FKBP12 binding to ligand-free TGF-β type I receptor (either wild type or mutants) by co-immunoprecipitations, COS1 cells grown in P-100 dishes were transfected with 4 µg of T7 tagged FKBP12 in pCMV8 and 6 µg of R4 (or mutant R4) in pCMV6 using the DEAE-dextran method. In the case of using metabolic labeling to detect co-precipitation of FKBP12 and R4, 40–44 hours after transfection COS1 cells were incubated for 4 hours with 50 µCi/ml [$^{35}$S]-methionine in methionine-free media and lysed in lysis buffer (20 mM Tris-HCl [pH 7.4], 150 mM NaCl, 0.5% Triton X-100, 1 mM EDTA) in the presence of a mixture of protease inhibitors. Anti-T7 monoclonal antibody (5 µl) was added into 200 µl of cell lysates, incubated at 4° C. for 2 hours, absorbed with protein A sepharose beads, and washed three times with wash buffer (20 mM Tris-HCl [pH 7.4], 150 mM NaCl, 0.1% Triton X-100, 1 mM EDTA). Proteins were eluted from the sepharose beads using 2× SDS-PAGE denaturing sample buffer, separated on 15% SDS-PAGE. The gel was treated with Autofluor (National Diagnostic), dried and subjected to autoradiography for 48 hours. In the case of using Western blot to detect co-precipitated T7 tagged FKBP12, cell lysates were immunoprecipitated with 10 μl of VPN antiserum, which recognizes a juxtamembrane region of the TGF-β type I receptor (Franzen, P. et al., Cell 75:681–692 (1993)). The immunoprecipitates were separated on 15% SDS-PAGE, electrotransferred onto nitrocellulose membrane, blotted using anti-T7 monoclonal antibody, and detected by ECL (Amersham).

For testing the effect of non-functional FK506 derivatives (L685,818 from Merck Laboratories and 15-O-desmethyl-FK520 from Sandoz) on FKBP12 binding to R4, 2 hours after transfection COS1 cells were treated with the derivatives for 44 hours and then labeled for 4 hours with 50 μCi/ml [$^{35}$S]-methionine in methionine-free media 40–44 hours after transfection. Cells were then lysed and immunoprecipitation was carried out as described above.

For testing FKBP12 binding to the ligand-bound type I receptor, COS cells were transfected with 4 μg of T7-FKBP12 pCMV8, 6 μg of R4 (or R4K$^-$) pCMV6 and 5 μg of RII (or RIIK$^-$) pcDNA1. Forty-eight hours after transfection, cells were incubated for 3 hours at 4° C. with [$^{125}$I]-labeled TGF-β at 250 pM. Cross-linking of receptor with the ligand was carried out as described previously (Massagué, J., J. Biol. Chem. 260:7059–7066 (1985); Massagué, J. and Like, B., J. Biol. Chem. 260:2636–2645 (1985)). Cells were lysed in lysis buffer as above followed by immunoprecipitation, SDS-PAGE and autoradiography.

Urogenital Ridge Organ Culture Assay

The organ culture assay was carried out as described previously (Donahoe, P. K. et al., J. Surg. Res. 23:141–148 (1977)). Briefly, urogenital ridges containing Wolffian and Müllerian ducts from 14.5 day female rat fetuses were maintained in CMRL media with 10% fetal calf serum, 100 units/ml penicillin, and 100 μg/ml streptomycin. To test the effect of the non-functional derivatives of FK506 (L685,818 or 15-O-desmethyl FK520) on Müllerian duct regression, the specimens were treated with the indicated doses of MIS in the presence or absence of the non-functional derivatives of FK506 and incubated at 37° C. in 5% $CO_2$ and 95% air. After 72 hours, the specimens were fixed in formalin, dehydrated in an alcohol series, cleared in xylene, embedded in paraffin, cut in serial cross sections, stained with hematoxylin and eosin and graded for regression of the Müllerian duct as described (Donahoe, P. K. et al., J. Surg. Res. 23:141–148 (1977)).

Transcriptional Response Assay

Two TGF-β responsive mink lung epithelial cell lines Mv1Lu and L17, the latter being a highly transfectable clone of R1B lacking the functional type I receptor of TGF-β, were used in a transcriptional response employing a DEAE-dextran method (Bassing, C. et al., Science 263:87–89 (1994); Wrana, J. L. et al., Nature 370:341–47 (1994)). Briefly, cells grown to 50% confluency in 6-well plates were transiently transfected with the transcriptional response reporter construct p3TP-lux alone or together with different constructs of the type I receptor. Sixteen to twenty hours after transfection, cells were treated with TGF-β in 0.2% serum medium for 24 to 28 hours. For testing the effect of FK506 derivative 15-O-desmethyl FK520, cells were treated with the drug beginning two hours prior to the addition of TGF-β. Cell lysates were made and luciferase activity was measured in a luminometer. Each assay was carried out in duplicate or triplicate.

Growth Inhibition Assay Mv1Lu cells were seeded in 12-well plate at $3\times10^4$ cells/well and incubated overnight. Cells were treated with 15-O-demethyl FK520 for 2 hours and with TGF-β for 36 to 40 hours in the presence of the drug. Cells were trypsinized, and cell numbers were determined in a Coulter counter.

Results and Discussion

FKBP12 is a specific interactor for multiple type I receptors of the TGF-β family Using a modified yeast two-hybrid system, we previously isolated the immunophilin FKBP12 as a candidate cytoplasmic interactor of one member (R1) of the type I receptor family (Wang, T. W. et al., Science 265:674–676 (1994)). In order to isolate interactors specific for each of the known type I receptors, we screened two additional yeast expression libraries using cytoplasmic domains of three different type I receptors as baits. FKBP12 was isolated as the predominant interactor for each type I receptor. A novel cDNA which is 66% identical to mouse FKBP12 was isolated from a Drosophila cDNA library as the only interactor for the decapentaplegic (DPP) type I receptor Thickvein (Tkv) (Brummel, T. J. et al., Cell 78:251–261 (1994), and was thus designated the Drosophila FKBP12 (Dr FKBP12) (see FIG. 7). The results of all three screenings are summarized in Table 1.

Figure 1B:
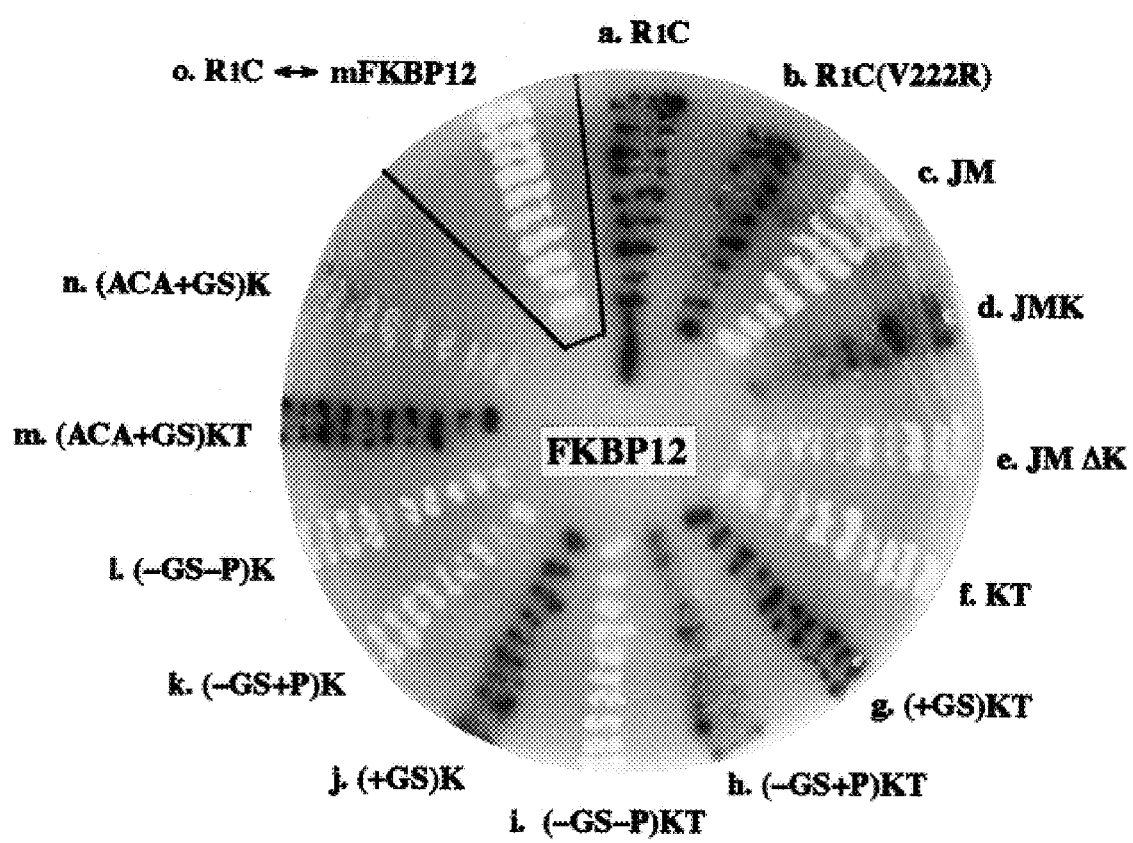
FIGS. 1B and 1C. Deletion and mutation analyses on the cytoplasmic domain of R1 (R1C) to map the FKBP12 binding site.
Figure 1C:
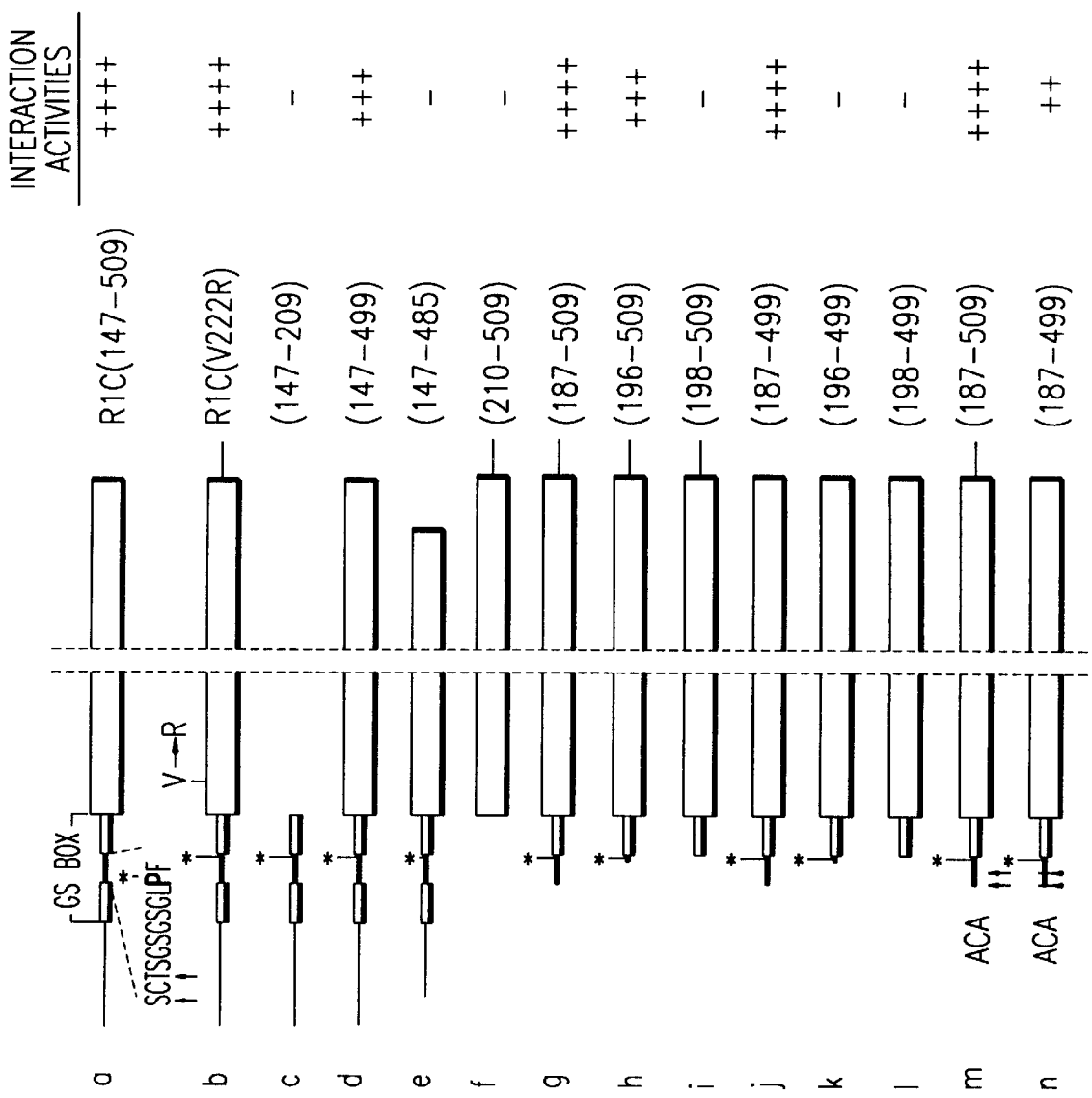

To determine whether FKBP12 also interacts with other known type I receptors, five different mammalian type I receptors (R1–R4, ALK6) (He, W. W. et al., Dev. Dyn. 196:133–142 (1994); ten Dijke P., et al., Oncogene 8:2879 (1993)), two Drosophila type I receptors (Sax, Tkv) (Xie, T. et al., Science 263:1756–1759 (1994); Brummel, T. J. et al., Cell 78:251–261 (1994)), and three mammalian type II receptors (tRII, aRII, mRII, type II receptors for TGF-β, activin and MIS, respectively) (Lin, H. Y. et al., Cell 68:1–20 (1992); Mathews, L. S. and Vale, W. W., Cell 65:973–982 (1991)) were tested for interaction with FKBP12, in the yeast two-hybrid system (FIG. 1, A). All tested type I receptors exhibited strong interaction with FKBP12, while the tested type II receptors did not, which indicates that FKBP12 is a specific interactor for all type I receptors.

Two separate domains of the type I receptors are required for FKBP12 binding

As an immunophilin, FKBP12 interacts with calcineurin or FRAP (or RAFTI) only in the presence of macrolides FK506 and rapamycin, respectively (Liu, J. et al., Cell 66:807–815 (1991); Brown, E. J. et al., Nature 369:756–758 (1994); Sabatini, D. M. et al., Cell 78;35–43 (1994)). Like the TGF-β family type I receptors, the ryanodine receptor (RyR) of skeletal muscle and a structurally and functionally related $Ca^{2+}$ channel, the inositol 1,4,5-trisphosphate (IP3) receptor, can also bind to FKBP12 in the absence of macrolides (Brillantes, A. B. et al., Cell 77:513–523 (1994); Cameron, A. W. et al., Proc. Natl. Acad. Sci. USA 92:1784–1788 (1995)). However, the large size of these receptors imposes difficulties for dissecting the molecular details of their interaction with FKBP12.

To understand the molecular basis of the interaction between the TGF-β family type I receptors and FKBP12, deletion and mutation analyses were carried out on two type I receptors, the functional TGF-β type I receptor (R4) (Bassing, C. et al., Science 263:87–89 (1994); Franzen, P. et al., Cell 75:681–692 (1993)) and a candidate type I receptor for TGF-β, activin and MIS (R1) (Ebner, R. et al., Science 260:1344–1348 (1993); Attisano, L. et al., *Cell* 75:671–680 (1993); He, W. W. et al., *Dev. Dyn.* 196:133–142 (1993)). Since the results were identical, only the domain mapping studies on R1 are shown (FIGS. 1, B&C). Abolishing the ATP binding site of the receptor kinase did not abolish FKBP12 binding (FIGS. 1, B&C, b). Deletion of the tails (last 10 amino acids of R1, last 6 amino acids of R4) alone did not affect FKBP12 binding (FIGS. 1, B&C, d), while deletion of the juxtamembrane (JM) regions completely abolished the interaction (FIGS. 1, B&C, f), suggesting that the JM region, but not the tail, is necessary for FKBP12 binding. Within the JM region, deletion of amino acids just preceding the GS core sequence (SCTSGSGSGLPF (SEQ ID NO:19) for R1, TTSGSGSGLPL (SEQ ID NO:20) for R4) (FIGS. 1, B&C, g), or mutation of the first two serines or threonines (bold letters) (FIGS. 1, B&C, m), did not affect FKBP12 binding; additional deletion of SGSGSG (SEQ ID NO:21) only slightly decreased the interaction (FIGS. 1, B&C, h); however, further deletion of LP completely abolished FKBP12 binding (FIGS. 1, B&C, i). Thus, the FKBP12 binding domain within the JM region is mapped to the residues between SGSGSG (SEQ ID NO:21) and the kinase domain. Within this domain, the sequence LPL(F) (SEQ ID NO:22) is completely conserved among, and specific for all type I receptors.

However, the LPL(F) (SEQ ID NO:22) containing domain alone is not sufficient for FKBP12 binding, since neither the JM alone (FIGS. 1, B&C, c), nor a fusion protein of the JM region of R4 and the cytoplasmic domain of the TGF-β type II receptor exhibited interaction with FKBP12 (not shown). The last seventeen amino acids of the carboxyl-terminus of the kinase domain is also required for FKBP12 binding (FIGS. 1, B&C, d, e). Further deletions within this region mapped the FKBP12 binding domain to the last ten amino acids of the kinase domain (not shown). Within this region, the sequence LRI(V)KKTL (SEQ ID NO:23) is also completely conserved and specific for all type I receptors.

Although deleting the SGSGSG (SEQ ID NO:21) motif within the JM region or deleting the tail region separately did not significantly affect FKBP12 binding (FIGS. 1, B&C, h, d), deleting both regions together completely disrupts the ability of the receptor to bind to FKBP12 (FIGS. 1, B&C, k). Thus, an intramolecular interaction dependent upon the presence of both the SGSGSG (SEQ ID NO:21) motif and the tail may exist to approximate the two separate binding motifs necessary for FKBP12 binding. Since the two FKBP12 binding motifs and the SGSGSG (SEQ ID NO:21) motif are highly conserved and specific for all known type I receptors, FKBP12 is likely a common interactor of the type I receptor family.

The macrolide binding site and the amino-terminus of FKBP12 are both important for the binding of FKBP12 to the type I receptors We previously showed that excess FK506 could partially compete for binding of R4C to FKBP12 in yeast cells (Wang, T. W. et al., *Science* 265:674–676 (1994)). A point mutation within the macrolide binding site of FKBP12 (D37G) abolishes FKBP12 binding to FK506 or rapamycin binding. Such a mutant FKBP12 (mFKBP12) failed to interact with R4 or R1 as well, when tested in the yeast two-hybrid system (FIG. 1, B, o), indicating that the FK506 binding site is important for the the binding of FKBP12 to the type I receptors.

Most cDNAs of FKBP12 isolated from the three different yeast expression libraries (Table 1) were full length although a few had short amino-terminal deletions of less than 6 amino acids. A deletion of five amino acids from the amino-terminal region of FKBP12 completely abolished its ability to bind to R4 (see FIG. 7), indicating that the amino-terminus of FKBP12 is also required for the binding of the type I receptors. FKBP12 belongs to a protein family consisting of members with conserved motifs and is capable of binding to the immunosuppressant macrolides FK506 and rapamycin (Galat, A. et al., *Biochemistry* 31:2427–2434 (1992); Hung, D. T. and Schreiber, S. L., *Biochem. Biophys. Res. Commun.* 184:733–738 (1992); Jin, Y. J. et al., *Proc. Natl. Acad. Sci. USA* 88:6677–6681 (1991); Standaert, R. R. et al., *Nature* 346:671–674 (1990)). Sequence comparisons between FKBP12 and other family members show that the amino terminus of FKBP12 is not conserved within the family (see FIG. 7), which explains why only FKBP12 among all FKBP12 was isolated from the yeast expression libraries, and indicates that the drug binding site alone is not sufficient for the binding of FKBP12 to the type I receptors. FKBP12 binds to the TGF-β type I receptor in the absence of TGF-β

Figure 2A:
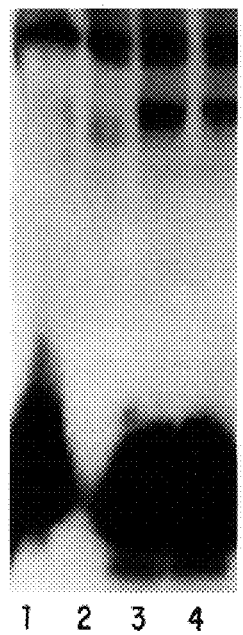
FIG. 2A. COS1 cells were transiently transfected with the indicated plasmids, metabolically labeled with [$^{35}$S]-methionine. Cell lysates were then immunoprecipitated with 5 μl of anti-T7 monoclonal antibody, and the immunoprecipitates were separated on 15% SDS-PAGE, which was then visualized by autoradiography. FKT7, bacteria T7 epitope tag is tagged at the amino-terminus of FKBP12 subcloned in pCMVS. R4, R4 pCMV6; R4K$^-$, R4 (K230R) pCMV6; EV, pCMV6. The immunoprecipitated FKT7 and the co-precipitated R4 are indicated.
Figure 2B:
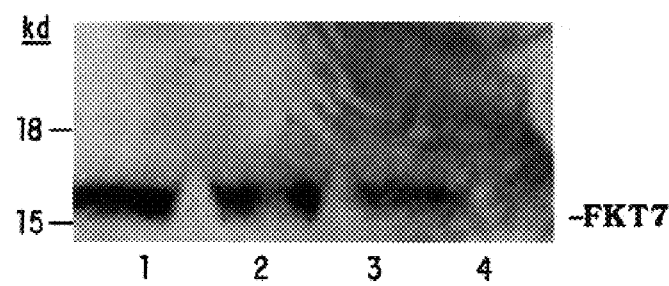
FIG. 2B. COS1 cells were transfected with the indicated plasmids, lysed and then immunoprecipitated with an anti-R4 antiserum (VPN) that recognizes a juxtamembrane region of the receptor (Franzen, P. et al., Cell 75:681–692 (1993)). The immunoprecipitates were then separated on a 15% SDS-PAGE, electrotransferred, and subjected to Western blot using anti-T7 monoclonal antibody, and visualized using ECL (Amersham).
Figure 2C:
FIG. 2C. Total cell lysates in FIG. 2B. were subjected to Western blot using anti-T7 monoclonal antibody.

To confirm the specific interaction between FKBP12 and the cytoplasmic domains of the type I receptors observed in yeast, we further tested the interaction between FKBP12 and the known functional TGF-β type I receptor (R4) in COS cells (FIG. 2). FKBP12 was tagged at its amino-terminus with a T7 tag, and co-expressed with either the wild type R4, or the kinase deficient R4 mutant (R4K⁻=R4K230R) in COS cells which were metabolically labeled with [$^{35}$S]=methionine. Co-immunoprecipitation assays using the transfected COS cell lysates were carried out with monoclonal anti-T7 antibody. The co-precipitated type I receptor was detected by autoradiography (FIG. 2, A). Both the wild type and the kinase deficient mutant were co-precipitated with T7 tagged FKBP12 (FIG. 2, A, lanes 3 & 4), indicating that the kinase activity of the type I receptor is not required for FKBP12 binding, as observed in yeast. To test whether the last seventeen amino acids of the carboxyl-terminus of the R4 kinase domain is important for FKBP12 binding in COS cells, two deletion mutants were made, one lacking the tail region (last six amino acids) of R4 (R4 tailless), and the other lacking both the tail and the carboxyl-terminal 17 amino acids of the kinase domain (R4ΔK). The mutants, as well as the wild type R4, or the kinase deficient R4 (R4K$^{31}$), were co-expressed with T7 tagged FKBP12 in COS cells. The receptors were immunoprecipitated with anti-R4 antiserum, and the co-precipitated FKBP12 detected by Western analyses with anti-T7 antibody (FIG. 2, B). With the same amount of FKBP12 co-expressed with the wild type or the mutant type I receptors (FIG. 2, C), FKBP12 was co-precipitated only with the wild type R4 (FIG. 2, B, lane 1), the kinase deficient R4 (lane 2), or the R4 tailless mutant (lane 3), but not with R4ΔK (lane 4), thus further confirming that the 17 amino acids within the carboxyl-terminus of the R4 kinase domain are necessary for FKBP12 binding.

FKBP12 is released from the TGF-β-bound activated type I receptor

To test how ligand-binding affects R4 interaction with FKBP12, R4 was cotransfected with TGF-β type II receptor (RII) and the T7 tagged FKBP12 into COS cells, and activated by TGF-β. The ligand-bound type I and type II receptors were affinity labeled with [$^{125}$I]-iodinated TGF-β by chemical cross-linking (Massagué, J., *J. Biol. Chem.* 260:7059–7066 (1985); Massagué, J. and Like, B., *J. Biol. Chem.* 260:2636–2645 (1985)). Interestingly, when the T7 tagged FKBP12 was immunoprecipitated by anti-T7 antibody, little, if any ligand-bound wild type R4 was co-precipitated (FIG. 3, A, lane 1), suggesting that FKBP12 is absent from the ligand-bound type I/type II receptor complex.

The type II receptor-mediated type I receptor phosphorylation is responsible for the release of FKBP12

The type I receptor is known to be phosphorylated by the type II receptor in the presence of TGF-β, and may thus be activated as a kinase to autophosphorylate or to phosphorylate unknown substrates (Wrana, J. L. et al., *Nature* 370:341–47 (1994)). To test whether these phosphorylation events are responsible for the release of FKBP12 from R4, we replaced the wild type receptors with the kinase deficient mutant receptors. The [$^{125}$I]-TGF-β-bound receptor complexes were co-precipitated with FKBP12 when the type II receptor kinase was deficient (FIG. 3, A, lanes 2 & 4), but not when the type I receptor kinase was deficient (FIG. 3, A, lane 3), suggesting that the type II receptor-mediated phosphorylation of the type I receptor, not type I receptor autophosphorylation, is necessary for the release of FKBP12.

We further tested whether phosphorylation of the two threonines and three serines within the core sequence of the GS domain TTSGSGSG (SEQ ID NO:18) of the TGF-β type I receptor is responsible for releasing FKBP12, by replacing the threonines and serines with valines and alanines, respectively. The mutant (R4VVAAA) was then tested for its ability to release FKBP12 when co-expressed with the wild type II receptor. Like the wild type R4, the R4VVAAA mutant failed to co-precipitate with FKBP12 in the presence of the wild type II receptor (FIG. 3, A, lane 6), but co-precipitated with FKBP12 in the presence of the kinase deficient type II receptor (FIG. 3, A, lane 5), indicating that phosphorylation of these sites is not responsible for releasing FKBP12.

Since the ligand-bound receptor complex might also release FKBP12 by phosphorylating it, we tested possible ligand-dependent phosphorylation of FKBP12. COS cells transfected with type I and type II receptors together with the T7 tagged FKBP12 were labeled with [$^{32}$P]-orthophosphate and treated with TGF-β. The T7 tagged FKBP12 was immunopreciptated and found not to be phosphorylated either before or after the ligand-induced activation of the receptors (data not shown). Therefore, FKBP12 phosphorylation is not responsible for its release upon ligand binding to the type I receptor.

Non-functional derivatives of FK506 can compete with the type I receptor for FKBP12 binding in COS cells Since the macrolide binding site of FKBP12 appears to be involved in binding to the type I receptors (FIG. 1, B, o), we directly tested whether the interaction between R4 and FKBP12 in COS cells can be blocked by an excess amount of macrolides. Both FK506 and rapamycin each alone exhibited growth inhibition activities when added into the TGF-β responsive mink lung epithelial cell line (Mv1Lu); therefore, we turned to two nonfunctional derivatives of FK506, L685,818 and 15-O-desmethyl-FK520. Both bind to FKBP12 at the same site and with a similar affinity as FK506, but have minimal cellular effects even at very high doses (Dumont, F. J. et al., *J. Exp. Med* 176:751–760 (1992); Becker, J. W. et al., *J. Biol. Chem.* 268:11335–11339 (1993); Liu, J. et al., *Biochemistry* 31:3896–3901 (1992)). COS cells transiently transfected with R4 and T7 tagged FKBP12 were treated with the derivatives and metabolically labeled with [$^{35}$S]-methionine. Anti-T7 antibody was used to precipitate T7 tagged FKBP12 and the co-precipitated R4 was detected by autoradiography as described in FIG. 2, A. Both derivatives are able to block R4/FKBP12 co-immunoprecipitation at 100 nM concentration. The ability of 50 nM L685,818 to block R4 interaction with FKBP12 is shown (FIG. 4, A, lane 3). This data further confirms that the FK506 binding site of FKBP12 is involved in binding to the TGF-β type I receptor.

FKBP12 functions as an inhibitor of the type I receptors

The ability of the non-functional FK506 derivatives to block FKBP12 binding to the inactive TGF-β type I receptor allows us to address the functional role of FKBP12 in the type I receptor-mediated signaling events. If binding to the type I receptors is necessary for FKBP12 to function as a direct signaling molecule, or as a docking protein for a downstream signaling molecule, then blocking FKBP12 binding to the ligand-free type I receptors using excess FK506 derivatives should prevent the activation of the type I receptor-mediated signaling pathway(s), thus abolishing the ligand-induced cellular effects. However, if FKBP12 binding is locking the type I receptors in an inactive conformation, or if FKBP12 is a docking protein for an inhibitor of the type I receptors, then excess FK506 derivatives should release the inhibitory effects of FKBP12. If releasing FKBP12 inhibition is sufficient for activating the type I receptors, the FK506 derivatives should signal downstream events in the absence of either the type II receptors or the ligands. If releasing FKBP12 inhibition alone is only part of a multi-step activation process upon ligand binding, then excess FK506 derivatives alone would not elicit the cellular effects of the TGF-β family ligands, but may potentiate their cellular effects when added together with the TGF-β family ligands.

To distinguish between these possibilities, both 15-O-desmethyl-FK520 and L685,818 were used to test the role of FKBP12 in the signaling events mediated by TGF-β, and yielded very similar results; here we report the results from using 15-O-desmethyl-FK520. In the absence of 15-O-desmethyl-FK520, TGF-β elicits two cellular responses when added into the mink lung epithelial cell line Mv1Lu: the growth inhibition response, which can be detected by a decrease in cell number, and the gene activation response, which can be measured by an increase in the luciferase activities resulting from the activation of a transfected luciferase reporter gene regulated by a Plasminogen Activator Inhibitor (PAI) promotor (Wrana, J. L. et al., *Cell* 71:1003–1014 (1992)). When excess 15-O-desmethyl-FK520 (up to 1 μM) was added together with a low dose of TGF-β (15 pM) into Mv1Lu cells, both cellular responses elicited by TGF-β were not blocked, but instead were greatly enhanced (FIGS. 4 B&C). Neither of the responses were detected when the cells were treated with 1 μM 15-O-desmethyl-FK520 alone (not shown). Therefore, FKBP12 binding to the TGF-β type I receptor is not necessary, but is inhibitory to the type I receptor mediated signaling, and release of FKBP12 is not sufficient for complete activation of the downstream signaling events in the absence of TGF-β.

Since FKBP12 binds to all known type I receptors, its inhibitory activity should therefore also be detected in the signaling events mediated by other TGF-β family members. Müllerian Inhibiting Substance (MIS) is a unique member of the TGF-β family known to be responsible for regression of the Müllerian duct in fetal males through an active apoptotic process (Jost, A., *Arch. Anat. Micro. Morph. Exp.* 36:271–315 (1947); Price, J. M. et al., *Am. J. Anat.* 149:353–376 (1977); Trelstad, R. L. et al., *Devl. Bio.* 92:27–40 (1982)). The activity of MIS in the regression of the Müllerian ducts can be measured directly in an organ culture assay (Donahoe, P. K. et al., *J. Surg. Res.* 23:141–148 (1977)). In this assay, urogenital ridges containing both the Wolffian duct and the Müllerian duct are isolated from fourteen and a half day female fetuses. The isolated urogenital ridges which have had no previous endogenous MIS exposure can then be incubated with different doses of exogenous MIS in an organ culture dish, and the regression of the Müllerian duct can be monitored by histological examination and the degree of the regression can be graded from grade 0 (no regression) to grade 5 (complete regression) as described (Donahoe, P. K. et al., *J. Surg. Res.* 23:141–148 (1977)). When 1 μg MIS was added into the organ culture, grade 1.5 regression was observed, which histologically corresponds to a condensation of the mesenchymal cells surrounding a smaller and irregularly shaped Müllerian duct (FIG. 5, A, top panel). When 1 μM 15-O-desmethyl-FK520 alone was added into the organ culture, no regression activity was detected (FIG. 5, A, bottom panel). However, when 1 μM 15-O-desmethyl-FK520 was added together with 1 μg of MIS, the duct was replaced with a cord of pycnotic epithelial cells and connective tissue (grade 5, or complete regression) (FIG. 5, A, middle panel). We further tested the effect of 1 μM 15-O-desmethyl-FK520 on the regression activities of different doses of MIS (FIG. 5, B). In the presence of 1 μM 15-O-desmethyl-FK520, 0.1 μg MIS has more biological activity than 1 μg MIS alone (FIG. 5, B). L685,818 was shown to have similar effects. When increasing concentrations of L685,818 were added together with 2 μg MIS, a progressive enhancement of the Müllerian duct regression was observed, and complete regression was achieved when 500 nM L685,818 was added together with 2 μg MIS (FIG. 5, C), although 500 nM L685,818 alone caused only minimal regression (Grade 1) (not shown).

These data clearly indicate that FKBP12 also inhibits MIS induced signaling pathways, and that biological activity of MIS required for Müllerian duct regression can be greatly enhanced by using non-functional FK506 derivatives. Since FKBP12 most likely interacts with all members of the TGF-β family type I receptors through the two highly conserved type I receptor-specific domains, we can expect similar effects of the non-functional FK506 derivatives on other members of the TGF-β family.

Multiple events are involved in the activation of type I receptor signaling other than the release of FKBP12

The signaling activities of several R4 mutants were measured by their ability to rescue the TGF-β induced gene response in a mutant mink lung epithelial cell line lacking the functional type I receptor (R1B) (Boyd, F. T. and Massagué, J., *J. Biol. Chem.* 264:2272–2278 (1989); Laiho, M. et al., *J. Biol. Chem.* 265:18518–18524 (1990)) (FIG. 8). The signaling activities as well as the FKBP12 binding/releasing abilities of the R4 mutants are summarized in Table 2. The R4 tailless mutant, which is capable of both FKBP12 binding and release, exhibits normal signaling activity. The R4ΔK mutant, which has an extra 17 amino acid deletion from the carboxyl-terminus of the kinase domain and can not bind to FKBP12, is completely defective in signaling, although its ligand binding as well as its kinase activity are still present (not shown). Since FKBP12 binding is inhibitory to the signaling activity of the type I receptor, the inability of R4ΔK to bind to FKBP12 should make R4ΔK a more active type I receptor, if the deletion only specifically abolishes FKBP12 binding. Recently, however, we found that deletion of the carboxyl-terminal 17 amino acids of the kinase domain also abolishes the binding of another cytoplasmic interactor, the alpha subunit of the p21$^{ras}$ farnesyltransferase (FNTA) (See Example 2 below); therefore, the signaling defect of R4ΔK may be attributed to the disruption of FNTA binding, rather than FKBP12 binding.

Two other mutants, the R4 kinase deficient mutant (R4K230R) and the R4VVAAA mutant, although normal in both binding FKBP12 before activation and releasing FKBP12 after activation, are completely defective in signaling. Thus, ligand induced activation of the type I receptor also involves events that are dependent upon an intact kinase activity and the phosphorylation of the GS domain.

Concluding Remarks

Much is known about the growth stimulatory pathways mediated by tyrosine kinase receptors, while little is known about the growth inhibitory pathways activated by the serine/threonine kinase receptors of the TGF-β family. The evolutionarily conserved, abundant cytoplasmic protein FKBP12 is known to bind exogenous macrolide molecules to mediate immunosuppression; however, its normal physiological roles remain obscure.

By using the yeast two-hybrid system, we identified FKBP12 as a common interactor of the cytoplasmic domains of the TGF-β family type I serine/threonine kinase receptors. We further confirmed the interaction in mammalian cells and found that nonfunctional derivatives of FK506 can compete with the type I receptors in binding to FKBP12. Using these derivatives to release FKBP12 from type I receptors in TGF-β responsive cell line (Mv1Lu) and a Müllerian Inhibiting Substance (MIS) responsive organ (the Müllerian duct), we demonstrated that one important physiological function of FKBP12 is to inhibit the signaling function of the type I receptors by direct binding to the ligand-free type I receptors.

The observation that non-functional derivatives of FK506 can compete with the type I receptors to bind to FKBP12 suggests that an FKBP12 binding domain within the type I receptor may be similar in structure to the FKBP12 binding domain of the macrolides. FKBP12 has peptidyl-prolyl-isomerase activity and binds to the trans-rotamer of macrolides through its catalytic domain (Siekierka, J. J. et al., *Nature* 341:755–777 (1989); Harding, M. W. et al., *Nature* 341:758–760 (1989)). Detailed mutation and deletion studies of the type I receptors have identified an FKBP12 binding motif containing a conserved proline residue in the context of LPF(L) (SEQ ID NO:24), which can be a good substrate for a peptidyl-prolyl-isomerase. Therefore, the special ability of the type I receptors to bind directly to FKBP12 may be due to the presence of the LPF(L) (SEQ ID NO: 24) motif, which may mimic the trans-rotamers of the macrolides and may directly interact with the macrolide binding pocket of FKBP12.

A model for the receptor/FKBP12 interaction is proposed based upon the domain mapping studies shown in FIG. 6, B. In this model, the two separate FKBP12 binding domains of the type I receptors are brought together to bind to the two separate domains of FKBP12, by an intramolecular interaction dependent upon the presence of both the GS core sequence SGSGSG (SEQ ID NO:21) and the short tail. The LPF(L) (SEQ ID NO:24) containing domain within the juxtamembrane region binds to the FKBP12 macrolide binding site, while the KKTL (SEQ ID NO:25) containing motif of the kinase domain binds to a separate domain on FKBP12, possibly the amino-terminus. Molecular modeling based upon the crystal structure of FKBP12 suggests that such a direct interaction can occur. Recent analyses of the X-ray crystal structure of the ternary complex of FKBP12/rapamycin/FRAP (binding peptide) indicated that there are also two positively charged amino acids of FRAP directly facing FKBP12 (FIG. 6, A). Thus, interesting similarities may exist between the FKBP12/type I receptor complex and the FKBP12/rapamycin/FRAP complex (see FIGS. 7, A&B). Resolving the X-ray crystal structure of FKBP12/ type I receptor in the future will allow us to compare the structures of the two complexes directly.

A model is also proposed for the multi-step activation process of the TGF-β type I receptor-mediated signaling pathway (FIG. 6, C). In the presence of TGF-β, the type I receptor forms a heteromeric complex with the type II receptor and is phosphorylated by the type II receptor within the GS domain as well as other unidentified sites (Wrana, J. L. et al., Nature 370:341–47 (1994)). The phosphorylation may induce major conformational changes, which results in the releasing of FKBP12 from the two separate binding domains located within the juxtamembrane region (LPF) and the carboxyl-terminus of the kinase domain (KKTL (SEQ ID NO:25)), respectively. If binding of FKBP12 to the two separate domains of the type I receptor locks the type I receptor in a folded conformation unfavorable for signaling, release of FKBP12 would allow the exposure of the signaling regions on the type I receptor. Phosphorylation of the GS domain by the type II receptor, although not required for releasing FKBP12, is essential for signaling. One possibility is that the phosphorylated GS domain may serve as a binding site for another cytoplasmic interactor (FIG. 6, C). It would not be possible to identify such an interactor by using the cytoplasmic domain of the type I receptor as a bait in the yeast two-hybrid system, since the GS domain is not autophosphorylated (Wieser, R. et al., EMBO J. 14:2199–2208 (1995)). The kinase activity of the type I receptor, although not required for FKBP12 binding or release (FIGS. 2&3), is necessary for signaling, possibly by phosphorylating cytoplasmic interactors such as a GS domain interactor (FIG. 6, C). The other region involved in signaling is the carboxyl-terminus 17 amino acids of R4, as indicated by the signaling defect of R4ΔK (Table 2, and FIG. 8). R4ΔK was shown to be defective in interacting with another cytoplasmic interactor, the alpha subunit of the $p21^{ras}$ farnesyltransferase (See Example 2 below). Interestingly, like FKBP12, FNTA also binds to the ligand-free TGF-β type I receptor, from which it is also released upon ligand-dependent, type II receptor-mediated phosphorylation. Thus, releasing cytoplasmic interactors of the type I receptor upon ligand-induced, type II receptor-mediated serine/threonine phosphorylation of the type I receptors may be a novel signaling mechanism utilized by the TGF-β family members.

By binding to the TGF-β family type I receptors before ligand-mediated activation, FKBP12 could inhibit the type I receptor-mediated signaling pathway(s) through several possible mechanisms. FKBP12/type I receptor interaction may block type I receptor binding to other signaling molecules. Alternatively, FKBP12 binding may inhibit the kinase function of the receptors by either inactivating their kinase catalytic activities or by hindering the approach of substrates to the active catalytic sites; resolving the X-ray crystal structure of the FKBP12/type I receptor complex is necessary to distinguish these possibilities. A third possible mechanism whereby FKBP12 may inhibit the signaling activity of the type I receptors is to serve as a docking protein for a cytoplasmic inhibitor of the type I or type II receptors. A candidate inhibitor is the cytoplasmic serine/threonine phosphatase calcineurin, which has been shown to be recruited by FKBP12 to form a ternary complex with the tetrameric $Ca^{2+}$ channel, inositol 1,4,5-trisphosphate ($IP_3$) receptor, and to modulate the phosphorylation status and $Ca^{2+}$ flux properties of $IP_3R$ (Cameron, A. W. et al., Cell 83:463–472 (1995)). Similarly, FKBP12 could also recruit calcineurin to form a ternary complex with the type I receptors. Wrana et al. (Nature 370:341–47 (1994)) showed that the TGF-β type I receptors in Mv1Lu cells were poorly or not at all phosphorylated before ligand binding in vivo, although the type I receptor is active as a kinase and is capable of autophosphorylation in vitro. It is possible that the cacineurin or another phosphatase could be responsible for dephosphorylating the type I receptor to keep it in the inactive state before ligand binding. Upon ligand binding, the type II receptor-mediated type I receptor phosphorylation releases FKBP12, thus also releases calcineurin, and may thereby allow the type I receptor to be maintained in the phosphorylated and activated conformation. If this proves to be the case, the physiological role of FKBP12 could be as a general docking protein from which calcineurin can dephosphorylate different cytoplasmic proteins which are capable of binding to FKBP12 directly.

We observed that two nonfunctional FK506 derivatives (15-O-desmethyl-FK520, and L685,818) can potentiate the biological activities of TGF-β and MIS. Since FKBP12 is a common inhibitor of the TGF-β family type I receptors, such an effect of the nonfunctional derivatives is predicted for the other TGF-β family ligands. Thus, these nonfunctional derivatives of FK506 have exciting therapeutic applications: one can use TGF-β family ligands for targeted specificity, and use such FK506 nonfunctional derivatives to potentiate the biological activities, thus reducing clinical side effects by using a lower dose of both the TGF-β family ligand and the macrolide potentiator.

TABLE 1

Summary of results of three yeast two-hybrid screens using different cytoplasmic domains of type I receptors as bait.

| Baits | Library | FKBP12 (#/total positives) |
| --- | --- | --- |
| R1C | rat neonatal heart | rFKBP12 (57/76) |
| R4C | human fetal brain | hFKBP12 (54/109) |
| TKV-C | Drosophila imaginal disc | Dr FKBP12 (38/38) |

The entire cytoplasmic domain of R1 (He, W. W. et al., Dev. Dyn. 196:133–142 (1993)), R4 (He, W. W. et al., Dev. Dyn. 196:133–142 (1993), Bassing, C. et al., Science 263:87–89 (1994)) or Thickvein (Tkv) (Brummel, T. J. et al., Cell 78:251–261 (1994)) was fused in frame with the DNA binding domain LexA to serve as the baits in the yeast two hybrid screens. h, human; r, rat; Dr FKBP12, a novel cDNA isolated from Drosophila imaginal disc library (see FIG. 1).

TABLE 2

Summary of the ability of R4 and its mutants in FKBP12 binding and releasing as well as their signaling activities.

|  | FKBP12 binding | FKBP12 releasing | Signal activity |
| --- | --- | --- | --- |
| R4 | + | + | + |
| R4 tailless | + | + | + |
| R4K | + | + | − |
| R4ΔK | − | N/A | − |
| R4VVAAA | + | + | − |

See Material and Methods for details of construction of the R4 mutants.

The disclosure of this example is also described in Wang et al., Cell 86:435–444 (Aug. 9, 1996), incorporated herein by reference.

EXAMPLE 2 p21ras Farnesyltransferase Alpha Subunit in TGF-Beta and Activin Signaling

Cell growth and differentiation are tightly regulated and delicately balanced by the activities of growth stimulators and suppressors. Although much is known about growth stimulatory pathways which act via tyrosine kinase receptors (Cohen, G. B. et al., *Cell* 80:237 (1995); Pawson, T., *Nature* 373:573–580 (1995); Heldin, C.-H., *Cell* 80:213 (1995)), little is known about the growth inhibitory pathways exemplified by the serine-threonine kinase receptors of the TGF-β family. Recent progress in cloning and characterization of the TGF-β family receptors revealed that two membrane serine-threonine kinases, called the type I and type II receptors, form heteromeric complexes. In this functional signaling unit, the TGF-β type II receptor phosphorylates and possibly thereby activates the type I receptor to signal downstream pathways (Massagué, J. et al., *TIBS* 19:548 (1994); Wrana, J. L. et al., *Nature* 370:341 (1994); Wieser, J. et al., *EMBO* 14:2199 (1995)). However, a clear understanding of the molecular mechanisms involved in the activation of the type I receptor-mediated signaling remains obscure until direct downstream cytoplasmic interactors are identified.

Conventional biochemical methods used successfully in the isolation of the cytoplasmic proteins important in tyrosine kinase receptor downstream pathways have so far failed to identify intracellular interactors of the serine-threonine kinase receptors, hence we turned to a modified version of the yeast two hybrid system (Zervos, A. S. et al., *Cell* 72:223 (1993); Wang, T. W. et al., *Science* 265:674 (1994)). The cytoplasmic domain of the TGF-β type I receptor, as determined by binding and functional assays (Franzen, P. et al., *Cell* 75:681 (1993); Bassing, C. H. et al., *Science* 264:87 (1994)), also known as ALK5 (Franzen, P. et al., *Cell* 75:681 (1993)) and R4 (He, W. W. et al., *Dev. Dynam.* 196:133 (1993)), was used as a bait to screen a human fetal brain library (FIG. 9, A). Three groups of interactors were identified. They are the human immunophilin FKBP12 (Standaert, R. F. et al., *Nature* 346:671 (1990)) and two versions of the human a subunit of the p21$^{ras}$ farnesyltransferase (FNTA) (Andres, D. A. et al., *Genomics* 18:105 (1993)) (FIG. 9, B), which differ within the carboxyl-terminus ten amino acids, the region least conserved among species (Andres, D. A. et al., *Genomics* 18:105 (1993)), and also known to be critical for the farnesyltransferase enzyme activity (Andres, D. A. et al., *J. Biol. Chem.* 268:1383 (1993)). Regulation of the expression of these two variants may be important in controlling the activities of the enzyme in vivo.

The immunophilin FKBP12 which was previously isolated as a specific cytoplasmic interactor for another TGF-β family type I receptor (Wang, T. W. et al., *Science* 265:674 (1994)) was found to be a common interactor for all type I receptors (See Example 1 above). The p21$^{ras}$ farnesyltransferase (FTase) is known to play a critical role in the activation of both wild type and oncogenic Ras, by attaching a 15 carbon farnesyl group to the cysteine near the carboxyl-termini of Ras which aids in its membrane association (Hancock, J. F. et al., *Cell* 57:1167 (1989); Schafer, W. R. et al., *Science* 245:379 (1989); Reiss, Y. et al., *Proc. Natl. Acad. Sci. USA* 88:732–6 (1991); Casey, P. J. et al., *Proc. Natl. Acad Sci. USA* 86:8323–27 (1989); Buss, J. E. et al., *Science* 243:1600–03 (1989)). Farnesyltransferase consists of an α and β subunits (Andres, D. A. et al., *Genomics* 18:105 (1993)). The α subunit is also shared by the geranylgeranyltransferase (GGTase), which has a different β subunit known to add a 20 carbon geranylgeranyl group to the γ subunit of neural G proteins and three small G proteins (Seabra, M. C. et al., *Cell* 65:429 (1991); Mumby, S. M. et al., *Proc. Natl. Acad. Sci. USA* 87:5873 (1990); Kawata, M. et al., *Proc. Natl. Acad. Sci. USA* 87:8960 (1990); Yamane, H. K. et al., *Proc. Natl. Acad. Sci. USA* 87:5868 (1990); Yamane, H. K. et al., *Proc. Natl. Acad Sci. USA* 88:286 (1991)). The β subunits of both enzymes are catalytic and recognize specific substrates, while the functional role of the a subunit, aside from regulating and stabilizing the β subunits, is not clear (Andres, D. A. et al., *J. Biol. Chem.* 268:1383 (1993)).

When tested in the yeast system (FIG. 10, A), the α subunit interacted with the β subunit of the farnesyltransferase (FNTB), as expected, and also interacted specifically with the functional type I receptors of TGF-β (R4) and activin (R2), among all tested type I receptors (Franzen, P. et al., *Cell* 75:681 (1993); Bassing, C. H. et al., *Science* 264:87 (1994); He, W. W. et al., *Dev. Dynam.* 196:133 (1993); ten Dijke, P. et al., *Oncogene* 8:2879 (1993); ten Dijke, P. et al., *Science* 264:101 (1994; Brummel, T. J. et al., *Cell* 78:251 (1994); Xie, T. et al., *Science* 263:1756 (1994)); the R4/FNTA interaction appeared not to be dependent upon the kinase activity of R4 and was specific for type I receptors, since a kinase deficient R4 (FIG. 10, A, R4 (K230R)) was still capable of FNTA binding. Neither of the type II receptors of TGF-β and activin exhibited FNTA binding (not shown). The amino-terminus 81 amino acids of the α subunit, previously shown to be important for the enzyme activity of FTase in mammalian cells (Andres, D. A. et al., *J. Biol. Chem.* 268:1383 (1993)), was also found to be essential for R4 binding (FIG. 10, A, R4Δ81FNTA).

The cytoplasmic region of R4 (R4C) contains the juxtamembrane (JM), the serine-threonine kinase (K) and the tail (T) domains. Within the JM domain is a characteristic motif specific for, and highly conserved among, all known type I receptors, the GS box (Warana, J. L. et al., *Mol. Cell. Biol.* 14:944 (1994)), with a core sequence of SGSGSGLPL/F (SEQ ID NO:26). Deletions and mutations of R4C were made to dissect the molecular details of its interaction with FNTA (FIGS. 10, B, C, D). Neither the JM region nor the tail contains the direct FNTA binding motif, since deletion of neither alone (KT, JMK) affected the interaction. Deletion of the last 17 amino acids of the carboxyl-terminus of the kinase domain (JMΔK), however, completely abolished FNTA binding, suggesting that it may contain a binding site. Deletion of the JM region amino-terminus to the GS box core sequence ((+GS)KT) resulted in a significant increase in FNTA binding, suggesting a negative regulatory role for the deleted region; further deletion of the six amino acids of the GS core sequence (SGSGSG (SEQ ID NO:21)) ((−GS+P)KT) did not affect the interaction, but an additional deletion of the tail ((−GS+P)K) completely abolished the interaction, which implies a positive regulatory role of the tail, and also indicates that the JM region and the tail may cooperatively regulate the interaction. Deletion or mutation of the proline within the GS core sequence (SGSGSGLPL (SEQ ID NO:26)) significantly increased FNTA binding ((−GS−P)K, R4PG), which suggests a negative regulatory role of the proline residue. Point mutations of the serines within the GS box core sequence increased FNTA binding (FIGS. 10, B, D), indicating that phosphorylation of this region may regulate FNTA binding.

FNTA specifically co-precipitated with the cytoplasmic domain of R4 (R4C) (FIG. 11) from yeast cell lysates containing B42 and LexA fusion proteins of FNTA and R4C, respectively, but not with the cytoplasmic domain of R1 (He, W. W. et al., *Dev. Dynam.* 196:133 (1993)), a candidate shared receptor of TGF-β and activin (not shown). Histidine tagged FNTA also co-precipitated with ligand-free R4 and FNTB when transiently expressed in COS cells (FIGS. 12, A, B). R4/FNTA interaction was also detected by co-immunoprecipitation experiments using either anti-FNTA, or anti-R4 in COS cells transfected with R4 and FNTA (not shown).

Figure 12A:
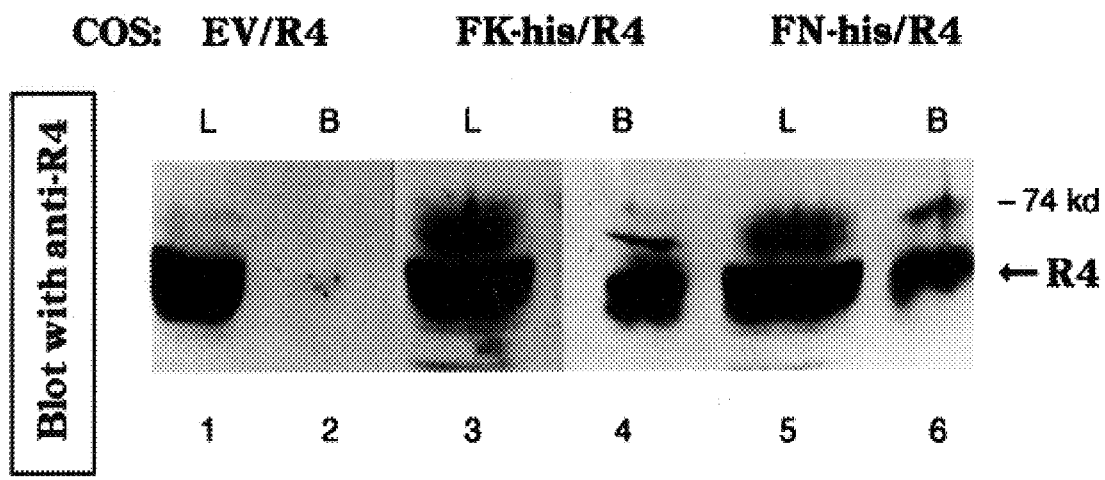
Figure 12B:
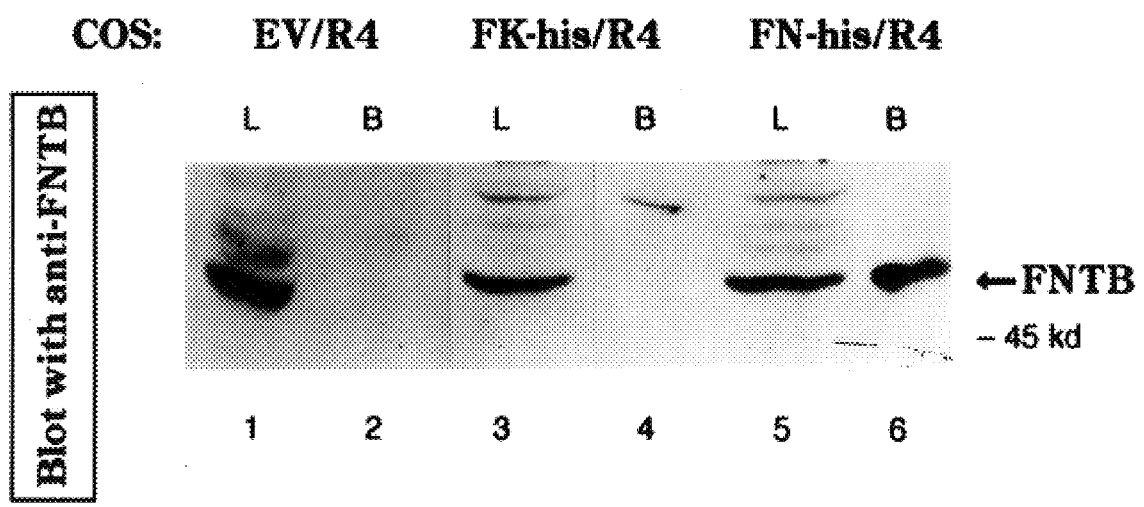
Figure 12C:
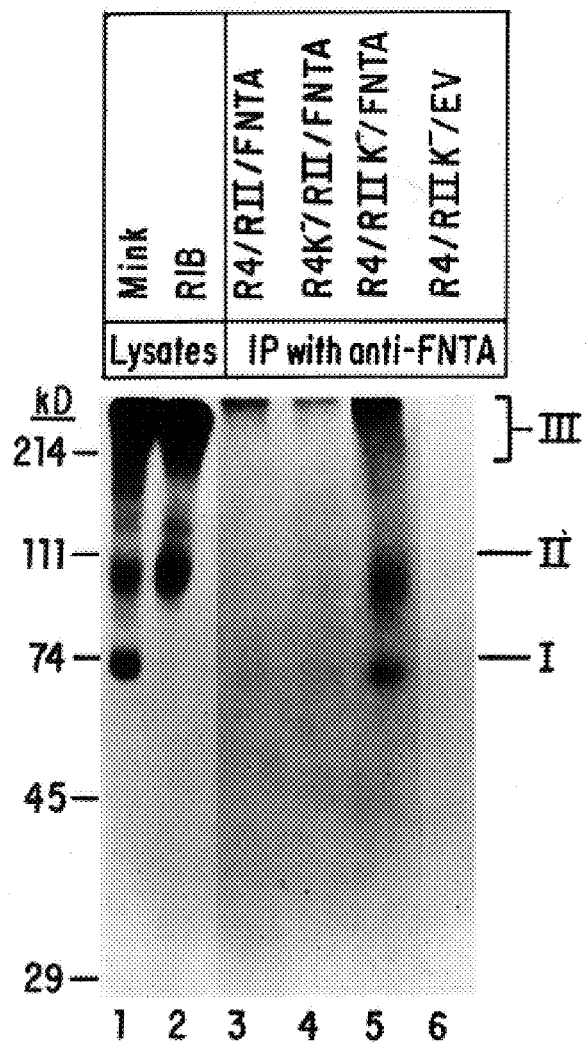
Figure 12D:
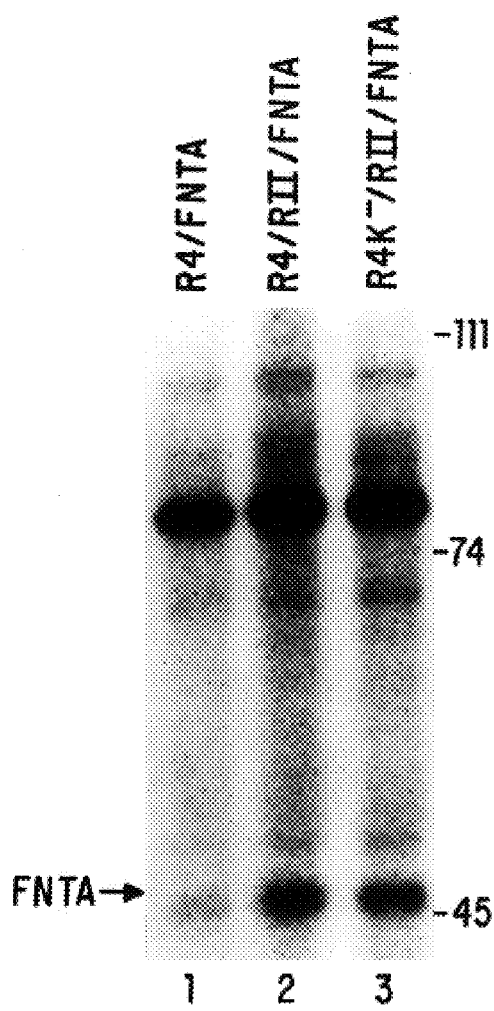
Figure 12E:
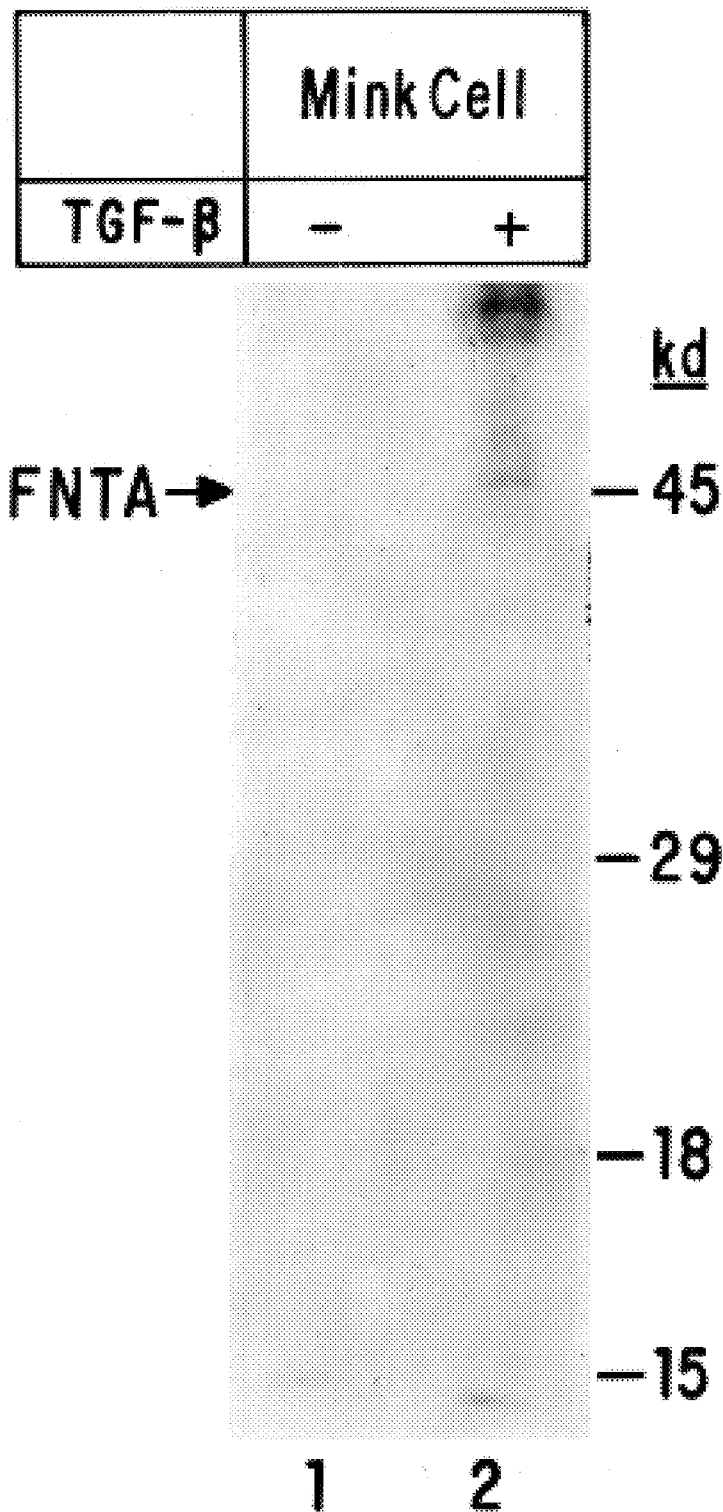
Figure 12F:
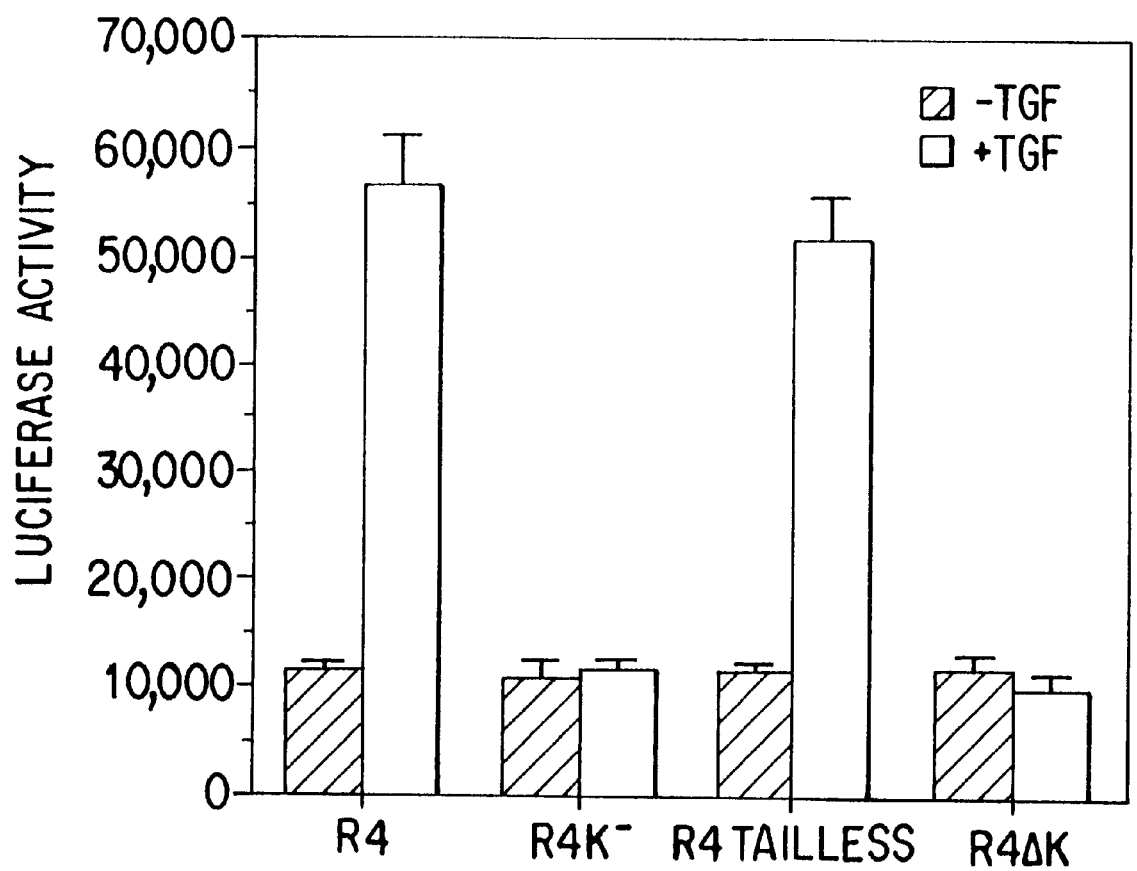

Since mutation studies of R4 suggested a regulatory role of the GS box on R4/FNTA interaction (FIG. 10, R4GS) and the GS box is only phosphorylated by the type II receptor upon ligand binding, we tested the effect of ligand binding on the R4/FNTA interaction. As shown in FIG. 12C, ligand bound wild type R4/RII complexes failed to co-precipitate with FNTA (lane 3) indicating that ligand binding to the receptors can release FNTA. Abolishing the kinase activity of the type II receptor (lane 5), but not the type I receptor (lane 4), prevented the release. This data suggests ligand-induced type II receptor-mediated type I receptor phosphorylation releases FNTA.

To test whether FNTA is a substrate for the receptor serine-threonine kinases, FNTA phosphorylation was measured when it was co-expressed with either R4 alone, or with R4 and tRII in the presence of TGF-β. A basal level of FNTA phosphorylation was detected in COS cells expressing R4 alone (FIG. 12, D, lane 1), or tRII alone, but a significant increase of FNTA phosphorylation was detected in COS cells expressing both R4 and RII in the presence of TGF-β (FIG. 12, D, lane 2). Such an increase is not dependent upon R4 kinase activity, since a point mutation (K230R) abolishing R4 kinase activity did not prevent the ligand-dependent increase of FNTA phosphorylation (FIG. 12, D, lane 3). Thus, the increased FNTA phosphorylation may be mediated by either tRII or receptor-associated kinases. Without overexpressing FNTA or the TGF-β receptors, a ligand-dependent increase of phosphorylation of the endogenous FNTA in the TGF-β responsive mink lung epithelial cell line (Mv1Lu) was also observed (FIG. 12, E).

To test the functional significance of the interaction between FNTA and R4, deletion mutants of R4 were made. Deletion of the carboxyl-terminus tail region of R4 (last five amino acids) did not affect FNTA binding (FIG. 10, B, JMK) nor R4 signaling activity (FIG. 12, F, tailless); however, further deletion of the carboxyl-terminus 17 amino acids of the R4 kinase domain completely abolished both FNTA binding (FIG. 10, B, R4ΔK) and R4 signaling (FIG. 12, F, R4ΔK). R4ΔK binds the ligand normally and has intact autophosphorylation activity (not shown), but is also defective in binding to the other cytoplasmic interactor FKBP12 (See Example 1 above). However, if we block FKBP12 binding to R4 with 15-O-desmethyl-FK520, a nonfunctional derivative of FK506, R4-mediated signaling is enhanced rather than inhibited (See Example 1 above). Therefore, the abrogation of R4ΔK signaling activity may be ascribed to its defect in binding to FNTA.

Thus, the α subunit of the $p21^{ras}$ farnesyltransferase is a specific cytoplasmic interactor of the TGF-β and activin type I receptors whose binding to the TGF-β type I receptor appears to be essential for the signaling activity of the type I receptor. The phenomena of ligand-induced release of FNTA, a precedent also observed in FKBP12 binding to the type I receptor (See Example 1 above), contrasts to what is known about tyrosine kinase receptor activated signaling, and highlights the uniqueness of TGF-β family signaling. Since the alpha subunit is a regulatory subunit shared by the two prenyltransferases, the observed ligand-dependent phosphorylation of the alpha subunit may effect the activity of the enzyme. $P21^{ras}$, an important substrate of the farnesyltransferase, has been shown to be involved in both TGF-β and activin signaling (Mulder, K. M. and Morris, S. L., *J. Biol. Chem.* 267:5029 (1992); Whitman, M. and Melton, D. A., *Nature* 357:252 (1992)). Farnesylation of Ras mediates Ras membrane localization, which is critical for both wild type Ras activity and oncogenic Ras-mediated cell transformation (Hancock, J. F. et al., *Cell* 57:1167 (1989); Schafer, W. R. et al., *Science* 245:379 (1989); Reiss, Y. et al., *Proc. Natl. Acad. Sci. USA* 88:732–6 (1991); Casey, P. J. et al., *Proc. Natl. Acad. Sci. USA* 86:8323–27 (1989); Buss, J. E. et al., *Science* 243:1600–03 (1989)). TGF-β and activin may therefore mediate their growth inhibitory pathways by a direct regulation of the Ras farnesyltransferase.

The disclosure of this example is also described in Wang et al., *Science* 271:1120–1122 (Aug. 9, 1996), incorporated herein by reference.

EXAMPLE 3

Myristylated Wild-Type FKBP12 But Not a Calcineurin-Binding-Deficient FKBP12 Mutant Specifically Blocks TGFβ Responses

Experimental Procedures

See, Example 1, Experimental Procedures, supra. See also, Wang et al., *Cell* 86:435–444 (Aug. 9, 1996), incorporated herein by reference.

Results and Discussion

If, as our data suggests, FKBP12 functions as an inhibitor of the type I receptor, its release from the ligand bound type I receptor should be essential for the activation of the ligand-induced downstream events, and blocking its release should also inhibit the type I receptor-mediated signaling. There are two possible ways to block the release of FKBP12: first, by abolishing the phosphorylation site on the type I receptor responsible for releasing FKBP12; second, by fusing FKBP12 with the cytoplasmic domain of the type I receptor. Since the precise phosphorylation site responsible for FKBP12 release has yet to be identified, and direct fusion of FKBP12 to the type I receptor interfered with the functional conformation of the type I receptor (data not shown), we tested whether the inhibitory activity of FKBP12 could be detected by localizing FKBP12 to the cell membrane to increase its local concentration around the membrane-bound type I receptor. A 13 amino acid src myristylation site was placed at the amino terminus of FKBP12 in a mammalian expression vector pBJ5 (Clipstone, N. W., and Crabtree, G. R., *Nature* 357:695–697 (1992)). Overexpression of this construct (mFE) in Mv1Lu cells greatly reduced the TGFβ induced 3TP-Luc luciferase activities (from 150 to 25-fold) (FIGS. 13A and 13B, "control" and "mFE").

To rule out nonspecific toxicity resulting from overexpressing FKBP12 at the membrane, we used mFE in another TGFβ response assay, the TGFβ-dependent suppression of a cyclin A promoter driven luciferase reporter (FIGS. 13C and 13D). Unlike the 3TP-Luc reporter, which is transcriptionally up-regulated by TGFβ and monitors the pathway that leads to increased production of the extracellular matrix, the cyclin A-Luc reporter is transcriptionally downregulated by TGFβ and monitors the pathway that leads to cell cycle G1 arrest (Feng, X.,-H., et al., *J. Biol. Chem.* 270:24237–24245 (1995)). A specific inhibition of the TGFβ response by overexpression of myristylated FKBP12 should block TGFβ-induced down-regulation of the luciferase activity from the cyclin A-Luc reporter, which should be reflected in an increase in the luciferase activity in the mFE-transfected, TGFβ-treated Mv1Lu cells when compared with the untransfected, TGFβ-treated Mv1Lu cells. A nonspecific toxicity effect of myristylated FKBP12, however, should cause a further decrease of the luciferase activity in the TGFβ-treated, mFE-transfected cells. Overexpression of mFE almost completely blocked the TGFβ-induced repression of the cyclin A-Luc reporter, indicating that the myristylated FKBP12 can specifically inhibit two separate pathways activated by TGFβ in Mv1Lu cells (FIGS. 13C and 13D, "control" and "mFE"). Since FKBP12 is normally released from the type I receptor upon ligand binding (FIG. 3), the myristylated FKBPI2, although not free to travel into the cytoplasm, should also be dissociated from the ligand-bound type I receptor. Therefore, the inhibitory activity of the myristylated FKBP12 is not likely mediated by its direct interaction with the type I receptor activity.

Figure 13E:
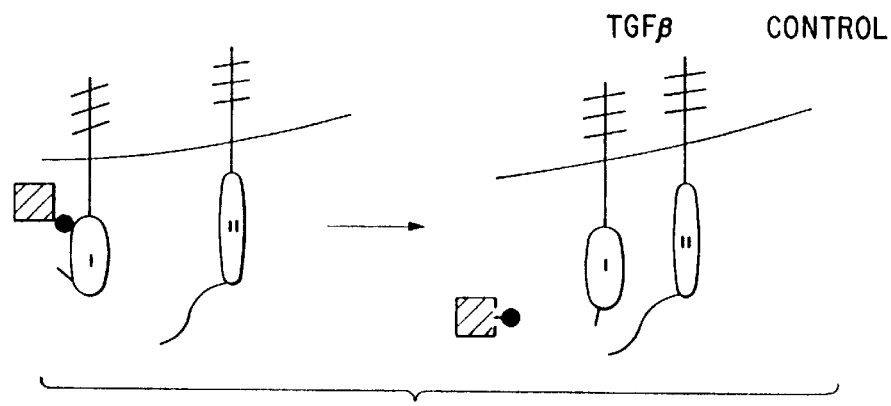
Figure 13F:
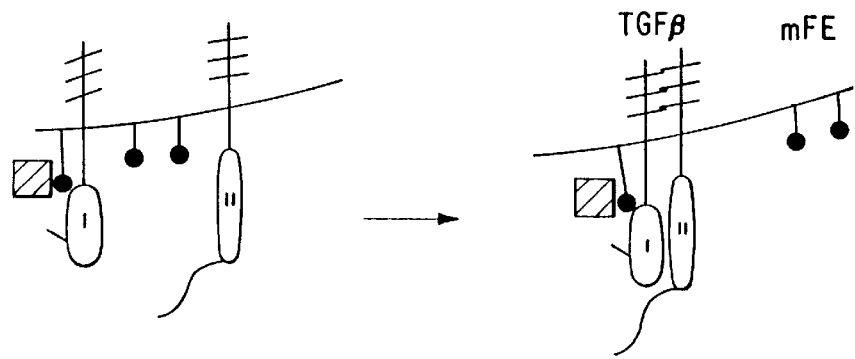
Figure 13G:
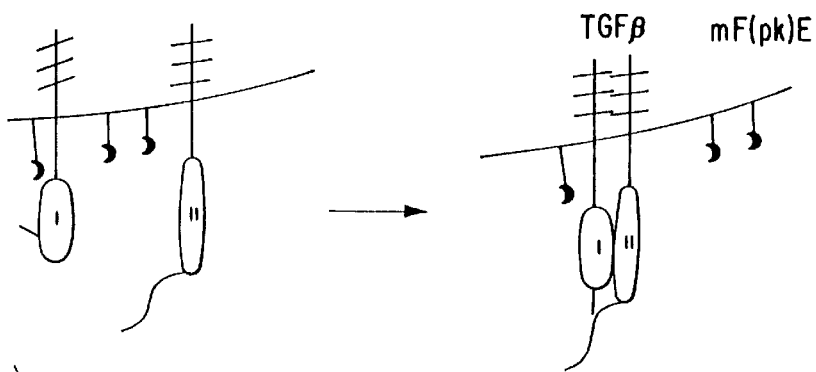

An alternative mechanism for the inhibitory activity of the myristylated FKBP12 is suggested by overexpression of a mutant myristylated FKBP12 (G89P, 190K) in Mv1Lu cells. These mutations are known to be located within the 80s loop of FKBP12 and to abolish calcineurin binding without affecting either FK506 binding or FKBP12 prolyl-isomerase activity (Yang, D., et al., *J. am. Chem. Soc.* 115:819–820 (1993)). The mutant (mF(pk)E) failed to inhibit either of the TGFβ-dependent pathways (FIG. 13, "mF(pk)E"). This data further indicates that FKBP12 may inhibit the type I receptor by docking a cytoplasmic inhibitor, such as calcineurin, as depicted by the cartoon (FIG. 13E). Before ligand binding, FKBP12 docks the inhibitor to the type I receptor, thus preventing receptor signaling. Upon ligand binding, the type II receptor phosphorylates the type I receptor to release FKBP12 and with it, the associated inhibitor (see FIG. 13E, "Control"). The overexpressed myristylated FKBP12 competes with the endogenous FKBP12 to bind to the ligand-free type I receptor, and cannot be released into the cytoplasm upon ligand-induced phosphorylation of the type I receptor, due to its anchorage to the membane, thus allowing the cytoplasmic protein to inhibit the type I receptor in the presence of ligand (see FIG. 13E, "mFE"). The overexpressed mutant FKBP12, although localized to the membrane, fails to dock the inhibitor to the type I receptor, either before, or after ligand binding to the type I receptor. Therefore, normal signaling activity of the type I receptor is detected (see FIG. 13E, "mF(pk)E").

Concluding Remarks

The inhibitory activity of FKBP12 was further tested by overexpression of a myristylated FKBP12 in Mv1Lu cells. Strong and specific inhibition of two separate pathways mediated by TGFβ were detected. The inhibitory activity of the myristylated FKBP12 was abolished by two point mutations known to disrupt FKBP12 binding to calcineurin, but not FKBP12 prolyl-isomerase activity (Yang, D., et al., *J. am. Chem. Soc.* 115:819–820 (1993)). Since ligand-induced type I receptor phosphorylation releases FKBP12, we therefore can conclude that the inhibitory activity of FKBP12 is not mediated by its prolyl-isomerase activity, nor by its direct binding to the type I receptor, but more likely by its ability to dock a cytoplasmic inhibitor of the type I receptor.

One candidate for such an inhibitor is calcineurin. FKBP12 is known to bind to calcineurin with high affinity in the presence of the macrolide FK506. In the absence of FK506, FKBP12 has a weak but specific and functional interaction with calcineurin in yeast (Cardenas, M. E, et al., *EMBO J.* 13:5944–5957 (1994)). Recently, FKBP12 was shown to recruit calcineurin to the $IP_3$ receptor where calcineurin dephosphorylates specific sites on the $IP_3$ receptor to regulate $Ca^2$ influx (Cameron, A. W., et al., *Cell* 83:463–472 (1995)). Interestingly, FK506 can compete with both the $IP_3$ receptor and the TGFβ type I receptor to bind FKBP12, suggesting that similar motifs of the receptors are involved in binding to the same FK506 binding site of FKBP12. The known binding sites on FKBP12 for calcineurin and for FK506 are immediately adjacent to each other (Yang, D., et al., *J. am. Chem. Soc.* 115:819–820 (1993); Kissinger, C. R., et al., *Nature* 378:641–644 (1995)). Therefore, binding of the TGFβ family type I receptors and the huge $IP_3$ receptor to the FK506 binding site of FKBP12 suggests that calcineurin, if also directly bound to FKBP12 in the receptor/FKBP12/calcineurin complex, must be binding to sites removed from the FK506 binding site of FKBP12. Since calcineurin is a serine/threonine phosphatase, while type I receptors are serine/threonine kinases, and phosphorylation of the type I receptor as well as its downstream substrates is essential for signaling via the type I receptors, one plausible mechanism for calcineurin to inhibit the type I receptor signaling activity is to dephosphorylate the type I receptor, or its bound substrates. It will be necessary to detect the ternary complex of calcineurin/FKBP12/type I receptor and these dephosphorylation events in vivo to provide the final proof for such a mechanism.

The model in FIG. 14 summarizes our observations on the inhibitory role of FKBP12 and our hypothesis regarding its potential link to other known events involved in the activation of the TGFβ type I receptor. Before TGFβ binding, FKBP12 binds to the type I receptor, and recruits a cytoplasmic inhibitor, such as calcineurin, to keep the type I receptor inactive, possibly by keeping the type I receptor and its interactor(s), such as the α subunit of the farnesyltransferase (Wang, T. W., et al., *Science* 271:1120–1122 (1996)), hypophosphorylated. The complete activation of the type I receptor can be accomplished in one of two ways. Naturally, high dose TGFβ induces the formation of a tetrameric active signaling complex between the type I and the type II receptors (Weis-Garcia, F., and Massagué, J., *EMBO J.* 15:276–289 (1996)), in which possible sequential activation events occur, involving: (1) GS domain phosphorylation and release of the α subunit of the farnsyltransferase, and probable additional events, and (2) phosphorylation of an additional site to release FKBP12 and its docked inhibitor. Alternatively, complete activation of the type I receptor can be accomplished by using low dose TGFβ to complete (1), and then excess nonfunctional FK506 derivatives to release FKBP12 and its associated inhibitor. Additional mechanisms involved in the direct inactivation of the inhibitor docked by FKBP12, such as phosphorylation of the inhibitor, may also be required during the normal activation of the type I receptor by high dose ligand. Once activated, the type I receptor may then phosphorylate a cytoplasmic substrate, which could be bound to the phosphorylated GS domain, or to other phosphorylated domains. The phosphorylated cytoplasmic substrate(s), together with the released and phosphorylated α subunit of the farnesyltransferase (Wang, T. W., et al., *Science* 271:1120–1122 (1996)), are then responsible for transducing the activation signals downstream. Future studies to map the phosphorylation site(s) responsible for the release of FKBP12, to identify the substrates of the type I receptor kinase, and to dissect the signaling role of the farnesyltransferase α subunit will provide important information for understanding the activation events at or downstream of the TGFβ family type I receptors.

It will be appreciated to those skilled in the art that the invention can be performed within a wide range of equivalent parameters of composition, concentrations, modes of administration, and conditions without departing from the spirit or scope of the invention or any embodiment thereof.

The disclosure of all references, articles, patent applications, and patents recited herein are hereby incorporated by reference.

We claim:

1. A method for potentiating a cellular response, comprising:

(a) administering to cells which express a receptor of a Transforming Growth Factor-beta (TGF-β) family ligand an effective amount of a TGF-β family ligand to induce the receptor-mediated cellular response; and (b) administering to said cells an effective amount of a macrolide which is a naturally occurring or synthetic FK506 or rapamycin derivative, lacks or has reduced immunosuppressive activity as compared to FK506 or rapamycin, respectively, and binds FKBP12 to potentiate the cellular response.

2. The method of claim 1, wherein said macrolide is a FK506 antagonist.

3. The method of claim 2, wherein said FK506 antagonist has the following formula:

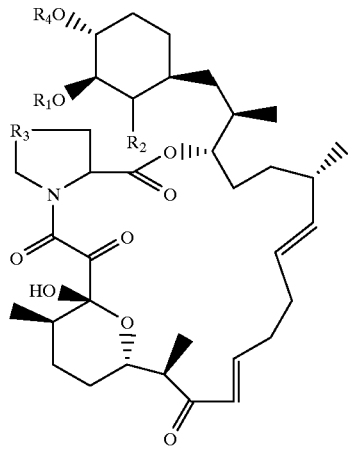

wherein $R_1$ is selected from the group consisting of H, alkyl, aryl and acyl, $R_2$ is selected from the group consisting of H and $-OR_5$, such that $R_5$ is selected from the group consisting of H, alkyl, aryl and acyl, $R_3$ is selected from the group consisting of —$CH_2$— and —$CH_2CH_2$—, and $R_4$ is selected from the group consisting of H, alkyl, acyl and aryl.

4. The method of claim 2, wherein said FK506 antagonist has the following formula:

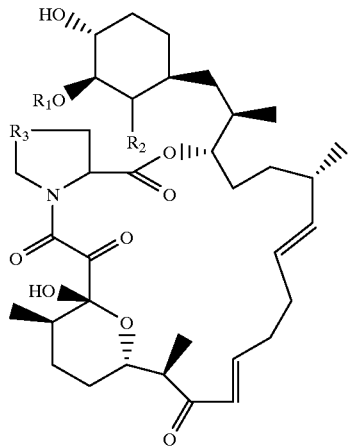

wherein $R_1$ is selected from the group consisting of H and —$CH_3$, $R_2$ is selected from the group consisting of H and —OH, and $R_3$ is selected from the group consisting of —$CH_2$— and —$CH_2CH_2$—.

5. The method of claim 2, wherein said FK506 antagonist is 15-O-desmethyl-FK520.

6. The method of claim 2, wherein said FK506 antagonist is L-685,818.

7. The method of claim 1, wherein said receptor is selected from the group consisting of R1, R2, R3, R4, ALK3, ALK6, Sax and Tkv.

8. The method of claim 2, wherein said receptor is selected from the group consisting of R1, R2, R3, R4, ALK3, ALK6, Sax and Tkv.

9. The method of claim 7, wherein said TGF-β family ligand is selected from the group consisting of TGF-β1, TGF-β2, TGF-β3, TGF-β4, TGF-β5, Müllerian Inhibiting Substance (MIS), an inhibin, an activin, a bone morphogenetic protein, the Vgr-1 gene product, the decapentaplegic gene product, growth differentiation factor (GDF)-1, GDF-2, GDF-3, GDF-4, GDF-5, GDF-6, GDF-7, GDF-8 and GDF-9.

10. The method of claim 8, wherein said TGF-β family ligand is selected from the group consisting of TGF-β1, TGF-β2, TGF-β3, TGF-β4, TGF-β5, Müllerian Inhibiting Substance (MIS), an inhibin, an activin, a bone morphogenetic protein, the Vgr-1 gene product, the decapentaplegic gene product, growth differentiation factor (GDF)-1, GDF-2, GDF-3, GDF-4, GDF-5, GDF-6, GDF-7, GDF-8 and GDF-9.

11. The method of claim 9, wherein said TGF-β family ligand and said macrolide are administered to a patient.

12. The method of claim 10, wherein said TGF-β family ligand and said macrolide are administered to a patient.

13. The method of claim 11, wherein said patient is human.

14. The method of claim 12, wherein said patient is human.

15. The method of claim 13, wherein said TGF-β family ligand is administered before, after, or simultaneously with said macrolide.

16. The method of claim 14, wherein said TGF-β family ligand is administered before, after, or simultaneously with said macrolide.

17. The method of claim 15, wherein said TGF-β family ligand and said macrolide are administered for an effect selected from the group consisting of treatment of an ulcer, prevention or reduction of formation of scar tissue caused by ocular trauma, treatment of psoriasis, inhibition of growth of a gynecological tumor, and inhibition of growth of ocular melanoma.

18. The method of claim 16, wherein said TGF-β family ligand and said macrolide are administered for an effect selected from the group consisting of treatment of an ulcer, prevention or reduction of formation of scar tissue caused by ocular trauma, treatment of psoriasis, inhibition of growth of a gynecological tumor, and inhibition of growth of ocular melanoma.

19. The method of claim 15, wherein said TGF-β family ligand and said macrolide are administered for an effect selected from the group consisting of promotion of proliferation of connective tissue or soft tissue for wound healing and promotion of healing or growth of bone or cartilage.

20. The method of claim 16, wherein said TGF-β family ligand and said macrolide are administered for an effect selected from the group consisting of promotion of proliferation of connective tissue or soft tissue for would healing and promotion of healing or growth of bone or cartilage.

21. A method for potentiating a cellular response, comprising:
(a) administering to a patient having cells which express a receptor of a Transforming Growth Factor-beta (TGF-β) family ligand an effective amount of a TGF-β family ligand to induce the receptor-mediated cellular response; and
(b) administering to said patient a FK506 antagonist which binds FKBP12 but lacks or has reduced immunosuppressive activity as compared to FK506, wherein said antagonist is administered in an amount effective to potentiate the cellular response.

22. The method of claim 21, wherein said TGF-β family ligand is selected from the group consisting of TGF-β1, TGF-β2, TGF-β3, TGF-β4 and TGF-β5.

23. The method of claim 21, wherein said TGF-β family ligand is Müllerian Inhibiting Substance.

24. The method of claim 22, wherein said FK506 antagonist is 15-O-desmethyl-FK520.

25. The method of claim 23, wherein said FK506 antagonist is 15-O-desmethyl-FK520.

26. The method of claim 22, wherein said FK506 antagonist is L-685,818.

27. The method of claim 23, wherein said FK506 antagonist is L-685,818.

28. The method of claim 25, wherein said TGF-β family ligand and said FK506 antagonist are administered to inhibit growth of a gynecological tumor.

29. The method of claim 27, wherein said TGF-β family ligand and said FK506 antagonist are administered to inhibit growth of a gynecological tumor.

30. The method of claim 25, wherein said TGF-β family ligand and said FK506 antagonist are administered to inhibit growth of ocular melanoma.

31. The method of claim 27, wherein said TGF-β family ligand and said FK506 antagonist are administered to inhibit growth of ocular melanoma.

* * * * *